US007001766B2

(12) United States Patent
Shimkets et al.

(10) Patent No.: US 7,001,766 B2
(45) Date of Patent: Feb. 21, 2006

(54) NUCLEIC ACID SEQUENCES ENCODING HUMAN ANGIOPOIETIN-LIKE POLYPEPTIDES

(75) Inventors: Richard A. Shimkets, West Haven, CT (US); Elma Fernandes, Branford, CT (US)

(73) Assignee: CuraGen Corporation, New Haven, CT (US)

( * ) Notice: Subject to any disclaimer, the term of this patent is extended or adjusted under 35 U.S.C. 154(b) by 0 days.

(21) Appl. No.: 10/000,512

(22) Filed: Oct. 23, 2001

(65) Prior Publication Data

US 2002/0164699 A1 Nov. 7, 2002

Related U.S. Application Data

(63) Continuation of application No. PCT/US00/19890, filed on Jul. 20, 2000, and a continuation of application No. 09/619,252, filed on Jul. 19, 2000, now abandoned.
(60) Provisional application No. 60/144,722, filed on Jul. 20, 1999, and provisional application No. 60/167,785, filed on Nov. 29, 1999.

(51) Int. Cl.
*C12N 15/85* (2006.01)

(52) U.S. Cl. .................. 435/325; 435/320.1; 536/23.1; 536/23.5
(58) Field of Classification Search ................. 435/325, 435/320.1, 252.3, 69.1; 536/23.1–24.5
See application file for complete search history.

(56) References Cited

FOREIGN PATENT DOCUMENTS

| JP | 10155490 | 11/1996 |
|---|---|---|
| WO | WO 97/07198 | 2/1997 |
| WO | WO 97/17368 | 5/1997 |
| WO | WO 98/45712 | 10/1998 |
| WO | WO 99/04002 | 1/1999 |
| WO | WO 99/14328 | 3/1999 |
| WO | WO 99/05256 | 4/1999 |
| WO | WO 99/46281 | 9/1999 |

OTHER PUBLICATIONS

Liu et al. Shengming Kexue Yanjiu (2001), 5(3), abstract only.*
Kim et al. Molecular cloning, expression and characterization of angiopoietin–related protein. Journ Biol. Chem. 1999, vol. 274, No. 10, p. 26523–26528.*
"Strategies for Cloning in Plasmid Vectors," Molecular Cloning, A Laboratory Manual, 2$^{nd}$ Ed. pp. 1.53–1.73 and 16.11–16.36.*
Deak, et al., 1997 "Primary structure and expression of matrilin–2, the closest relative of cartilage matrix protein within the von Willebrand factor type A–like module superfamily." J. Biol. Chem. 272 (14), 9268–9274. GenBank Accession No.: O08746.
Inagaki, et al., 1995 "Identification of a member of mouse semaphorin family." FEBS Lett. 370 (3), 269–272. GenBank Accession No.: Q64151.
Kim, et al., 1999 "A catalogue of genes in the human dermal papilla cells as identified by expressed sequence tags." Direct Submission, GenBank Accession No.: Q9Y5B3.
Krieg, et al., 1997 "Repetin (Rptn), a new member of the 'fused gene' subgroup within the S100 gene family encoding a murine epidermal differentiation protein." Genomics 43 (3), 339–348. GenBank Accession No.: P97347.
Nagase, et al., 1999 "Prediction of the coding sequences of unidentified human genes. XIII, The complete sequences of 100 new cDNA clones from brain which code for large proteins in vitro." DNA Res. 6:63–70. GenBank Accession No.: Q9UPZ6.
Steen, R. G., A. E. Kwitek–Black, et al., (1999). "A high–density integrated genetic linkage and radiation hybrid map of the laboratory rat [published erratum appears in Genome Res Aug. 1999; 9(8):793]." *Genome Res* 9(6): AP1–8, insert.
Strausberg, R., 2000 Direct Submission. GenBank Accession No.: O60407.
Yu, et al., 1995 "Molecular cloning, tissue–specific expression, and cellular localization of human prostasin mRNA." J. Biol. Chem. 270 (22), 13483–13489. GenBank Accession No.: Q16651.
Yuan, et al., 1995 "Isolation of a Novel Gene, TSP50, by a Hypomethylated DNA Fragment in Human Breast Cancer." Direct Submission. GenBank Accession No.: Q9U138.
Nagase et al., 1999 "*Homo sapiens* mRNA for KIAA0960 protein, partial cds." Database EMBL (Online) Accession No.: AB023177.
Blandford et al., 1998 "Hypothetical protein (fragment)." Database EMBL (Online) Accession No.: O60407.
Andrews et al., 1998 "Hypothetical protein GS164B05.1 in chromosome 7 (fragment)." Database EMBL (Online) Accession No.: O43384.
Andrew et al., 1998 "Hypothetical protein DJ1110N13.1 in chromosome 7 (fragment)." Database EMBL (Online) Accession No.: O43376.
PCT International Search Report for PCT/US 00/19890, Jan. 19, 2001.

* cited by examiner

*Primary Examiner*—Dave T. Nguyen
*Assistant Examiner*—Jon Eric Angell
(74) *Attorney, Agent, or Firm*—Wendy L Davis; George Yahwak

(57) ABSTRACT

This application is drawn to novel nucleic acid sequences encoding mammalian polypeptides that have sequence similarity to human angiopoietin-related proteins. The nucleic acid sequence is 1855 nucleotides long and contains an open reading frame from nucleotides 154-6 to 1369-71. The encoded polypeptides are about 405 amino acid residues in length.

10 Claims, 35 Drawing Sheets

```
  1  GACAGAGTGCAGCCTTTTCAGACTCTGTGACACAGTTCCCCTTTT
 46  GCAAAAATACTTAGCGAGGATCATTACTTTCCAACAGTCGTGTCC
 91  AGAGACCTACTTTGTAACACCGCAGGGAAGTTAATGTACTAGGTC
136  TTGAAAGGTCTTTCTGGAATGTGCAGTAACTTGTAGTTTTCTTCT
181  AGTAGCACTGCTAATTTTTGTGTTATAATTTTTGTAGGTCCATGG

226  GGCCGATGTATGGGAGATGAATGTGGTCCCGGAGGCATCCAAACG
     MetGlyAspGluCysGlyProGlyGlyIleGlnThr

271  AGGGCTGTGTGGTGTGCTCATGTGGAGGGATGGACTACACTGCAT
     ArgAlaValTrpCysAlaHisValGluGlyTrpThrThrLeuHis

316  ACTAACTGTAAGCAGGCCGAGAGACCCAATAACCAGCAGAATTGT
     ThrAsnCysLysGlnAlaGluArgProAsnAsnGlnGlnAsnCys

361  TTCAAAGTTTGCGATTGGCACAAAGAGTTGTACGACTGGAGACTG
     PheLysValCysAspTrpHisLysGluLeuTyrAspTrpArgLeu

406  GGACCTTGGAATCAGTGTCAGCCCGTGATTTCAAAAAGCCTAGAG
     GlyProTrpAsnGlnCysGlnProValIleSerLysSerLeuGlu

451  AAACCTCTTGAGTGCATTAAGGGGGAAGAAGGTATTCAGGTGAGG
     LysProLeuGluCysIleLysGlyGluGluGlyIleGlnValArg

496  GAGATAGCGTGCATCCAGAAAGACAAAGACATTCCTGCGGAGGAT
     GluIleAlaCysIleGlnLysAspLysAspIleProAlaGluAsp

541  ATCATCTGTGAGTACTTTGAGCCCAAGCCTCTCCTGGAGCAGGCT
     IleIleCysGluTyrPheGluProLysProLeuLeuGluGlnAla

586  TGCCTCATTCCTTGCCAGCAAGATTGCATCGTGTCTGAATTTTCT
     CysLeuIleProCysGlnGlnAspCysIleValSerGluPheSer

631  GCCTGGTCCGAATGCTCCAAGACCTGCGGCAGCGGGCTCCAGCAC
     AlaTrpSerGluCysSerLysThrCysGlySerGlyLeuGlnHis

676  CGGACGCGTCATGTGGTGGCGCCCCGCAGTTCGGAGGCTCTGGC
     ArgThrArgHisValValAlaProProGlnPheGlyGlySerGly

721  TGTCCAAACCTGACGGAGTTCCAGGTGTGCCAATCCAGTCCATGC
     CysProAsnLeuThrGluPheGlnValCysGlnSerSerProCys

766  GAGGCCGAGGAGCTCAGGTACAGCCTGCATGTGGGGCCCTGGAGC
     GluAlaGluGluLeuArgTyrSerLeuHisValGlyProTrpSer

811  ACCTGCTCAATGCCCCACTCCCGACAAGTAAGACAAGCAAGGAGA
     ThrCysSerMetProHisSerArgGlnValArgGlnAlaArgArg
```

Fig 1

```
 856  CGCGGGAAGAATAAAGAACGGGAAAAGGACCGCAGCAAAGGAGTA
      ArgGlyLysAsnLysGluArgGluLysAspArgSerLysGlyVal

901  AAGGATCCAGAAGCCCGCGAGCTTATTAAGAAAAGAGAAACAGA
      LysAspProGluAlaArgGluLeuIleLysLysLysArgAsnArg

946  AACAGGCAGAACAGACAAGAGAACAAATATTGGGACATCCAGATT
      AsnArgGlnAsnArgGlnGluAsnLysTyrTrpAspIleGlnIle

991  GGATATCAGACCAGAGAGGTTATGTGCATTAACAAGACGGGGAAA
      GlyTyrGlnThrArgGluValMetCysIleAsnLysThrGlyLys

1036  GCTGCTGATTTAAGCTTTTGCCAGCAAGAGAAGCTTCCAATGACC
      AlaAlaAspLeuSerPheCysGlnGlnGluLysLeuProMetThr

1081  TTCCAGTCCTGTGTGATCACCAAAGAGTGCCAGGTTTCCGAGTGG
      PheGlnSerCysValIleThrLysGluCysGlnValSerGluTrp

1126  TCAGAGTGGAGCCCCTGCTCAAAAACATGCCATGACATGGTGTCC
      SerGluTrpSerProCysSerLysThrCysHisAspMetValSer

1171  CCTGCAGGCACTCGTGTAAGGACACGAACCATCAGGCAGTTTCCC
      ProAlaGlyThrArgValArgThrArgThrIleArgGlnPhePro

1216  ATTGGCAGTGAAAAGGAGTGTCCAGAATTTGAAGAAAAAGAACCC
      IleGlySerGluLysGluCysProGluPheGluGluLysGluPro

1261  TGTTTGTCTCAAGGAGATGGAGTTGTCCCCTGTGCCACGTATGGC
      CysLeuSerGlnGlyAspGlyValValProCysAlaThrTyrGly

1306  TGGAGAACTACAGAGTGGACTGAGTGCCGTGTGGACCCTTTGCTC
      TrpArgThrThrGluTrpThrGluCysArgValAspProLeuLeu

1351  AGTCAGCAGGACAAGAGGCGCGGCAACCAGACGGCCCTCTGTGGA
      SerGlnGlnAspLysArgArgGlyAsnGlnThrAlaLeuCysGly

1396  GGGGGCATCCAGACCCGAGAGGTGTACTGCGTGCAGGCCAACGAA
      GlyGlyIleGlnThrArgGluValTyrCysValGlnAlaAsnGlu

1441  AACCTCCTCTCACAATTAAGTACCCACAAGAACAAAGAAGCCTCA
      AsnLeuLeuSerGlnLeuSerThrHisLysAsnLysGluAlaSer

1486  AAGCCAATGGACTTAAAATTATGCACTGGACCTATCCCTAATACT
      LysProMetAspLeuLysLeuCysThrGlyProIleProAsnThr

1531  ACACAGCTGTGCCACATTCCTTGTCCAACTGAATGTGAAGTTTCA
      ThrGlnLeuCysHisIleProCysProThrGluCysGluValSer
```

Fig 1 (continued)

1576 CCTTGGTCAGCTTGGGGACCTTGTACTTATGAAAACTGTAATGAT
     ProTrpSerAlaTrpGlyProCysThrTyrGluAsnCysAsnAsp

1621 CAGCAAGGGAAAAAAGGCTTCAAACTGAGGAAGCGGCGCATTACC
     GlnGlnGlyLysLysGlyPheLysLeuArgLysArgArgIleThr

1666 AATGAGCCCACTGGAGGCTCTGGGGTAACCGGAAACTGCCCTCAC
     AsnGluProThrGlyGlySerGlyValThrGlyAsnCysProHis

1711 TTACTGGAAGCCATTCCCTGTGAAGAGCCTGCCTGTTATGACTGG
     LeuLeuGluAlaIleProCysGluGluProAlaCysTyrAspTrp

1756 AAAGCGGTGAGACTGGGAGACTGCGAGCCAGATAACGGAAAGGAG
     LysAlaValArgLeuGlyAspCysGluProAspAsnGlyLysGlu

1801 TGTGGTCCAGGCACGCAAGTTCAAGAGGTTGTGTGCATCAACAGT
     CysGlyProGlyThrGlnValGlnGluValValCysIleAsnSer

1846 GATGGAGAAGAAGTTGACAGACAGCTGTGCAGAGATGCCATCTTC
     AspGlyGluGluValAspArgGlnLeuCysArgAspAlaIlePhe

1891 CCCATCCCTGTGGCCTGTGATGCCCCATGCCCGAAAGACTGTGTG
     ProIleProValAlaCysAspAlaProCysProLysAspCysVal

1936 CTCAGCACATGGTCTACGTGGTCCTCCTGCTCACACACCTGCTCA
     LeuSerThrTrpSerThrTrpSerSerCysSerHisThrCysSer

1981 GGGAAAACGACAGAAGGGAAACAGATACGAGCACGATCCATTCTG
     GlyLysThrThrGluGlyLysGlnIleArgAlaArgSerIleLeu

2026 GCCTATGCGGGTGAAGAAGGTGGAATTCGCTGTCCAAATAGCAGT
     AlaTyrAlaGlyGluGluGlyGlyIleArgCysProAsnSerSer

2071 GCTTTGCAAGAAGTACGAAGCTGTAATGAGCATCCTTGCACAGTG
     AlaLeuGlnGluValArgSerCysAsnGluHisProCysThrVal

2116 TACCACTGGCAAACTGGTCCCTGGGGCCAGTGCATTGAGGACACC
     TyrHisTrpGlnThrGlyProTrpGlyGlnCysIleGluAspThr

2161 TCAGTATCGTCCTTCAACACAACTACGACTTGGAATGGGGAGGCC
     SerValSerSerPheAsnThrThrThrThrTrpAsnGlyGluAla

2206 TCCTGCTCTGTCGGCATGCAGACAAGAAAAGTCATCTGTGTGCGA
     SerCysSerValGlyMetGlnThrArgLysValIleCysValArg

2251 GTCAATGTGGGCCAAGTGGGACCCAAAAAATGTCCTGAAAGCCTT
     ValAsnValGlyGlnValGlyProLysLysCysProGluSerLeu

Fig 1 (continued)

```
2296  CGACCTGAAACTGTAAGGCCTTGTCTGCTTCCTTGTAAGAAGGAC
      ArgProGluThrValArgProCysLeuLeuProCysLysLysAsp

2341  TGTATTGTGACCCCATATAGTGACTGGACATCATGCCCTCTTCG
      CysIleValThrProTyrSerAspTrpThrSerCysProSerSer

2386  TGTAAAGAAGGGGACTCCAGTATCAGGAAGCAGTCTAGGCATCGG
      CysLysGluGlyAspSerSerIleArgLysGlnSerArgHisArg

2431  GTCATCATTCAGCTGCCAGCCAACGGGGGCCGAGACTGCACAGAT
      ValIleIleGlnLeuProAlaAsnGlyGlyArgAspCysThrAsp

2476  CCCCTCTATGAAGAGAAGGCCTGTGAGGCACCTCAAGCGTGCCAA
      ProLeuTyrGluGluLysAlaCysGluAlaProGlnAlaCysGln

2521  AGCTACAGGTGGAAGACTCACAAATGGCGCAGATGCCAATTAGTC
      SerTyrArgTrpLysThrHisLysTrpArgArgCysGlnLeuVal

2566  CCTTGGAGCGTGCAACAAGACAGCCCTGGAGCACAGGAAGGCTGT
      ProTrpSerValGlnGlnAspSerProGlyAlaGlnGluGlyCys

2611  GGGCCTGGGCGACAGGCAAGAGCCATTACTTGTCGCAAGCAAGAT
      GlyProGlyArgGlnAlaArgAlaIleThrCysArgLysGlnAsp

2656  GGAGGACAGGCTGGAATCCATGAGTGCCTACAGTATGCAGGCCCT
      GlyGlyGlnAlaGlyIleHisGluCysLeuGlnTyrAlaGlyPro

2701  GTGCCAGCCCTTACCCAGGCCTGCCAGATCCCCTGCCAGGATGAC
      ValProAlaLeuThrGlnAlaCysGlnIleProCysGlnAspAsp

2746  TGTCAATTGACCAGCTGGTCCAAGTTTTCTTCATGCAATGGAGAC
      CysGlnLeuThrSerTrpSerLysPheSerSerCysAsnGlyAsp

2791  TGTGGTGCAGTTAGGACCAGAAAGCGCACTCTTGTTGGAAAAAGT
      CysGlyAlaValArgThrArgLysArgThrLeuValGlyLysSer

2836  AAAAAGAAGGAAAAATGTAAAAATTCCCATTTGTATCCCCTGATT
      LysLysLysGluLysCysLysAsnSerHisLeuTyrProLeuIle

2881  GAGACTCAGTATTGTCCTTGTGACAAATATAATGCACAACCTGTG
      GluThrGlnTyrCysProCysAspLysTyrAsnAlaGlnProVal

2926  GGGAACTGGTCAGACTGTATTTTACCAGAGGGAAAAGTGGAAGTG
      GlyAsnTrpSerAspCysIleLeuProGluGlyLysValGluVal

2971  TTGCTGGGAATGAAAGTACAAGGAGACATCAAGGAATGCGGACAA
      LeuLeuGlyMetLysValGlnGlyAspIleLysGluCysGlyGln
```

Fig 1 (continued)

```
3016   GGATATCGTTACCAAGCAATGGCATGCTACGATCAAAATGGCAGG
       GlyTyrArgTyrGlnAlaMetAlaCysTyrAspGlnAsnGlyArg

3061   CTTGTGGAAACATCTAGATGTAACAGCCATGGTTACATTGAGGAG
       LeuValGluThrSerArgCysAsnSerHisGlyTyrIleGluGlu

3106   GCCTGCATCATCCCCTGCCCTCAGACTGCAAGCTCAGTGAGTGG
       AlaCysIleIleProCysProSerAspCysLysLeuSerGluTrp

3151   TCCAACTGGTCGCGCTGCAGCAAGTCCTGTGGGAGTGGTGTGAAG
       SerAsnTrpSerArgCysSerLysSerCysGlySerGlyValLys

3196   GTTCGTTCTAAATGGCTGCGTGAAAAACCATATAATGGAGGAAGG
       ValArgSerLysTrpLeuArgGluLysProTyrAsnGlyGlyArg

3241   CCTTGCCCCAAACTGGACCATGTCAACCAGGCACAGGTGTATGAG
       ProCysProLysLeuAspHisValAsnGlnAlaGlnValTyrGlu

3286   GTTGTCCCATGCCACAGTGACTGCAACCAGTACCTATGGGTCACA
       ValValProCysHisSerAspCysAsnGlnTyrLeuTrpValThr

3331   GAGCCCTGGAGCATCTGCAAGGTGACCTTTGTGAATATGCGGGAG
       GluProTrpSerIleCysLysValThrPheValAsnMetArgGlu

3376   AACTGTGGAGAGGGCGTGCAAACCCGAAAAGTGAGATGCATGCAG
       AsnCysGlyGluGlyValGlnThrArgLysValArgCysMetGln

3421   AATACAGCAGATGGCCCTTCTGAACATGTAGAGGATTACCTCTGT
       AsnThrAlaAspGlyProSerGluHisValGluAspTyrLeuCys

3466   GACCCAGAAGAGATGCCCCTGGGCTCTAGAGTGTGCAAATTACCA
       AspProGluGluMetProLeuGlySerArgValCysLysLeuPro

3511   TGCCCTGAGGACTGTGTGATATCTGAATGGGGTCCATGGACCCAA
       CysProGluAspCysValIleSerGluTrpGlyProTrpThrGln

3556   TGTGTTTTGCCTTGCAATCAAAGCAGTTTCCGGCAAAGGTCAGCT
       CysValLeuProCysAsnGlnSerSerPheArgGlnArgSerAla

3601   GATCCCATCAGACAACCAGCTGATGAAGGAAGATCTTGCCCTAAT
       AspProIleArgGlnProAlaAspGluGlyArgSerCysProAsn

3646   GCTGTTGAGAAGAACCCTGTAACCTGAACAAAAACTGCTACCAC
       AlaValGluLysGluProCysAsnLeuAsnLysAsnCysTyrHis

3691   TATGATTATAATGTAACAGACTGGAGTACATGTCAGCTGAGTGAG
       TyrAspTyrAsnValThrAspTrpSerThrCysGlnLeuSerGlu
```

Fig 1 (continued)

3736 AAGGCAGTTTGTGGAAATGGAATAAAAACAAGGATGTTGGATTGT
     LysAlaValCysGlyAsnGlyIleLysThrArgMetLeuAspCys

3781 GTTCGAAGTGATGGCAAGTCAGTTGACCTGAAATATTGTGAAGCG
     ValArgSerAspGlyLysSerValAspLeuLysTyrCysGluAla

3826 CTTGGCTTGGAGAAGAACTGGCAGATGAACACGTCCTGCATGGTG
     LeuGlyLeuGluLysAsnTrpGlnMetAsnThrSerCysMetVal

3871 GAATGCCCTGTGAACTGTCAGCTTTCTGATTGGTCTCCTTGGTCA
     GluCysProValAsnCysGlnLeuSerAspTrpSerProTrpSer

3916 GAATGTTCTCAAACATGTGGCCTCACAGGAAAAATGATCCGAAGA
     GluCysSerGlnThrCysGlyLeuThrGlyLysMetIleArgArg

3961 CGAACAGTGACCCAGCCCTTTCAAGGTGATGGAAGACCATGCCCT
     ArgThrValThrGlnProPheGlnGlyAspGlyArgProCysPro

4006 TCCCTGATGGACCAGTCCAAACCCTGCCCAGTGAAGCCTTGTTAT
     SerLeuMetAspGlnSerLysProCysProValLysProCysTyr

4051 CGGTGGCAATATGGCCAGTGGTCTCCATGCCAAGTGCAGGAGGCC
     ArgTrpGlnTyrGlyGlnTrpSerProCysGlnValGlnGluAla

4096 CAGTGTGGAGAAGGGACCAGAACAAGGAACATTTCTTGTGTAGTA
     GlnCysGlyGluGlyThrArgThrArgAsnIleSerCysValVal

4141 AGTGATGGGTCAGCTGATGATTTCAGCAAAGTGGTGGATGAGGAA
     SerAspGlySerAlaAspAspPheSerLysValValAspGluGlu

4186 TTCTGTGCTGACATTGAACTCATTATAGATGGTAATAAAAATATG
     PheCysAlaAspIleGluLeuIleIleAspGlyAsnLysAsnMet

4231 GTTCTGGAGGAATCCTGCAGCCAGCCTTGCCCAGGTGACTGTTAT
     ValLeuGluGluSerCysSerGlnProCysProGlyAspCysTyr

4276 TTGAAGGACTGGTCTTCCTGGAGCCTGTGTCAGCTGACCTGTGTG
     LeuLysAspTrpSerSerTrpSerLeuCysGlnLeuThrCysVal

4321 AATGGTGAGGATCTAGGCTTTGGTGGAATACAGGTCAGATCCAGA
     AsnGlyGluAspLeuGlyPheGlyGlyIleGlnValArgSerArg

4366 CCGGTGATTATACAAGAACTAGAGAATCAGCATCTGTGCCCAGAG
     ProValIleIleGlnGluLeuGluAsnGlnHisLeuCysProGlu

4411 CAGATGTTAGAAACAAAATCATGTTATGATGGACAGTGCTATGAA
     GlnMetLeuGluThrLysSerCysTyrAspGlyGlnCysTyrGlu

4456 TATAAATGGATGGCCAGTGCTTGGAAGGGCTCTTCCCGAACAGTG
     TyrLysTrpMetAlaSerAlaTrpLysGlySerSerArgThrVal

Fig 1 (continued)

```
4501  TGGTGTCAAAGGTCAGATGGTATAAATGTAACAGGGGGCTGCTTG
      TrpCysGlnArgSerAspGlyIleAsnValThrGlyGlyCysLeu

4546  GTGATGAGCCAGCCTGATGCCGACAGGTCTTGTAACCCACCGTGT
      ValMetSerGlnProAspAlaAspArgSerCysAsnProProCys

4591  AGTCAACCCCACTCGTACTGTAGCGAGACAAAAACATGCCATTGT
      SerGlnProHisSerTyrCysSerGluThrLysThrCysHisCys

4636  GAAGAAGGGTACACTGAAGTCATGTCTTCTAACAGCACCCTTGAG
      GluGluGlyTyrThrGluValMetSerSerAsnSerThrLeuGlu

4681  CAATGCACACTTATCCCCGTGGTGGTATTACCCACCATGGAGGAC
      GlnCysThrLeuIleProValValValLeuProThrMetGluAsp

4726  AAAAGAGGAGATGTGAAAACCAGTCGGGCTGTACATCCAACCCAA
      LysArgGlyAspValLysThrSerArgAlaValHisProThrGln

4771  CCCTCCAGTAACCCAGCAGGACGGGGAAGGACCTGGTTTCTACAG
      ProSerSerAsnProAlaGlyArgGlyArgThrTrpPheLeuGln

4816  CCATTTGGGCCAGATGGGAGACTAAAGACCTGGGTTTACGGTGTA
      ProPheGlyProAspGlyArgLeuLysThrTrpValTyrGlyVal

4861  GCAGCTGGGGCATTTGTGTTACTCATCTTTATTGTCTCCATGATT
      AlaAlaGlyAlaPheValLeuLeuIlePheIleValSerMetIle

4906  TATCTAGCTTGCAAAAAGCCAAAGAAACCCCAAAGAAGGCAAAAC
      TyrLeuAlaCysLysLysProLysLysProGlnArgArgGlnAsn

4951  AACCGACTGAAACCTTTAACCTTAGCCTATGATGGAGATGCCGAC
      AsnArgLeuLysProLeuThrLeuAlaTyrAspGlyAspAlaAsp

4996  ATGTAACATATAACTTTTCCTGGCAACAACCAGTTTCGGCTTTCT
      Met
```

Fig 1 (continued)

```
5041  GACTTCATAGATGTCCAGAGGCCACAACAAATGTATCCAAACTGT
5086  GTGGATTAAAATATATTTTAATTTTTAAAAATGGCATCATAAAGA
5131  CAAGAGTGAAAATCATACTGCCACTGGAGATATTTAAGACAGTAC
5176  CACTTATATACAGACCATCAACCGTGAGAATTATAGGAGATTTAG
5221  CTGAATACATGCTGCATTCTGAAAGTTTTATGTCATCTTTTCTGA
5266  AATCTACCGACTGAAAAACCACTTTCATCTCTAAAAAATAATGGT
5311  GGAATTGGCCAGTTAGGATGCCTGATACAAGACCGTCTGCAGTGT
5356  TAATCCATAAAACTTCCTAGCATGAAGAGTTTCTACCAAGATCTC
5401  CACAATACTATGGTCAAATTAACATGTGTACTCAGTTGAATGACA
5446  CACATTATGTCAGATTATGTACTTGCTAATAAGCAATTTTAACAA
5491  TGCATAACAAATAAACTCTAAGCTAAGCAGAAAATCCACTGAATA
5536  AATTCAGCATCTTGGTGGTCGATGGTAGATTTTATTGACCTGCAT
5581  TTCAGAGACAAAGCCTCTTTTTAAGACTTCTTGTCTCTCTCCAA
5626  AGTAAGAATGCTGGACAAGTACTAGTGTCTTAGAAGAACGAGTCC
5671  TCAAGTTCAGTATTTTATAGTGGTAATTGTCTGGAAAACTAATTT
5716  ACTTGTGTTAATACAATACGTTTCTACTTTCCCTGATTTTCAAAC
5761  TGGTTGCCTGCATCTTTTTTGCTATATGGAAGGCACATTTTTGCA
5806  CTATATTAGTGCAGCACGATAGGCGCTTAACCAGTATTGCCATAG
5851  AAACTGCCTCTTTTCATGTGGGATGAAGACATCTGTGCCAAGAGT
5896  GGCATGAAGACATTTGCAAGTTCTTGTATCCTGAAGAGAGTAAAG
5941  TTCAGTTTGGATGGCAGCAAGATGAAATCAGCTATTACACCTGCT
5986  GTACACACTTCCTCATCACTGCAGCCATTGTGAAATTGACAAC
6031  ATGGCGGTAATTTAAGTGTTGAAGTCCCTAACCCCTTAACCCTCT
6076  AAAAGGTGGATTCCTCTAGTTGGTTTGTAATTGTTCTTTGAAGGC
6121  TGTTTATGACTAGATTTTATATTTGTTATCTTTGTTAAGAAAAA
6166  AAAAAGAAAAGGAACTGGATGTCTTTTTAATTTTGAGCAGATGG
6211  AGAAAATAAATAATGTATCAATGACCTTTGTAACTAAAGGAAAAA
6256  AAAAAAAATGTGGATTTTCCTTTCTCTCTGATTTCCCAGTTTCA
6301  GATTGAATGTCTGTCTTGCAGGCAGTTATTTCAAAATCCATAGTC
6346  TTTNGCCTTTCTCACTGGCAAAATTTGA
```

Fig 1 (continued)

```
   1  CACCCCTCTGCCTGCCCCAGCCCGCCCATCGCTTCCCCTTTGGAG
  46  CCTCCTGCTGGGCCACTGGCTGGGATCAGGACACCAGTGATGGTA
  91  AGTGCTGGCCCAGACTGAAGCTCGGAGAGGCACTCTGCTTGCCCA
 136  GCGTCACAGTCTTAGCTCCCAACTGTCCTGGCTTCCAGTCTCCCT
 181  TGCTTCCCAGATCCCAGACTCTAGCCCCAGCCCCGTCTCTTTCAC
 226  CAGCTCCTGGGACCCTACGCAATCTGCGCCTGCGTCTCATCAGTC
 271  GCCCCACATGTAACTGTATCTACAACCAGCTGCACCAGCGACACC
 316  TGTCCAACCCGGCCCGGCCTGGGATGCTATGTGGGGCCCCCAGC
 361  CTGGGGTGCAGGGCCCCTGTCAGGTCTGATAGGGAGAAGAGAAGG
 406  AGCAGAAGGGGAGGGGCCTAACCCTGGGCTGGGGTTGGACTCAC
 451  AGGACTGGGGGAAAGAGCTGCAATCAGAGGGTGTCTGCCATAGCT
 496  GGGCTCAGGCATCTGTCCTTGGCTTTGTTGCCTGGCTCCAGGGAG
 541  ATTCCGGGGGCCCTGTGCTGTGCCTCGAGCCTGACGGACACTGGG
 586  TTCAGGCTGGCATCATCAGCTTTGCATCAAGCTGTGCCCAGGAGG
 631  ACGCTCCTGTGCTGCTGACCAACACAGCTGCTCACAGTTCCTGGC
 676  TGCAGGCTCGAGTTCAGGGGGCAGCTTTCCTGGCCCAGAGCCCAG

721  AGACCCCGGAGATGAGTGATGAGGACAGCTGTGTAGCCTGTGGAT
      MetSerAspGluAspSerCysValAlaCysGlyS

766  CCTTGAGGACAGCAGGTCCCCAGGCAGGAGCACCCTCCCCATGGC
      erLeuArgThrAlaGlyProGlnAlaGlyAlaProSerProTrpP

811  CCTGGGAGGCCAGGCTGATGCACCAGGGACAGCTGGCCTGTGGCG
      roTrpGluAlaArgLeuMetHisGlnGlyGlnLeuAlaCysGlyG

856  GAGCCCTGGTGTCAGAGGAGGCGGTGCTAACTGCTGCCCACTGCT
      lyAlaLeuValSerGluGluAlaValLeuThrAlaAlaHisCysP

901  TCAATGGGCGCCAGGCCCCAGAGGAATGGAGCGTAGGGCTGGGA
      heAsnGlyArgGlnAlaProGluGluTrpSerValGlyLeuGlyT

946  CCAGACCGGAGGAGTGGGGCCTGAAGCAGCTCATCCTGCATGGAG
      hrArgProGluGluTrpGlyLeuLysGlnLeuIleLeuHisGlyA

991  CCTACACCCACCCTGAGGGGGGCTACGACATGGCCCTCCTGCTGC
      laTyrThrHisProGluGlyGlyTyrAspMetAlaLeuLeuLeuL

1036  TGGCTCAGCCTGTGACACTGGGAGCCAGCCTGCGGGCCCTCTGCC
      euAlaGlnProValThrLeuGlyAlaSerLeuArgAlaLeuCysL

1081  TGCCCTATTTTGACCACCACCTGCCTGATGGGGAGCGTGGCTGGG
      euProTyrPheAspHisHisLeuProAspGlyGluArgGlyTrpV

1126  TTCTGGGACGGGCCCGCCCAGGAGCAGGCATCAGCTCCCTCCAGA
      alLeuGlyArgAlaArgProGlyAlaGlyIleSerSerLeuGlnT

1171  CAGTGCCCGTGACCCTCCTGGGGCCTAGGGCCTGCAGCCGGCTGC
      hrValProValThrLeuLeuGlyProArgAlaCysSerArgLeuH
```

Fig. 2

1216 ATGCAGCTCCTGGGGGTGATGGCAGCCCTATTCTGCCGGGGATGG
     isAlaAlaProGlyGlyAspGlySerProIleLeuProGlyMetV

1261 TGTGTACCAGTGCTGTGGGTGAGCTGCCCAGCTGTGAGGGCCTGT
     alCysThrSerAlaValGlyGluLeuProSerCysGluGlyLeuS

1306 CTGGGGCACCACTGGTGCATGAGGTGAGGGGCACATGGTTCCTGG
     erGlyAlaProLeuValHisGluValArgGlyThrTrpPheLeuA

1351 CCGGGCTGCACAGCTTCGGAGATGCTTGCCAAGGCCCCGCCAGGC
     laGlyLeuHisSerPheGlyAspAlaCysGlnGlyProAlaArgP

1396 CGGCGGTCTTCACCGCGCTCCCTGCCTATGAGGACTGGGTCAGCA
     roAlaValPheThrAlaLeuProAlaTyrGluAspTrpValSerS

1441 GTTTGGACTGGCAGGTCTACTTCGCCGAGGAACCAGAGCCCGAGG
     erLeuAspTrpGlnValTyrPheAlaGluGluProGluProGluA

1486 CTGAGCCTGGAAGCTGCCTGGCCAACATAAGCCAACCAACCAGCT
     laGluProGlySerCysLeuAlaAsnIleSerGlnProThrSerC

1531 GCTGACAGGGGACCTGGCCATTCTCAGGACAAGAGAATGCAGGCA
     ys

1576 GGCAAATGGCATTACTGCCCCTGTCCTCCCCACCCTGTCATGTGT
1621 GATTCCAGGCACCAGGGCAGGCCCAGAAGCCCAGCAGCTGTGGGA
1666 AGGAACCTGCCTGGGGCCACAGGTGCCCCCTCCCCACCCTGCAGG
1711 ACAGGGGTGTCTGTGGACACTCCACACCCAACTCTGCTACCAAG
1756 CAGGCGTCTCAGCTTTCCTCCTCCTTTACCCTTTCAGATACAATC
1801 ACGCCAGCCCCGTTGTTTTGAAAATTTCTTTTTTTGGGGGCAGC
1846 AGTTTTCCTTTTTTTAAACTTAAATAAATTGTTACAAAATAGACT
1891 TTAG

Fig. 2 (continued)

```
  1  GCGGATCCTCACACGACTGTGATCCGATTCTTTCCAGCGGCTTCT
 46  GCAACCAAGCGGGTCTTACCCCCGGTCCTCCGCGTCTCCAGTCCT
 91  CGCACCTGGAACCCCAACGTCCCCGAGAGTCCCCGAATCCCCGCT

136  CCCAGGCTACCTAAGAGGATGAGCGGTGCTCCGACGGCCGGGGCA
                        MetSerGlyAlaProThrAlaGlyAla

181  GCCCTGATGCTCTGCGCCGCCACCGCCGTGCTACTGAGCGCTCAG
     AlaLeuMetLeuCysAlaAlaThrAlaValLeuLeuSerAlaGln

226  GGCGGACCCGTGCAGTCCAAGTCGCCGCGCTTTGCGTCCTGGGAC
     GlyGlyProValGlnSerLysSerProArgPheAlaSerTrpAsp

271  GAGATGAATGTCCTGGCGCACGGACTCCTGCAGCTCGGCCAGGGG
     GluMetAsnValLeuAlaHisGlyLeuLeuGlnLeuGlyGlnGly

316  TGCGCGAACACCGGAGCGCACCCGCAGTCAGCTGAGCGCGCTGGA
     CysAlaAsnThrGlyAlaHisProGlnSerAlaGluArgAlaGly

361  GCGCGCCTGAGCGCGTGCGGGTCCGCCTGTCAGGGAACCGAGGGG
     AlaArgLeuSerAlaCysGlySerAlaCysGlnGlyThrGluGly

406  TCCACCGACCTCCCGTTAGCCCCTGAGAGCCGGGTGGACCCTGAG
     SerThrAspLeuProLeuAlaProGluSerArgValAspProGlu

451  GTCCTTCACAGCCTGCAGACACAACTCAAGGCTCAGAACAGCAGG
     ValLeuHisSerLeuGlnThrGlnLeuLysAlaGlnAsnSerArg

496  ATCCAGCAACTCTTCCACAAGGTGGCCCAGCAGCAGCGGCACCTG
     IleGlnGlnLeuPheHisLysValAlaGlnGlnGlnArgHisLeu

541  GAGAAGCAGCACCTGCGAATTCAGCATCTGCAAAGCCAGTTTGGC
     GluLysGlnHisLeuArgIleGlnHisLeuGlnSerGlnPheGly

586  CTCCTGGACCACAAGCACCTAGACCATGAGGTGGCCAAGCCTGCC
     LeuLeuAspHisLysHisLeuAspHisGluValAlaLysProAla

631  CGAAGAAAGAGGCTGCCCGAGATGGCCCAGCCAGTTGACCCGGCT
     ArgArgLysArgLeuProGluMetAlaGlnProValAspProAla

676  CACAATGTCAGCCGCCTGCACCGGCTGCCCAGGGATTGCCAGGAG
     HisAsnValSerArgLeuHisArgLeuProArgAspCysGlnGlu

721  CTGTTCCAGGTTGGGGAGAGGCAGAGTGGACTATTTGAAATCCAG
     LeuPheGlnValGlyGluArgGlnSerGlyLeuPheGluIleGln

766  CCTCAGGGGTCTCCGCCATTTTTGGTGAACTGCAAGATGACCTCA
     ProGlnGlySerProProPheLeuValAsnCysLysMetThrSer
```

Fig. 3

```
 811  GATGGAGGCTGGACAGTAATTCAGAGGCGCCACGATGGCTCAGTG
      AspGlyGlyTrpThrValIleGlnArgArgHisAspGlySerVal

856  GACTTCAACCGGCCCTGGGAAGCCTACAAGGCGGGGTTTGGGGAT
      AspPheAsnArgProTrpGluAlaTyrLysAlaGlyPheGlyAsp

901  CCCCACGGCGAGTTCTGGCTGGGTCTGGAGAAGGTGCATAGCATG
      ProHisGlyGluPheTrpLeuGlyLeuGluLysValHisSerMet

946  ATGGGGGACCGCAACAGCCGCCTGGCCGTGCAGCTGCGGGACTGG
      MetGlyAspArgAsnSerArgLeuAlaValGlnLeuArgAspTrp

991  GATGGCAACGCCGAGTTGCTGCAGTTCTCCGTGCACCTGGGTGGC
      AspGlyAsnAlaGluLeuLeuGlnPheSerValHisLeuGlyGly

1036  GAGGACACGGCCTATAGCCTGCAGCTCACTGCACCCGTGGCCGGC
      GluAspThrAlaTyrSerLeuGlnLeuThrAlaProValAlaGly

1081  CAGCTGGGCGCCACCACCGTCCCACCCAGCGGCCTCTCCGTACCC
      GlnLeuGlyAlaThrThrValProProSerGlyLeuSerValPro

1126  TTCTCCACTTGGGACCAGGATCACGACCTCCGCAGGGACAAGAAC
      PheSerThrTrpAspGlnAspHisAspLeuArgArgAspLysAsn

1171  TGCGCCAAGAGCCTCTCTGGAGGCTGGTGGTTTGGCACCTGCAGC
      CysAlaLysSerLeuSerGlyGlyTrpTrpPheGlyThrCysSer

1216  CATTCCAACCTCAACGGCCAGTACTTCCGCTCCATCCCACAGCAG
      HisSerAsnLeuAsnGlyGlnTyrPheArgSerIleProGlnGln

1261  CGGCAGAAGCTTAAGAAGGGAATCTTCTGGAAGACCTGGCGGGGC
      ArgGlnLysLeuLysLysGlyIlePheTrpLysThrTrpArgGly

1306  CGCTACTACCCGCTGCAGGCCACCACCATGTTGATCCAGCCCATG
      ArgTyrTyrProLeuGlnAlaThrThrMetLeuIleGlnProMet

1351  GCAGCAGAGGCAGCCTCCTAGCGTCCTGGCTGGGCCTGGTCCCAG
      AlaAlaGluAlaAlaSer

1396  GCCCACGAAAGACGGTGACTCTTGGCTCTGCCCGAGGATGTGGCC
1441  GTTCCCTGCCTGGGCAGGGGCTCCAAGGAGGGGCCATCTGGAAAC
1486  TTGTGGACAGAGAAGAAGACCACGACTGGAGAAGCCCCCTTTCTG
1531  AGTGCAGGGGGCTGCATGCGTTGCCTCCTGAGATCGAGGCTGCA
1576  GGATATGCTCAGACTCTAGAGGCGTGGACCAAGGGGCATGGAGCT
1621  TCACTCCTTGCTGGCCAGGGAGTTGGGGACTCAGAGGGACCACTT
1666  GGGGCCAGCCAGACTGGCCTCAATGGCGGACTCAGTCACATTGAC
1711  TGACGGGGACCAGGGCTTGTGTGGGTCGAGAGCGCCTCATGGTG
1756  CTGGTGCTGTTGTGTGTAGGTCCCCTGGGGACACAAGCAGGCGCC
1801  AATGGTATCTGGGCGGAGCTACAGAGTTCTTGGAATAAAAGCAA
1846  CCTCAGAACA
```

Fig. 3 (continued)

```
  1  GGTAGCCGACGCGCCGGCCGGCGCGTGACCTTGCCCCTCTTGCTC

46  GCCTTGAAAATGGAAAAGATGCTCGCAGGCTGCTTTCTGCTGATC
              MetGluLysMetLeuAlaGlyCysPheLeuLeuIle

91  CTCGGACAGATCGTCCTCCTCCCTGCCGAGGCCAGGGAGCGGTCA
     LeuGlyGlnIleValLeuLeuProAlaGluAlaArgGluArgSer

136  CGTGGGAGGTCCATCTCTAGGGGCAGACACGCTCGGACCCACCCG
     ArgGlyArgSerIleSerArgGlyArgHisAlaArgThrHisPro

181  CAGACGGCCCTTCTGGAGAGTTCCTGTGAGAACAAGCGGGCAGAC
     GlnThrAlaLeuLeuGluSerSerCysGluAsnLysArgAlaAsp

226  CTGGTTTTCATCATTGACAGCTCTCGCAGTGTCAACACCCATGAC
     LeuValPheIleIleAspSerSerArgSerValAsnThrHisAsp

271  TATGCAAAGGTCAAGGAGTTCATCGTGGACATCTTGCAATTCTTG
     TyrAlaLysValLysGluPheIleValAspIleLeuGlnPheLeu

316  GACATTGGTCCTGATGTCACCCGAGTGGGCCTGCTCCAATATGGC
     AspIleGlyProAspValThrArgValGlyLeuLeuGlnTyrGly

361  AGCACTGTCAAGAATGAGTTCTCCCTCAAGACCTTCAAGAGGAAG
     SerThrValLysAsnGluPheSerLeuLysThrPheLysArgLys

406  TCCGAGGTGGAGCGTGCTGTCAAGAGGATGCGGCATCTGTCCACG
     SerGluValGluArgAlaValLysArgMetArgHisLeuSerThr

451  GGCACCATGACTGGGCTGGCCATCCAGTATGCCCTGAACATCGCA
     GlyThrMetThrGlyLeuAlaIleGlnTyrAlaLeuAsnIleAla

496  TTCTCAGAAGCAGAGGGGGCCCGGCCCCTGAGGGAGAATGTGCCA
     PheSerGluAlaGluGlyAlaArgProLeuArgGluAsnValPro

541  CGGGTCATAATGATCGTGACGGATGGGAGACCTCAGGACTCCGTG
     ArgValIleMetIleValThrAspGlyArgProGlnAspSerVal

586  GCCGAGGTGGCTGCTAAGGCACGGGACACGGGCATCCTAATCTTT
     AlaGluValAlaAlaLysAlaArgAspThrGlyIleLeuIlePhe

631  GCCATTGGTGTGGGCCAGGTAGACTTCAACACCTTGAAGTCCATT
     AlaIleGlyValGlyGlnValAspPheAsnThrLeuLysSerIle

676  GGGAGTGAGCCCCATGAGGACCATGTCTTCCTTGTGGCCAATTTC
     GlySerGluProHisGluAspHisValPheLeuValAlaAsnPhe

721  AGCCAGATTGAGACGCTGACCTCCGTGTTCCAGAAGAAGTTGTGC
     SerGlnIleGluThrLeuThrSerValPheGlnLysLysLeuCys
```

Fig. 4

```
 766  ACGGCCCACATGTGCAGCACCCTGGAGCATAACTGTGCCCACTTC
      ThrAlaHisMetCysSerThrLeuGluHisAsnCysAlaHisPhe

811  TGCATCAACATCCCTGGCTCATACGTCTGCAGGTGCAAACAAGGC
      CysIleAsnIleProGlySerTyrValCysArgCysLysGlnGly

856  TACATTCTCAACTCGGATCAGACGACTTGCAGAATCCAGGATCTG
      TyrIleLeuAsnSerAspGlnThrThrCysArgIleGlnAspLeu

901  TGTGCCATGGAGGACCACAACTGTGAGCAGCTCTGTGTGAATGTG
      CysAlaMetGluAspHisAsnCysGluGlnLeuCysValAsnVal

946  CCGGGCTCCTTCGTCTGCGAGTGCTACAGTGGCTACGCCCTGGCT
      ProGlySerPheValCysGluCysTyrSerGlyTyrAlaLeuAla

991  GAGGATGGGAAGAGGTGTGTGGCTGTGGACTACTGTGCCTCAGAA
      GluAspGlyLysArgCysValAlaValAspTyrCysAlaSerGlu

1036  AACCACGGATGTGAACATGAGTGTGTAAATGCTGATGGCTCCTAC
      AsnHisGlyCysGluHisGluCysValAsnAlaAspGlySerTyr

1081  CTTTGCCAGTGCCATGAAGGATTTGCTCTTAACCCAGATGAAAAA
      LeuCysGlnCysHisGluGlyPheAlaLeuAsnProAspGluLys

1126  ACGTGCACAAAGATAGACTACTGTGCCTCATCTAATCATGGATGT
      ThrCysThrLysIleAspTyrCysAlaSerSerAsnHisGlyCys

1171  CAGTACGAGTGTGTTAACACAGATGATTCCTATTCCTGCCACTGC
      GlnTyrGluCysValAsnThrAspAspSerTyrSerCysHisCys

1216  CTGAAAGGCTTTACCCTGAATCCAGATAAGAAAACCTGCAGAAGG
      LeuLysGlyPheThrLeuAsnProAspLysLysThrCysArgArg

1261  ATCAACTACTGTGCACTGAACAAACCGGGCTGTGAGCATGAGTGC
      IleAsnTyrCysAlaLeuAsnLysProGlyCysGluHisGluCys

1306  GTCAACATGGAGGAGAGCTACTACTGCCGCTGCCACCGTGGCTAC
      ValAsnMetGluGluSerTyrTyrCysArgCysHisArgGlyTyr

1351  ACTCTGGACCCCAATGGCAAACCCTGCAGCCGAGTGGACCACTGT
      ThrLeuAspProAsnGlyLysProCysSerArgValAspHisCys

1396  GCACAGCAGGACCATGGCTGTGAGCAGCTGTGTCTGAACACGGAG
      AlaGlnGlnAspHisGlyCysGluGlnLeuCysLeuAsnThrGlu

1441  GATTCCTTCGTCTGCCAGTGCTCAGAAGGCTTCCTCATCAACGAG
      AspSerPheValCysGlnCysSerGluGlyPheLeuIleAsnGlu
```

Fig. 4 (continued)

```
1486  GACCTCAAGACCTGCTCCCGGGTGGATTACTGCCTGCTGAGTGAC
      AspLeuLysThrCysSerArgValAspTyrCysLeuLeuSerAsp

1531  CATGGTTGTGAATACTCCTGTGTCAACATGGACAGATCCTTTGCC
      HisGlyCysGluTyrSerCysValAsnMetAspArgSerPheAla

1576  TGTCAGTGTCCTGAGGGACACGTGCTCCGCAGCGATGGGAAGACG
      CysGlnCysProGluGlyHisValLeuArgSerAspGlyLysThr

1621  TGTGCAAAATTGGACTCTTGTGCTCTGGGGGACCACGGTTGTGAA
      CysAlaLysLeuAspSerCysAlaLeuGlyAspHisGlyCysGlu

1666  CATTCGTGTGTAAGCAGTGAAGATTCGTTTGTGTGCCAGTGCTTT
      HisSerCysValSerSerGluAspSerPheValCysGlnCysPhe

1711  GAAGGTTATATACTCCGTGAAGATGGAAAAACCTGCAGAAGGAAA
      GluGlyTyrIleLeuArgGluAspGlyLysThrCysArgArgLys

1756  GATGTCTGCCAAGCTATAGACCATGGCTGTGAACACATTTGTGTG
      AspValCysGlnAlaIleAspHisGlyCysGluHisIleCysVal

1801  AACAGTGACGACTCATACACGTGCGAGTGCTTGGAGGGATTCCGG
      AsnSerAspAspSerTyrThrCysGluCysLeuGluGlyPheArg

1846  CTCACTGAGGATGGGAAACGCTGCCGAATTTCCTCAGGGAAGGAT
      LeuThrGluAspGlyLysArgCysArgIleSerSerGlyLysAsp

1891  GTCTGCAAATCAACCCACCATGGCTGCGAACACATTTGTGTTAAT
      ValCysLysSerThrHisHisGlyCysGluHisIleCysValAsn

1936  AATGGGAATTCCTACATCTGCAAATGCTCAGAGGGATTTGTTCTA
      AsnGlyAsnSerTyrIleCysLysCysSerGluGlyPheValLeu

1981  GCTGAGGACGGAAGACGGTGCAAGAAATGCACTGAAGGCCCAATT
      AlaGluAspGlyArgArgCysLysLysCysThrGluGlyProIle

2026  GACCTGGTCTTTGTGATCGATGGATCCAAGAGTCTTGGAGAAGAG
      AspLeuValPheValIleAspGlySerLysSerLeuGlyGluGlu

2071  AATTTTGAGGTCGTGAAGCAGTTTGTCACTGGAATTATAGATTCC
      AsnPheGluValValLysGlnPheValThrGlyIleIleAspSer

2116  TTGACAATTTCCCCCAAAGCCGCTCGAGTGGGGCTGCTCCAGTAT
      LeuThrIleSerProLysAlaAlaArgValGlyLeuLeuGlnTyr

2161  TCCACACAGGTCCACACAGAGTTCACTCTGAGAAACTTCAACTCA
      SerThrGlnValHisThrGluPheThrLeuArgAsnPheAsnSer

2206  GCCAAAGACATGAAAAAGCCGTGGCCCACATGAAATACATGGGA
      AlaLysAspMetLysLysAlaValAlaHisMetLysTyrMetGly
```

Fig. 4 (continued)

```
2251  AAGGGCTCTATGACTGGGCTGGCCCTGAAACACATGTTTGAGAGA
      LysGlySerMetThrGlyLeuAlaLeuLysHisMetPheGluArg

2296  AGTTTTACCCAAGGAGAAGGGGCCAGGCCCCTTTTCCACAAGGGT
      SerPheThrGlnGlyGluGlyAlaArgProLeuPheHisLysGly

2341  GCCCAGAGCAGCCATTGTGTTCACCGACGGACGGGCTCAGGATGA
      AlaGlnSerSerHisCysValHisArgArgThrGlySerGly

2386  CGTCTCCGAGTGGGCCAGTAAAGCCAAGGCCAATGGTATCACTAT
2431  GTATGCTGTTGGGGTAGGAAAAGCCATTGAGGAGGAACTACAAGA
2476  GATTGCCTCTGAGCCCACAAACAAGCATCTCTTCTATGCCGAAGA
2521  CTTCAGCACAATGGATGAGATAAGTGAAAAACTCAAGAAAGGCAT
2566  CTGTGAAGCTCTAGAAGACTCCGATGGAAGACAGGACTCTCCAGC
2611  AGGGGAACTGCCAAAAACGGTCCAACAGCCAACAGAATCTGAGCC
2656  AGTCACCATAAATATCCAAGACCTACTTTCCTGTTCTAATTTTGC
2701  AGTGCAACACAGATATCTGTTTGAAGAAGACAATCTTTTACGGTC
2746  TACACAAAGCTTTCCCATTCAACAAAACCTTCAGGAAGCCCTTT
2791  GGAAGAAAACACGATCAATGCAAATGTGAAAACCTTATAATGTT
2836  CCAGAACCTTGCAAACGAAGAAGTAAGAAAATTTACACAGCGCTT
2881  AGAAGAAATGACACAGAGAATGGAAGCCCTGGAAAATCGCCTGAG
2926  ATACAGATGAAGATTAGAAATCGCGACACATTTGTAGTCATTGTA
2971  TCACGGATTACAATGAACGCAGTGCAGAGCCCCAAAGCTCAGGCT
3016  ATTGTTAAATC
```

Fig. 4 (continued)

```
  1  GGTAGCCGACGCGCCGGCCGGCGCGTGACCTTGCCCCTCTTGCTC

46  GCCTTGAAAATGGAAAAGATGCTCGCAGGCTGCTTTCTGCTGATC
                  MetGluLysMetLeuAlaGlyCysPheLeuLeuIle

91  CTCGGACAGATCGTCCTCCTCCCTGCGAGGCCAGGGAGCGGTCA
     LeuGlyGlnIleValLeuLeuProCysGluAlaArgGluArgSer

136  CGTGGGAGGTCCATCTCTAGGGGCAGACACGCTCGGACCCACCCG
     ArgGlyArgSerIleSerArgGlyArgHisAlaArgThrHisPro

181  CAGACGGCCCTTCTGGAGAGTTCCTGTGAGAACAAGCGGGCAGAC
     GlnThrAlaLeuLeuGluSerSerCysGluAsnLysArgAlaAsp

226  CTGGTTTTCATCATTGACAGCTCTCGCAGTGTCAACACCCATGAC
     LeuValPheIleIleAspSerSerArgSerValAsnThrHisAsp

271  TATGCAAAGGTCAAGGAGTTCATCGTGGACATCTTGCAATTCTTG
     TyrAlaLysValLysGluPheIleValAspIleLeuGlnPheLeu

316  GACATTGGTCCTGATGTCACCCGAGTGGGCCTGCTCCAATATGGC
     AspIleGlyProAspValThrArgValGlyLeuLeuGlnTyrGly

361  AGCACTGTCAAGAATGAGTTCTCCCTCAAGACCTTCAAGAGGAAG
     SerThrValLysAsnGluPheSerLeuLysThrPheLysArgLys

406  TCCGAGGTGGAGCGTGCTGTCAAGAGGATGCGGCATCTGTCCACG
     SerGluValGluArgAlaValLysArgMetArgHisLeuSerThr

451  GGCACCATGACTGGGCTGGCCATCCAGTATGCCCTGAACATCGCA
     GlyThrMetThrGlyLeuAlaIleGlnTyrAlaLeuAsnIleAla

496  TTCTCAGAAGCAGAGGGGGCCCGGCCCCTGAGGGAGAATGTGCCA
     PheSerGluAlaGluGlyAlaArgProLeuArgGluAsnValPro

541  CGGGTCATAATGATCGTGACGGATGGGAGACCTCAGGACTCCGTG
     ArgValIleMetIleValThrAspGlyArgProGlnAspSerVal

586  GCCGAGGTGGCTGCTAAGGCACGGGACACGGGCATCCTAATCTTT
     AlaGluValAlaAlaLysAlaArgAspThrGlyIleLeuIlePhe

631  GCCATTGGTGTGGGCCAGGTAGACTTCAACACCTTGAAGTCCATT
     AlaIleGlyValGlyGlnValAspPheAsnThrLeuLysSerIle

676  GGGAGTGAGCCCCATGAGGACCATGTCTTCCTTGTGGCCAATTTC
     GlySerGluProHisGluAspHisValPheLeuValAlaAsnPhe

721  AGCCAGATTGAGACGCTGACCTCCGTGTTCCAGAAGAAGTTGTGC
     SerGlnIleGluThrLeuThrSerValPheGlnLysLysLeuCys
```

Fig. 5

766 ACGGCCCACATGTGCAGCACCCTGGAGCATAACTGTGCCCACTTC
    ThrAlaHisMetCysSerThrLeuGluHisAsnCysAlaHisPhe

811 TGCATCAACATCCCTGGCTCATACGTCTGCAGGTGCAAACAAGGC
    CysIleAsnIleProGlySerTyrValCysArgCysLysGlnGly

856 TACATTCTCAACTCGGATCAGACGACTTGCAGAATCCAGGATCTG
    TyrIleLeuAsnSerAspGlnThrThrCysArgIleGlnAspLeu

901 TGTGCCATGGAGGACCACAACTGTGAGCAGCTCTGTGTGAATGTG
    CysAlaMetGluAspHisAsnCysGluGlnLeuCysValAsnVal

946 CCGGGCTCCTTCGTCTGCGAGTGCTACAGTGGCTACGCCCTGGCT
    ProGlySerPheValCysGluCysTyrSerGlyTyrAlaLeuAla

991 GAGGATGGGAAGAGGTGTGTGGCTGTGGACTACTGTGCCTCAGAA
    GluAspGlyLysArgCysValAlaValAspTyrCysAlaSerGlu

1036 AACCACGGATGTGAACATGAGTGTGTAAATGCTGATGGCTCCTAC
     AsnHisGlyCysGluHisGluCysValAsnAlaAspGlySerTyr

1081 CTTTGCCAGTGCCATGAAGGATTTGCTCTTAACCCAGATGAAAAA
     LeuCysGlnCysHisGluGlyPheAlaLeuAsnProAspGluLys

1126 ACGTGCACAAAGATAGACTACTGTGCCTCATCTAATCATGGATGT
     ThrCysThrLysIleAspTyrCysAlaSerSerAsnHisGlyCys

1171 CAGTACGAGTGTGTTAACACAGATGATTCCTATTCCTGCCACTGC
     GlnTyrGluCysValAsnThrAspAspSerTyrSerCysHisCys

1216 CTGAAAGGCTTTACCCTGAATCCAGATAAGAAAACCTGCAGAAGG
     LeuLysGlyPheThrLeuAsnProAspLysLysThrCysArgArg

1261 ATCAACTACTGTGCACTGAACAAACCGGGCTGTGAGCATGAGTGC
     IleAsnTyrCysAlaLeuAsnLysProGlyCysGluHisGluCys

1306 GTCAACATGGAGGAGAGCTACTACTGCCGCTGCCACCGTGGCTAC
     ValAsnMetGluGluSerTyrTyrCysArgCysHisArgGlyTyr

1351 ACTCTGGACCCCAATGGCAAACCCTGCAGCCGAGTGGACCACTGT
     ThrLeuAspProAsnGlyLysProCysSerArgValAspHisCys

1396 GCACAGCAGGACCATGGCTGTGAGCAGCTGTGTCTGAACACGGAG
     AlaGlnGlnAspHisGlyCysGluGlnLeuCysLeuAsnThrGlu

1441 GATTCCTTCGTCTGCCAGTGCTCAGAAGGCTTCCTCATCAACGAG
     AspSerPheValCysGlnCysSerGluGlyPheLeuIleAsnGlu

1486 GACCTCAAGACCTGCTCCCGGGTGGATTACTGCCTGCTGAGTGAC
     AspLeuLysThrCysSerArgValAspTyrCysLeuLeuSerAsp

Fig. 5 (continued)

```
1531  CATGGTTGTGAATACTCCTGTGTCAACATGGACAGATCCTTTGCC
      HisGlyCysGluTyrSerCysValAsnMetAspArgSerPheAla

1576  TGTCAGTGTCCTGAGGGACACGTGCTCCGCAGCGATGGGAAGACG
      CysGlnCysProGluGlyHisValLeuArgSerAspGlyLysThr

1621  TGTGCAAAATTGGACTCTTGTGCTCTGGGGGACCACGGTTGTGAA
      CysAlaLysLeuAspSerCysAlaLeuGlyAspHisGlyCysGlu

1666  CATTCGTGTGTAAGCAGTGAAGATTCGTTTGTGTGCCAGTGCTTT
      HisSerCysValSerSerGluAspSerPheValCysGlnCysPhe

1711  GAAGGTTATATACTCCGTGAAGATGGAAAAACCTGCAGAAGGAAA
      GluGlyTyrIleLeuArgGluAspGlyLysThrCysArgArgLys

1756  GATGTCTGCCAAGCTATAGACCATGGCTGTGAACACATTTGTGTG
      AspValCysGlnAlaIleAspHisGlyCysGluHisIleCysVal

1801  AACAGTGACGACTCATACACGTGCGAGTGCTTGGAGGGATTCCGG
      AsnSerAspAspSerTyrThrCysGluCysLeuGluGlyPheArg

1846  CTCACTGAGGATGGGAAACGCTGCCGAATTTCCTCAGGGAAGGAT
      LeuThrGluAspGlyLysArgCysArgIleSerSerGlyLysAsp

1891  GTCTGCAAATCAACCCACCATGGCTGCGAACACATTTGTGTTAAT
      ValCysLysSerThrHisHisGlyCysGluHisIleCysValAsn

1936  AATGGGAATTCCTACATCTGCAAATGCTCAGAGGGATTTGTTCTA
      AsnGlyAsnSerTyrIleCysLysCysSerGluGlyPheValLeu

1981  GCTGAGGACGGAAGACGGTGCAAGAAATGCACTGAAGGCCCAATT
      AlaGluAspGlyArgArgCysLysLysCysThrGluGlyProIle

2026  GACCTGGTCTTTGTGATCGATGGATCCAAGAGTCTTGGAGAAGAG
      AspLeuValPheValIleAspGlySerLysSerLeuGlyGluGlu

2071  AATTTTGAGGTCGTGAAGCAGTTTGTCACTGGAATTATAGATTCC
      AsnPheGluValValLysGlnPheValThrGlyIleIleAspSer

2116  TTGACAATTTCCCCCAAAGCCGCTCGAGTGGGGCTGCTCCAGTAT
      LeuThrIleSerProLysAlaAlaArgValGlyLeuLeuGlnTyr

2161  TCCACACAGGTCCACACAGAGTTCACTCTGAGAAACTTCAACTCA
      SerThrGlnValHisThrGluPheThrLeuArgAsnPheAsnSer

2206  GCCAAGACATGAAAAAGCCGTGGCCCACATGAAATACATGGGA
      AlaLysAspMetLysLysAlaValAlaHisMetLysTyrMetGly
```

Fig. 5 (continued)

```
2251  AAGGGCTCTATGACTGGGCTGGCCCTGAAACACATGTTTGAGAGA
      LysGlySerMetThrGlyLeuAlaLeuLysHisMetPheGluArg

2296  AGTTTTACCCAAGGAGAAGGGGCCAGGCCCTTTTCCACAAGGGTG
      SerPheThrGlnGlyGluGlyAlaArgProPheSerThrArgVal

2341  CCCAGAGCAGCCATTGTGTTCACCGACGGACGGGCTCAGGATGAC
      ProArgAlaAlaIleValPheThrAspGlyArgAlaGlnAspAsp

2386  GTCTCCGAGTGGGCCAGTAAAGCCAAGGCCAATGGTATCACTATG
      ValSerGluTrpAlaSerLysAlaLysAlaAsnGlyIleThrMet

2431  TATGCTGTTGGGGTAGGAAAAGCCATTGAGGAGGAACTACAAGAG
      TyrAlaValGlyValGlyLysAlaIleGluGluGluLeuGlnGlu

2476  ATTGCCTCTGAGCCCACAAACAAGCATCTCTTCTATGCCGAAGAC
      IleAlaSerGluProThrAsnLysHisLeuPheTyrAlaGluAsp

2521  TTCAGCACAATGGATGAGATAAGTGAAAAACTCAAGAAAGGCATC
      PheSerThrMetAspGluIleSerGluLysLeuLysLysGlyIle

2566  TGTGAAGCTCTAGAAGACTCCGATGGAAGACAGGACTCTCCAGCA
      CysGluAlaLeuGluAspSerAspGlyArgGlnAspSerProAla

2611  GGGGAACTGCCAAAAACGGTCCAACAGCCAACAGAATCTGAGCCA
      GlyGluLeuProLysThrValGlnGlnProThrGluSerGluPro

2656  GTCACCATAAATATCCAAGACCTACTTTCCTGTTCTAATTTTGCA
      ValThrIleAsnIleGlnAspLeuLeuSerCysSerAsnPheAla

2701  GTGCAACACAGATATCTGTTTGAAGAAGACAATCTTTTACGGTCT
      ValGlnHisArgTyrLeuPheGluGluAspAsnLeuLeuArgSer

2746  ACACAAAAGCTTTCCCATTCAACAAAACCTTCAGGAAGCCCTTTG
      ThrGlnLysLeuSerHisSerThrLysProSerGlySerProLeu

2791  GAAGAAAAACACGATCAATGCAAATGTGAAACCTTATAATGTTC
      GluGluLysHisAspGlnCysLysCysGluAsnLeuIleMetPhe

2836  CAGAACCTTGCAAACGAAGAAGTAAGAAAATTAACACAGCGCTTA
      GlnAsnLeuAlaAsnGluGluValArgLysLeuThrGlnArgLeu

2881  GAAGAAATGACACAGAGAATGGAAGCCCTGGAAAATCGCCTGAGA
      GluGluMetThrGlnArgMetGluAlaLeuGluAsnArgLeuArg

2926  TACAGATGAAGATTAGAAATCGCGACACATTTGTAGTCATTGTAT
      TyrArg
```

Fig. 5 (continued)

```
2971  CACGGATTACAATGAACGCAGTGCAGAGCCCCAAAGCTCAGGCTA
3016  TTGTTAAATCAATAATGTTGTGAAGTAAAACAATCAGTACTGAGA
3061  AACCTGGTTTGCCACAGAACAAAGACAAGAAGTATACACTAACTT
3106  GTATAAATTTATCTAGGAAAAAAATCCTTCAGAATTCTAAGATGA
3151  ATTTACCAGGTGAGAATGAATAAGCTATGCAAGGTATTTTGTAAT
3196  ATACTGTGGACACAACTTGCTTCTGCCTCATCCTGCCTTAGTGTG
3241  CAATCTCATTTGACTATACGATAAAGTTTGCACAGTCTTACTTCT
3286  GTAGAACACTGGCCATAGGAAATGCTGTTTTTTTGTACTGGACTT
3331  TACCTTGATATATGTATATGGATGTATGCATAAAATCATAGGACA
3376  TATGTACTTGTGGAACAAGTTGGATTTTTTATACAATATTAAAAT
3421  TCACCACTTCAGAGAAAAGTAAAAAAA
```

Fig. 5 (continued)

```
  1 CGGCCCTTCTCACACTCCTGCCCTGCTGATGTGGAACGGGGTTTG
 46 GGGTTCTGCAGGGCTATTGTCTGCGCTGGGGAAGGGGACAGGCCG
 91 GGACCGGGACCTCCGCTCGCAGCCGGCCGCACCAGCAGGACAGCT

136 GGCCTGAAGCTCAGAGCCGGGGCGTGCGCCATGGCCCCACACTGG
                                   MetAlaProHisTrp

181 GCTGTCTGGCTGCTGGCAGCAAGGCTGTGGGGCCTGGGCATTGGG
    AlaValTrpLeuLeuAlaAlaArgLeuTrpGlyLeuGlyIleGly

226 GCTGAGGTGTGGTGGAACCTTGTGCCGCGTAAGACAGTGTCTTCT
    AlaGluValTrpTrpAsnLeuValProArgLysThrValSerSer

271 GGGGAGCTGGCCACGGTAGTACGGCGGTTCTCCCAGACCGGCATC
    GlyGluLeuAlaThrValValArgArgPheSerGlnThrGlyIle

316 CAGGACTTCCTGACACTGACGCTGACGGAGCCCACTGGGCTTCTG
    GlnAspPheLeuThrLeuThrLeuThrGluProThrGlyLeuLeu

361 TACGTGGGCGCCCGAGAGGCCCTGTTTGCCTTCAGCATGGAGGCC
    TyrValGlyAlaArgGluAlaLeuPheAlaPheSerMetGluAla

406 CTGGAGCTGCAAGGAGCGATCTCCTGGGAGGCCCCCGTGGAGAAG
    LeuGluLeuGlnGlyAlaIleSerTrpGluAlaProValGluLys

451 AAGACTGAGTGTATCCAGAAAGGGAAGAACAACCAGACCGAGTGC
    LysThrGluCysIleGlnLysGlyLysAsnAsnGlnThrGluCys

496 TTCAACTTCATCCGCTTCCTGCAGCCCTACAATGCCTCCCACCTG
    PheAsnPheIleArgPheLeuGlnProTyrAsnAlaSerHisLeu

541 TACGTCTGTGGCACCTACGCCTTCCAGCCCAAGTGCACCTACGTC
    TyrValCysGlyThrTyrAlaPheGlnProLysCysThrTyrVal

586 AACATGCTCACCTTCACTTTGGAGCATGGAGAGTTTGAAGATGGG
    AsnMetLeuThrPheThrLeuGluHisGlyGluPheGluAspGly

631 AAGGGCAAGTGTCCCTATGACCCAGCTAAGGGCCATGCTGGCCTT
    LysGlyLysCysProTyrAspProAlaLysGlyHisAlaGlyLeu

676 CTTGTGGATGGTGAGCTGTACTCGGCCACACTCAACAACTTCCTG
    LeuValAspGlyGluLeuTyrSerAlaThrLeuAsnAsnPheLeu

721 GGCACGGAACCCATTATCCTGCGTAACATGGGGCCCCACCACTCC
    GlyThrGluProIleIleLeuArgAsnMetGlyProHisHisSer
```

Fig. 6

```
766  ATGAAGACAGAGTACCTGGCCTTTTGGCTCAACGAACCTCACTTT
     MetLysThrGluTyrLeuAlaPheTrpLeuAsnGluProHisPhe

811  GTAGGCTCTGCCTATGTACCTGAGAGGGTGGGCCTGCTGTGGACA
     ValGlySerAlaTyrValProGluArgValGlyLeuLeuTrpThr

856  ATGGCATACTCTCTTCCAGCCCTAGGAGGAGGGCTCCTAACAGTG
     MetAlaTyrSerLeuProAlaLeuGlyGlyGlyLeuLeuThrVal

901  TAACTTATTGTGTCCCCGCGTATTTATTTGTTGTAAATATTTGAG
946  TATTTTTATATTGACAAATAAA
```

Fig. 6 (continued)

```
  1  GGCACCAGGCCTTCCGGAGAGACGCAGTCGGCTGCCACCCCGGGA
                                                 M

46  TGGGTCGCTGGTGCCAGACCGTCGCGCGCGGGCAGCGCCCCGGA
     etGlyArgTrpCysGlnThrValAlaArgGlyGlnArgProArgT

91  CGTCTGCCCCTCCCGCGCCGGTGCCCTGCTGCTGCTGCTTCTGT
     hrSerAlaProSerArgAlaGlyAlaLeuLeuLeuLeuLeuLeuL

136  TGCTGAGGTCTGCAGGTTGCTGGGGCGCAGGGGAAGCCCCGGGGG
     euLeuArgSerAlaGlyCysTrpGlyAlaGlyGluAlaProGlyA

181  CGCTGTCCACTGCTGATCCCGCCGACCAGAGCGTCCAGTGTGTCC
     laLeuSerThrAlaAspProAlaAspGlnSerValGlnCysValP

226  CCAAGGCCACCTGTCCTTCCAGCCGGCCTCGCCTTCTCTGGCAGA
     roLysAlaThrCysProSerSerArgProArgLeuLeuTrpGlnT

271  CCCCGACCACCCAGACACTGCCCTCGACCACCATGGAGACCCAAT
     hrProThrThrGlnThrLeuProSerThrThrMetGluThrGlnP

316  TCCCAGTTTCTGAAGGCAAAGTCGACCCATACCGCTCCTGTGGCT
     heProValSerGluGlyLysValAspProTyrArgSerCysGlyP

361  TTTCCTACGAGCAGGACCCCACCCTCAGGGACCCAGAAGCCGTGG
     heSerTyrGluGlnAspProThrLeuArgAspProGluAlaValA

406  CTCGGCGGTGGCCCTGGATGGTCAGCGTGCGGGCCAATGGCACAC
     laArgArgTrpProTrpMetValSerValArgAlaAsnGlyThrH

451  ACATCTGTGCCGGCACCATCATTGCCTCCCAGTGGGTGCTGACTG
     isIleCysAlaGlyThrIleIleAlaSerGlnTrpValLeuThrV

496  TGGCCCACTGCCTGATCTGGCGTGATGTTATCTACTCAGTGAGGG
     alAlaHisCysLeuIleTrpArgAspValIleTyrSerValArgV

541  TGGGGAGTCCGTGGATTGACCAGATGACGCAGACCGCCTCCGATG
     alGlySerProTrpIleAspGlnMetThrGlnThrAlaSerAspV

586  TCCCGGTGCTCCAGGTCATCATGCATAGCAGGTACCGGGCCCAGC
     alProValLeuGlnValIleMetHisSerArgTyrArgAlaGlnA

631  GGTTCTGGTCCTGGGTGGGCCAGGCCAACGACATCGGCCTCCTCA
     rgPheTrpSerTrpValGlyGlnAlaAsnAspIleGlyLeuLeuL

676  AGCTCAAGCAGGAACTCAAGTACAGCAATTACGTGCGGCCCATCT
     ysLeuLysGlnGluLeuLysTyrSerAsnTyrValArgProIleC
```

Fig. 7

```
 721  GCCTGCCTGGCACGGACTATGTGTTGAAGGACCATTCCCGCTGCA
      ysLeuProGlyThrAspTyrValLeuLysAspHisSerArgCysT

766  CTGTGACGGGCTGGGGACTTTCCAAGGCTGACGGCATGTGGCCTC
      hrValThrGlyTrpGlyLeuSerLysAlaAspGlyMetTrpProG

811  AGTTCCGGACCATTCAGGAGAAGGAAGTCATCATCCTGAACAACA
      lnPheArgThrIleGlnGluLysGluValIleIleLeuAsnAsnL

856  AAGAGTGTGACAATTTCTACCACAACTTCACCAAAATCCCCACTC
      ysGluCysAspAsnPheTyrHisAsnPheThrLysIleProThrL

901  TGGTTCAGATCATCAAGTCCCAGATGATGTGTGCGGAGGACACCC
      euValGlnIleIleLysSerGlnMetMetCysAlaGluAspThrH

946  ACAGGGAGAAGTTCTGCTATGAGCTAACTGGAGAGCCCTTGGTCT
      isArgGluLysPheCysTyrGluLeuThrGlyGluProLeuValC

991  GCTCCATGGAGGGCACGTGGTACCTGGTGGGATTGGTGAGCTGGG
      ysSerMetGluGlyThrTrpTyrLeuValGlyLeuValSerTrpG

1036  GTGCAGGCTGCCAGAAGAGCGAGGCCCCACCCATCTACCTACAGG
      lyAlaGlyCysGlnLysSerGluAlaProProIleTyrLeuGlnV

1081  TCTCCTCCTACCAACACTGGATCTGGGACTGCCTCAACGGGCAGG
      alSerSerTyrGlnHisTrpIleTrpAspCysLeuAsnGlyGlnA

1126  CCCTGGCCCTGCCAGCCCCATCCAGGACCCTGCTCCTGGCACTCC
      laLeuAlaLeuProAlaProSerArgThrLeuLeuLeuAlaLeuP

1171  CACTGCCCCTCAGCCTCCTTGCTGCCCTCTGACTCTGTGTGCCCT
      roLeuProLeuSerLeuLeuAlaAlaLeu

1216  CCCTCACTTGTGGCCCCCCTTGCCTCCGTGCCCAGGTTGCTGTG
1261  GGTGCAGCTGTCACAGCCCTGAGAGTCAGGGTGGAGATGAGGTGC
1306  TCAATTAAACATTACTGTTTTCCATGTAAAAAAAAAAAAAAAAAA
1351  AAAAAAAAA
```

Fig. 7 (continued)

```
CACCCCTCTGCCTGCCCCAGCCCGCCCATCGCTTCCCCTTTGGAGCCTCCTGCTGGGCCACTGGCTGGGATCAGGACACC
         81
AGTGATGGTAAGTGCTGGCCCAGACTGAAGCTCGGAGAGGCACTCTGCTTGCCCAGCGTCACAGTCTTAGCTCCCAACTG
        161
TCCTGGCTTCCAGTCTCCCTTGCTTCCCAGATCCCAGACTCTAGCCCCAGCCCCGTCTCTTTCACCAGCTCCTGGGACCC
        241
TACGCAATCTGCGCCTGCGTCTCATCAGTCGCCCCACATGTAACTGTATCTACAACCAGCTGCACCAGCGACACCTGTCC
        321
AACCCGGCCCGGCCTGGGATGCTATGTGGGGGCCCCCAGCCTGGGGTGCAGGGCCCCTGTCAGGTCTGATAGGGAGAAGA
        401
GAAGGAGCAGAAGGGGAGGGGCCTAACCCTGGGCTGGGGGTTGGACTCACAGGACTGGGGGAAAGAGCTGCAATCAGAGG
        481
GTGTCTGCCATAGCTGGGCTCAGGCATCTGTCCTTGGCTTTGTTGCCTGGCTCCAGGGAGATTCCGGGGGCCCTGTGCTG
        561
TGCCTCGAGCCTGACGGACACTGGGTTCAGGCTGGCATCATCAGCTTTGCATCAAGCTGTGCCCAGGAGGACGCTCCTGT
        641
GCTGCTGACCAACACAGCTGCTCACAGTTCCTGGCTGCAGGCTCGAGTTCAGGGGGCAGCTTTCCTGGCCCAGAGCCCAG
        721
AGACCCCGGAGATGAGTGATGAGGACAGCTGTGTAGCCTGTGGATCCTTGAGGACAGCAGGTCCCCAGGCAGGAGCACCC
         MetSerAspGluAspSerCysValAlaCysGlySerLeuArgThrAlaGlyProGlnAlaGlyAlaPro
        801
TCCCCATGGCCCTGGGAGGCCAGGCTGATGCACCAGGGACAGCTGGCCTGTGGCGGAGCCCTGGTGTCAGAGGAGGCGGT
SerProTrpProTrpGluAlaArgLeuMetHisGlnGlyGlnLeuAlaCysGlyGlyAlaLeuValSerGluGluAlaVa
        881
GCTAACTGCTGCCCACTGCTTCATTGGGCGCCAGGCCCCAGAGGAATGGAGCGTAGGGCTGGGGACCAGACCGGAGGAGT
lLeuThrAlaAlaHisCysPheIleGlyArgGlnAlaProGluGluTrpSerValGlyLeuGlyThrArgProGluGluT
        961
GGGGCCTGAAGCAGCTCATCCTGCATGGAGCCTACACCCACCCTGAGGGGGGCTACGACATGGCCCTCCTGCTGCTGGCC
rpGlyLeuLysGlnLeuIleLeuHisGlyAlaTyrThrHisProGluGlyGlyTyrAspMetAlaLeuLeuLeuLeuAla
       1041
CAGCCTGTGACACTGGGAGCCAGCCTGCGGCCCCTCTGCCTGCCCTATGCTGACCACCACCTGCCTGATGGGGAGCGTGG
GlnProValThrLeuGlyAlaSerLeuArgProLeuCysLeuProTyrAlaAspHisHisLeuProAspGlyGluArgGl
       1121
CTGGGTTCTGGGACGGGCCCGCCCAGGAGCAGGCATCAGCTCCTCCAGACAGTGCCCGTGACCCTCCTGGGGCCTAGGG
yTrpValLeuGlyArgAlaArgProGlyAlaGlyIleSerSerLeuGlnThrValProValThrLeuLeuGlyProArgA
       1201
CCTGCAGCCGGCTGCATGCAGCTCCTGGGGGTGATGGCAGCCCTATTCTGCCGGGGATGGTGTGTACCAGTGCTGTGGGT
laCysSerArgLeuHisAlaAlaProGlyGlyAspGlySerProIleLeuProGlyMetValCysThrSerAlaValGly
       1281
GAGCTGCCCAGCTGTGAGGTGAGCCCCAGGCCCCCACACCTTACCTAACAGGCCCCTGGCATCCCCTCACCCAATAGCTC
GluLeuProSerCysGluValSerProArgProProHisLeuThr
       1361
AAGAACGGACCTTCCAGGCTTGGCCTCTGGACCCACCTCCCACCTGAAGCTAAGCCTTTTTGCCAATTAGCCCCCAAACA
       1441
GCCAG
```

Fig. 8

```
  1  CTTAACAGCCACTTGTTTCATCCCACCTGGGCATTAGGTTGACTT

46  CAAAGATGCCTCAGTTACTGCAAAACATTAATGGGATCATCGAGG
        MetProGlnLeuLeuGlnAsnIleAsnGlyIleIleGluA

91  CCTTCAGGCGCTATGCAAGGACGGAGGGCAACTGCACAGCGCTCA
     laPheArgArgTyrAlaArgThrGluGlyAsnCysThrAlaLeuT

136  CCCGAGGGGAGCTGAAAAGACTCTTGGAGCAAGAGTTTGCCGATG
     hrArgGlyGluLeuLysArgLeuLeuGluGlnGluPheAlaAspV

181  TGATTGTGAAACCCCACGATCCAGCAACTGTGGATGAGGTCCTGC
     alIleValLysProHisAspProAlaThrValAspGluValLeuA

226  GTCTGCTGGATGAAGACCACACAGGGACTGTGGAATTCAAGGAAT
     rgLeuLeuAspGluAspHisThrGlyThrValGluPheLysGluP

271  TCCTGGTCTTAGTGTTTAAAGTTGCCCAGGCCTGTTTCAAGACAC
     heLeuValLeuValPheLysValAlaGlnAlaCysPheLysThrL

316  TGAGCGAGAGTGCTGAGGGAGCCTGCGGCTCTCAAGAGTCTGGAA
     euSerGluSerAlaGluGlyAlaCysGlySerGlnGluSerGlyS

361  GCCTCCACTCTGGGGCCTCGCAGGAGCTGGGCGAAGGACAGAGAA
     erLeuHisSerGlyAlaSerGlnGluLeuGlyGluGlyGlnArgS

406  GTGGCACTGAAGTGGGAAGGGCGGGGAAAGGGCAGCATTATGAGG
     erGlyThrGluValGlyArgAlaGlyLysGlyGlnHisTyrGluG

451  GGAGCAGCCACAGACAGAGCCAGCAGGGTTCCAGAGGGCAGAACA
     lySerSerHisArgGlnSerGlnGlnGlySerArgGlyGlnAsnA

496  GGCCTGGGGTTCAGACCCAGGGTCAGGCCACTGGCTCTGCGTGGG
     rgProGlyValGlnThrGlnGlyGlnAlaThrGlySerAlaTrpV

541  TCAGCAGCTATGACAGGCAAGCTGAGTCCCAGAGCCAGGAAAGAA
     alSerSerTyrAspArgGlnAlaGluSerGlnSerGlnGluArgI

586  TAAGCCCGCAGATACAACTCTCTGGGCAGACAGAGCAGACCCAGA
     leSerProGlnIleGlnLeuSerGlyGlnThrGluGlnThrGlnL

631  AAGCTGGAGAAGGCAAGAGGAATCAGACAACAGAGATGAGGCCAG
     ysAlaGlyGluGlyLysArgAsnGlnThrThrGluMetArgProG

676  AGAGACAGCCACAGACCAGGGAACAGGACAGAGCCCACCAGACAG
     luArgGlnProGlnThrArgGluGlnAspArgAlaHisGlnThrG
```

Fig. 9

```
721   GTGAGACTGTGACTGGATCTGGAACTCAGACCCAGGCAGGTGCCA
      lyGluThrValThrGlySerGlyThrGlnThrGlnAlaGlyAlaT

766   CCCAGACTGTGGAGCAGGACAGCAGCCACCAGACAGGAAGCACCA
      hrGlnThrValGluGlnAspSerSerHisGlnThrGlySerThrS

811   GCACCCAGACACAGGAGTCCACCAATGGCCAGAACAGAGGGACTG
      erThrGlnThrGlnGluSerThrAsnGlyGlnAsnArgGlyThrG

856   AGATCCACGGTCAAGGCAGGAGCCAGACCAGCCAGGCTGTGACAG
      luIleHisGlyGlnGlyArgSerGlnThrSerGlnAlaValThrG

901   GAGGACACACTCAGATACAGGCAGGGTCACACACCGAGACTGTGG
      lyGlyHisThrGlnIleGlnAlaGlySerHisThrGluThrValG

946   AGCAGGACAGAAGCCAAACTGTAAGCCACGGAGGGGCTAGAGAAC
      luGlnAspArgSerGlnThrValSerHisGlyGlyAlaArgGluG

991   AGGGACAGACCCAGACGCAGCCAGGCAGTGGTCAAAGATGGATGC
      lnGlyGlnThrGlnThrGlnProGlySerGlyGlnArgTrpMetG

1036  AAGTGAGCAACCCTGAGGCAGGAGAGACAGTACCGGGAGGACAGG
      lnValSerAsnProGluAlaGlyGluThrValProGlyGlyGlnA

1081  CCCAGACTGGGGCAAGCACTGAGTCAGGAAGGCAGGAGTGGAGCA
      laGlnThrGlyAlaSerThrGluSerGlyArgGlnGluTrpSerS

1126  GCACTCACCCAAGGCGCTGTGTGACAGAAGGGCAGGGAGACAGAC
      erThrHisProArgArgCysValThrGluGlyGlnGlyAspArgG

1171  AGCCCACAGTGGTTGGTGAGGAATGGGTTGATGACCACTCAAGGG
      lnProThrValValGlyGluGluTrpValAspAspHisSerArgG

1216  AGACAGTGATCCTCAGGCTGGACCAGGGCAACTTGCATACCAGTG
      luThrValIleLeuArgLeuAspGlnGlyAsnLeuHisThrSerV

1261  TTTCCTCAGCACAGGGCCAGGATGCAGCCCAGTCAGAAGAGAAGC
      alSerSerAlaGlnGlyGlnAspAlaAlaGlnSerGluGluLysA

1306  GAGGCATCACAGCTAGAGAGCTGTATTCCTACTTGAGAAGCACCA
      rgGlyIleThrAlaArgGluLeuTyrSerTyrLeuArgSerThrL

1351  AGCCATGACTTCCCCGACTCCAATGTCCAGTACTGGAAGAAGACA
      ysPro

1396  GCTGGAGAGAGTTTGGCTTGTCCTGCATGGCCAATCCAGTGGGTG
1441  CATCCCTGGACATCAGCTCTTCATTATGCAGCTTCCCTTTTAGGT
1486  CTTTCTCAATGAGATAATTTCTGCAAGGAGCTTTCTATCCTGAAC
1531  TCTTCTTTCTTACCTGCTTTGCGGTGCAGACCCTCTCAGGAGCAG
1576  GAAGACTCAGAACAAGTCACCCCTT
```

Fig. 9 (continued)

1. 11618130.0.184_Cura_108
2. 11618130.0.27_Cura_56

11618130.0184_cura_108   MSDEDSCVACGSLRTAGPQAGAPSPWPWEARLMHQGLACGGALVSEEAVLTAAHCFIGR
11618130027_cura_56      MSDEDSCVACGSLRTAGPQAGAPSPWPWEARLMHQGLACGGALVSEEAVLTAAHCFNGR 11618130.0184_cura_108   QAPEEWSVGLGTRPEEWGLKQLILHGAYTHPEGGYDMALLLLAQPVTLGASLRPLCLPYA
11618130027_cura_56      QAPEEWSVGLGTRPEEWGLKQLILHGAYTHPEGGYDMALLLLAQPVTLGASLRALCLPYF 11618130.0184_cura_108   DHHLPDGERGWVLGRARPGAGISSLQTVPVTLLGPRACSRLHAAPGGDGSPILPGMVCTS
11618130027_cura_56      DHHLPDGERGWVLGRARPGAGISSLQTVPVTLLGPRACSRLHAAPGGDGSPILPGMVCTS 11618130.0184_cura_108   AVGELPSCEVSPRPPHLTHEVRGTWFLAGLHSFGDACQGPARPAVFTALPAYEDWVSSLDW
11618130027_cura_56      AVGELPSCEGLSGAPLVM----------------------------------------

11618130.0184_cura_108   ---------------------
11618130027_cura_56      QVYFAEEPEPEAEPGSCLANISQPTSC

Fig. 10

Sequences analyzed:
1. 14578444-0-47_Cura_56
2. 14578444-0-143Cura_56

| | |
|---|---|
| 14578444047_cura_56 | MEKMLAGCFLLILGQIVLLPCEARERSRGRSISRGRHARTHPQTALLESSCENKRADLVF |
| 14578444043_cura_56 | MEKMLAGCFLLILGQIVLLPAEARERSRGRSISRGRHARTHPQTALLESSCENKRADLVF |

| | |
|---|---|
| 14578444047_cura_56 | IIDSSRSVNTHDYAKVKEFIVDILQFLDIGPDVTRVGLLQYGSTVKNEFSLKTFKRKSEV |
| 14578444043_cura_56 | IIDSSRSVNTHDYAKVKEFIVDILQFLDIGPDVTRVGLLQYGSTVKNEFSLKTFKRKSEV |

| | |
|---|---|
| 14578444047_cura_56 | ERAVKRMRHLSTGTMTGLAIQYALNIAFSEAEGARPLRENVPRVIMIVTDGRPQDSVAEV |
| 14578444043_cura_56 | ERAVKRMRHLSTGTMTGLAIQYALNIAFSEAEGARPLRENVPRVIMIVTDGRPQDSVAEV |

| | |
|---|---|
| 14578444047_cura_56 | AAKARDTGILIFAIGVGQVDFNTLKSIGSEPHEDHVFLVANFSQIETLTSVFQKKLCTAH |
| 14578444043_cura_56 | AAKARDTGILIFAIGVGQVDFNTLKSIGSEPHEDHVFLVANFSQIETLTSVFQKKLCTAH |

| | |
|---|---|
| 14578444047_cura_56 | MCSTLEHNCAHFCINIPGSYVCRCKQGYILNSDQTTCRIQDLCAMEDHNCEQLCVNVPGS |
| 14578444043_cura_56 | MCSTLEHNCAHFCINIPGSYVCRCKQGYILNSDQTTCRIQDLCAMEDHNCEQLCVNVPGS |

| | |
|---|---|
| 14578444047_cura_56 | FVCECYSGYALAEDGKRCVAVDYCASENHGCEHECVNADGSYLCQCHEGFALNPDEKTCT |
| 14578444043_cura_56 | FVCECYSGYALAEDGKRCVAVDYCASENHGCEHECVNADGSYLCQCHEGFALNPDEKTCT |

Fig. 11

```
14578444047_cura_56    KIDYCASSNHGCQYECVNTDDSYSCHCLKGFTLNPDKKTCRRINYCALNKPGCEHECVNM
14578440143_cura_56    KIDYCASSNHGCQYECVNTDDSYSCHCLKGFTLNPDKKTCRRINYCALNKPGCEHECVNM 14578444047_cura_56    EESYYCRCHRGYTLDPNGKPCSRVDHCAQQDHGCEQLCLNTEDSFVCQCSEGFLINEDLK
14578440143_cura_56    EESYYCRCHRGYTLDPNGKPCSRVDHCAQQDHGCEQLCLNTEDSFVCQCSEGFLINEDLK 14578444047_cura_56    TCSRVDYCLLSDHGCEYSCVNMDRSFACQCPEGHVLRSDGKTCAKLDSCALGDHGCEHSC
14578440143_cura_56    TCSRVDYCLLSDHGCEYSCVNMDRSFACQCPEGHVLRSDGKTCAKLDSCALGDHGCEHSC 14578444047_cura_56    VSSEDSFVCQCFEGYILREDGKTCRRKDVCQAIDHGCEHICVNSDDSYTCECLEGFRLTE
14578440143_cura_56    VSSEDSFVCQCFEGYILREDGKTCRRKDVCQAIDHGCEHICVNSDDSYTCECLEGFRLTE 14578444047_cura_56    DGKRCRISSGKDVCKSTHHGCEHICVNNGNSYICKCSEGFVLAEDGRRCKKCTEGPIDLV
14578440143_cura_56    DGKRCRISSGKDVCKSTHHGCEHICVNNGNSYICKCSEGFVLAEDGRRCKKCTEGPIDLV 14578444047_cura_56    FVIDGSKSLGEENFEVVKQFVTGIIDSLTTISPKAARVGLLQYSTQVHTEFTLRNFNSAKD
14578440143_cura_56    FVIDGSKSLGEENFEVVKQFVTGIIDSLTTISPKAARVGLLQYSTQVHTEFTLRNFNSAKD 14578444047_cura_56    MKKAVAHMKYMGKGSMTGLALKHMFERSFTQGEGARPFSTRVPRAAIVFTDGRAQDDVSE
14578440143_cura_56    MKKAVAHMKYMGKGSMTGLALKHMFERSFTQGEGARPLFHKGAQSSHCVHRRTGSG~~~~

14578444047_cura_56    WASKAKANGITMYAVGVGKAIEEELQEIASEPTNKHLFYAEDFSTMDEISEKLKKGICEA
14578440143_cura_56    ~~~~~~~~~~~~~~~~~~~~~~~~~~~~~~~~~~~~~~~~~~~~~~~~~~~~~~~~~~~

14578444047_cura_56    LEDSDGRQDSPAGELPKTVQQPTESEPVTINIQDLLSCSNFAVQHRYLFEEDNLLRSTQK
14578440143_cura_56    ~~~~~~~~~~~~~~~~~~~~~~~~~~~~~~~~~~~~~~~~~~~~~~~~~~~~~~~~~~~

14578444047_cura_56    LSHSTKPSGSPLEEKHDQCKCENLIMFQNLANEEVRKLTQRLEEMTQRMEALENRLRYR
14578440143_cura_56    ~~~~~~~~~~~~~~~~~~~~~~~~~~~~~~~~~~~~~~~~~~~~~~~~~~~~~~~~~~
```

Fig. 11 (continued)

| Normal & Tumor Tissues | 11696905 | 164064770206 | 21433858 | 216372620.64 |
|---|---|---|---|---|
| Endothelial cells | 3.5 | 0.0 | 6.6 | 0.0 |
| Endothelial cells (treated) | 2.9 | 0.0 | 2.0 | 0.0 |
| Pancreas | 9.4 | 3.1 | 1.2 | 0.0 |
| Pancreatic ca. CAPAN 2 | 3.7 | 0.0 | 0.3 | 0.0 |
| Adipose | 60.7 | 0.3 | 22.5 | 0.8 |
| Adrenal gland | 18.0 | 0.0 | 3.2 | 0.2 |
| Thyroid | 13.8 | 0.0 | 4.6 | 2.4 |
| Salivary gland | 0.0 | 0.6 | 0.7 | 36.3 |
| Pituitary gland | 2.2 | 0.6 | 4.0 | 1.4 |
| Brain (fetal) | 3.1 | 0.5 | 6.9 | 0.7 |
| Brain (whole) | 4.4 | 0.7 | 24.5 | 0.3 |
| Brain (amygdala) | 17.2 | 0.1 | 5.0 | 0.4 |
| Brain (cerebellum) | 1.6 | 1.2 | 41.8 | 1.4 |
| Brain (hippocampus) | 9.3 | 0.8 | 10.4 | 0.6 |
| Brain (hypothalamus) | 5.7 | 10.0 | 2.3 | 0.5 |
| Brain (substantia nigra) | 33.2 | 0.7 | 5.2 | 0.1 |
| Brain (thalamus) | 22.7 | 0.5 | 5.2 | 0.0 |
| Spinal cord | 21.8 | 0.3 | 4.0 | 1.5 |
| CNS ca. (glio/astro) U87-MG | 2.2 | 0.0 | 1.0 | 0.0 |
| CNS ca. (glio/astro) U-118-MG | 4.5 | 0.0 | 1.5 | 0.0 |
| CNS ca. (astro) SW1783 | 0.0 | 0.0 | 0.7 | 0.0 |
| CNS ca.* (neuro; met) SK-N-AS | 2.7 | 0.0 | 12.6 | 0.1 |
| CNS ca. (astro) SF-539 | 0.2 | 0.0 | 0.0 | 0.0 |
| CNS ca. (astro) SNB-75 | 1.3 | 0.0 | 0.6 | 0.0 |
| CNS ca. (glio) SNB-19 | 0.6 | 0.0 | 0.8 | 0.2 |
| CNS ca. (glio) U251 | 0.2 | 0.0 | 3.6 | 0.1 |
| CNS ca. (glio) SF-295 | 6.2 | 0.1 | 0.2 | 0.0 |
| Heart | 10.7 | 0.1 | 1.3 | 0.1 |
| Skeletal muscle | 18.4 | 0.0 | 0.2 | 0.2 |
| Bone marrow | 11.1 | 0.0 | 0.1 | 0.0 |
| Thymus | 7.3 | 0.9 | 2.5 | 0.5 |
| Spleen | 2.9 | 0.1 | 1.4 | 0.0 |
| Lymph node | 4.3 | 0.1 | 1.3 | 0.1 |

Fig. 14

| Normal & Tumor Tissues | 11696905 | 16406477.0.206 | 21433858 | 216372262.0.64 |
|---|---|---|---|---|
| Colon (ascending) | 1.3 | 0.2 | 5.1 | 1.3 |
| Stomach | 5.4 | 0.2 | 5.7 | 0.0 |
| Small intestine | 7.0 | 0.2 | 1.7 | 0.0 |
| Colon ca. SW480 | 0.4 | 0.0 | 0.0 | 0.1 |
| Colon ca.* (SW480 met)SW620 | 0.1 | 0.0 | 0.0 | 0.0 |
| Colon ca. HT29 | 0.4 | 0.0 | 0.0 | 0.1 |
| Colon ca. HCT-116 | 4.4 | 0.0 | 0.0 | 0.0 |
| Colon ca. CaCo-2 | 1.1 | 0.1 | 0.1 | 0.0 |
| Colon ca. HCT-15 | 11.0 | 0.2 | 0.3 | 0.2 |
| Colon ca. HCC-2998 | 0.0 | 0.0 | 1.3 | 0.0 |
| Gastric ca.* (liver met) NCI-N87 | 4.9 | 0.3 | 1.9 | 0.0 |
| Bladder | 18.8 | 0.1 | 10.8 | 0.1 |
| Trachea | 4.8 | 0.0 | 2.2 | 100.0 |
| Kidney | 7.3 | 0.4 | 13.1 | 0.1 |
| Kidney (fetal) | 11.0 | 1.8 | 29.5 | 0.1 |
| Renal ca. 786-0 | 0.4 | 0.0 | 0.0 | 0.0 |
| Renal ca. A498 | 56.3 | 0.0 | 0.0 | 0.1 |
| Renal ca. RXF 393 | 2.7 | 0.0 | 0.1 | 0.0 |
| Renal ca. ACHN | 1.0 | 0.0 | 0.1 | 0.1 |
| Renal ca. UO-31 | 1.8 | 0.0 | 0.4 | 0.1 |
| Renal ca. TK-10 | 13.4 | 0.5 | 0.2 | 0.1 |
| Liver | 74.7 | 0.7 | 2.1 | 0.1 |
| Liver (fetal) | 27.7 | 1.2 | 0.9 | 0.0 |
| Liver ca. (hepatoblast HepG2 | 7.4 | 0.0 | 0.0 | 0.0 |
| Lung | 9.9 | 0.0 | 2.9 | 0.0 |
| Lung (fetal) | 1.5 | 1.5 | 3.0 | 0.0 |
| Lung ca. (small cell) LX-1 | 0.4 | 0.0 | 0.0 | 0.0 |
| Lung ca. (small cell) NCI-H69 | 0.5 | 0.1 | 9.3 | 0.5 |
| Lung ca. (s.cell var.) SHP-77 | 0.6 | 0.4 | 100.0 | 1.7 |
| Lung ca. (large cell) NCI-H460 | 20.6 | 0.3 | 66.9 | 0.6 |
| Lung ca. (non-sm. cell) A549 | 3.3 | 0.0 | 15.5 | 0.1 |
| Lung ca. (non-s.cell) NCI-H23 | 7.4 | 0.5 | 9.0 | 0.0 |
| Lung ca (non-s.cell) HOP-62 | 32.1 | 0.1 | 1.5 | 0.1 |
| Lung ca. (non-s.cl) NCI-H522 | 11.0 | 0.6 | 0.0 | 0.0 |
| Lung ca. (squam.) SW 900 | 3.3 | 0.9 | 6.1 | 0.1 |

Fig. 14 (continued)

| Normal & Tumor Tissues | 11696905.0 | 16406477.0.206 | 214333858.0 | 216372262.0.64 |
|---|---|---|---|---|
| Mammary gland | 30.4 | 1.5 | 12.2 | 0.0 |
| Breast ca.* (pl. effusion) MCF-7 | 4.8 | 0.0 | 0.0 | 0.0 |
| Breast ca.* (pl.ef) MDA-MB-231 | 2.2 | 0.0 | 0.0 | 0.1 |
| Breast ca.* (pl. effusion) T47D | 9.8 | 0.1 | 0.9 | 0.6 |
| Breast ca. BT-549 | 9.2 | 0.1 | 1.2 | 0.3 |
| Breast ca. MDA-N | 1.3 | 0.0 | 0.0 | 0.0 |
| Ovary | 6.0 | 0.3 | 9.7 | 0.0 |
| Ovarian ca. OVCAR-3 | 1.6 | 0.1 | 0.8 | 0.1 |
| Ovarian ca. OVCAR-4 | 1.9 | 0.0 | 0.0 | 0.0 |
| Ovarian ca. OVCAR-5 | 7.1 | 0.3 | 6.9 | 0.6 |
| Ovarian ca. OVCAR-8 | 1.3 | 2.7 | 2.7 | 0.0 |
| Ovarian ca. IGROV-1 | 0.7 | 0.2 | 5.0 | 0.0 |
| Ovarian ca.* (ascites) SK-OV-3 | 2.5 | 0.0 | 0.2 | 0.0 |
| Myometrium | 2.3 | 0.0 | 41.2 | 1.2 |
| Uterus | 6.3 | 0.6 | 25.7 | 0.1 |
| Placenta | 100.0 | 0.0 | 94.0 | 0.1 |
| Prostate | 13.3 | 0.1 | 3.4 | 0.1 |
| Prostate ca.* (bone met) PC-3 | 7.9 | 1.7 | 0.2 | 0.2 |
| Testis | 14.3 | 100.0 | 37.1 | 4.0 |
| Melanoma Hs688(A).T | 1.4 | 0.0 | 0.0 | 0.0 |
| Melanoma* (met) Hs688(B).T | 5.3 | 0.0 | 0.0 | 0.0 |
| Melanoma UACC-62 | 0.6 | 0.0 | 0.0 | 0.0 |
| Melanoma M14 | 0.9 | 0.1 | 0.3 | 0.2 |
| Melanoma LOX IMVI | 1.0 | 0.0 | 0.0 | 0.1 |
| Melanoma* (met) SK-MEL-5 | 0.0 | 0.0 | 8.7 | 0.0 |
| Melanoma SK-MEL-28 | 100.0 | 0.0 | 0.0 | 0.0 |

Fig. 14 (continued)

NUCLEIC ACID SEQUENCES ENCODING HUMAN ANGIOPOIETIN-LIKE POLYPEPTIDES

RELATED APPLICATIONS

This application is a CONTINUATION of PCT/US00/19890 filed Jul. 20, 2000, published, and is a CONTINUATION of U.S. Ser. No. 09/619,252 filed Jul. 19, 2000, abandoned, both of which claim the benefit of U.S. Ser. No. 60/144,722 filed Jul. 20, 1999, abandoned and U.S. Ser. No. 60/167,785, filed Nov. 29, 1999, abandoned.

FIELD OF THE INVENTION

The invention relates to generally to polynucleotides and the polypeptides encoded thereby and more particularly to polynucleotides encoding polypeptides that cross one or more membranes in eukaryotic cells.

BACKGROUND OF THE INVENTION

Eukaryotic cells are subdivided by membranes into multiple, functionally-distinct compartments, referred to as organelles. Many biologically important proteins are secreted from the cell after crossing multiple membrane-bound organelles. These proteins can often be identified by the presence of sequence motifs referred to as "sorting signals" in the protein, or in a precursor form of the protein. These sorting signals can also aid in targeting the proteins to their appropriate destination.

One specific type of sorting signal is a signal sequence, which is also referred to as a signal peptide or leader sequence. This signal sequence can be present as an amino-terminal extension on a newly synthesized polypeptide. A signal sequence possesses the ability to "target" proteins to an organelle known as the endoplasmic reticulum (ER).

The signal sequence takes part in an array of protein-protein and protein-lipid interactions that result in the translocation of a signal sequence-containing polypeptide through a channel within the ER. Following translocation, a membrane-bound enzyme, designated signal peptidase, liberates the mature protein from the signal sequence.

Secreted and membrane-bound proteins are involved in many biologically diverse activities. Examples of known, secreted proteins include, e.g., insulin, interferon, interleukin, transforming growth factor-β, human growth hormone, erythropoietin, and lymphokine. Only a limited number of genes encoding human membrane-bound and secreted proteins have been identified.

SUMMARY OF THE INVENTION

The invention is based, in part, upon the discovery of novel nucleic acids and secreted polypeptides encoded thereby. The nucleic acids and polypeptides are collectively referred to herein as "SECP".

Accordingly, in one aspect, the invention includes an isolated nucleic acid that encodes a SECP polypeptide, or a fragment, homolog, analog or derivative thereof. For example, the nucleic acid can encode a polypeptide at least 85% identical to a polypeptide comprising the amino acid sequences of SEQ ID NO: 2, 4, 6, 8, 10, 12, 14, 16, and 18. The nucleic acid can be, e.g., a genomic DNA fragment, cDNA molecule. In some embodiments, the nucleic acid includes the sequence the invention provides an isolated nucleic acid molecule that includes the nucleic acid sequence of any of SEQ ID NO: 1, 3, 5, 7, 9, 11, 13, 15, and 17.

Also included within the scope of the invention is a vector containing one or more of the nucleic acids described herein, and a cell containing the vectors or nucleic acids described herein.

The invention is also directed to host cells transformed with a vector comprising any of the nucleic acid molecules described above.

In another aspect, the invention includes a pharmaceutical composition that includes a SECP nucleic acid and a pharmaceutically acceptable carrier or diluent.

In a further aspect, the invention includes a substantially purified SECP polypeptide, e.g., any of the SECP polypeptides encoded by a SECP nucleic acid, and fragments, homologs, analogs, and derivatives thereof. The invention also includes a pharmaceutical composition that includes a SECP polypeptide and a pharmaceutically acceptable carrier or diluent.

In a still a further aspect, the invention provides an antibody that binds specifically to a SECP polypeptide. The antibody can be, e.g., a monoclonal or polyclonal antibody, and fragments, homologs, analogs, and derivatives thereof. The invention also includes a pharmaceutical composition including SECP antibody and a pharmaceutically acceptable carrier or diluent. The invention is also directed to isolated antibodies that bind to an epitope on a polypeptide encoded by any of the nucleic acid molecules described above.

The invention also includes kits comprising any of the pharmaceutical compositions described above.

The invention further provides a method for producing a SECP polypeptide by providing a cell containing a SECP nucleic acid, e.g., a vector that includes a SECP nucleic acid, and culturing the cell under conditions sufficient to express the SECP polypeptide encoded by the nucleic acid. The expressed SECP polypeptide is then recovered from the cell. Preferably, the cell produces little or no endogenous SECP polypeptide. The cell can be, e.g., a prokaryotic cell or eukaryotic cell.

The invention is also directed to methods of identifying a SECP polypeptide or nucleic acids in a sample by contacting the sample with a compound that specifically binds to the polypeptide or nucleic acid, and detecting complex formation, if present.

The invention further provides methods of identifying a compound that modulates the activity of a SECP polypeptide by contacting SECP polypeptide with a compound and determining whether the SECP polypeptide activity is modified.

The invention is also directed to compounds that modulate SECP polypeptide activity identified by contacting a SECP polypeptide with the compound and determining whether the compound modifies activity of the SECP polypeptide, binds to the SECP polypeptide, or binds to a nucleic acid molecule encoding a SECP polypeptide.

In another aspect, the invention provides a method of determining the presence of or predisposition of a SECP-associated disorder in a subject. The method includes providing a sample from the subject and measuring the amount of SECP polypeptide in the subject sample. The amount of SECP polypeptide in the subject sample is then compared to the amount of SECP polypeptide in a control sample. An alteration in the amount of SECP polypeptide in the subject protein sample relative to the amount of SECP polypeptide in the control protein sample indicates the subject has a tissue proliferation-associated condition. A control sample is preferably taken from a matched individual, i.e., an individual of similar age, sex, or other general condition but who is not suspected of having a tissue proliferation-associated condition. Alternatively, the control sample may be taken from the subject at a time when the subject is not suspected of having a tissue proliferation-associated disorder. In some embodiments, the SECP is detected using a SECP antibody.

In a further aspect, the invention provides a method of determining the presence of or predisposition of a SECP-associated disorder in a subject. The method includes providing a nucleic acid sample (e.g., RNA or DNA, or both) from the subject and measuring the amount of the SECP nucleic acid in the subject nucleic acid sample. The amount of SECP nucleic acid sample in the subject nucleic acid is then compared to the amount of a SECP nucleic acid in a control sample. An alteration in the amount of SECP nucleic acid in the sample relative to the amount of SECP in the control sample indicates the subject has a tissue proliferation-associated disorder.

In a still further aspect, the invention provides method of treating or preventing or delaying a SECP-associated disorder. The method includes administering to a subject in which such treatment or prevention or delay is desired a SECP nucleic acid, a SECP polypeptide, or a SECP antibody in an amount sufficient to treat, prevent, or delay a tissue proliferation-associated disorder in the subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents and other references mentioned herein are incorporated by reference in their entirety. In the case of conflict, the present Specification, including definitions, will control. In addition, the materials, methods, and examples are illustrative only and not intended to be limiting.

Other features and advantages of the invention will be apparent from the following detailed description and claims.

BRIEF DESCRIPTION OF THE FIGURES

FIG. 1 is a representation of a SECP 1 nucleic acid sequence (SEQ ID NO: 1) according to the invention, along with an amino acid sequence (SEQ ID NO: 2) encoded by the nucleic acid sequence.

FIG. 2 is a representation of a SECP 2 nucleic acid sequence (SEQ ID NO: 3) according to the invention, along with an amino acid sequence (SEQ ID NO: 4) encoded by the nucleic acid sequence.

FIG. 3 is a representation of a SECP 3 nucleic acid sequence (SEQ ID NO: 5) according to the invention, along with an amino acid sequence (SEQ ID NO: 6) encoded by the nucleic acid sequence.

FIG. 4 is a representation of a SECP 4 nucleic acid sequence (SEQ ID NO: 7) according to the invention, along with an amino acid sequence (SEQ ID NO:8) encoded by the nucleic acid sequence.

FIG. 5 is a representation of a SECP 5 nucleic acid sequence (SEQ ID NO: 9) according to the invention, along with an amino acid sequence (SEQ ID NO: 10) encoded by the nucleic acid sequence.

FIG. 6 is a representation of a SECP 6 nucleic acid sequence (SEQ ID NO: 11) according to the invention, along with an amino acid sequence (SEQ ID NO: 12) encoded by the nucleic acid sequence.

FIG. 7 is a representation of a SECP 7 nucleic acid sequence (SEQ ID NO: 13) according to the invention, along with an amino acid sequence (SEQ ID NO: 14) encoded by the nucleic acid sequence.

FIG. 8 is a representation of a SECP 8 nucleic acid sequence (SEQ ID NO: 15) according to the invention, along with an amino acid sequence (SEQ ID NO: 16) encoded by the nucleic acid sequence.

FIG. 9 is a representation of a SECP 9 nucleic acid sequence (SEQ ID NO: 17) according to the invention, along with an amino acid sequence (SEQ ID NO: 18) encoded by the nucleic acid sequence.

FIG. 10 is a representation of an alignment of the proteins encoded by clones 11618130.0.27 (SEQ ID NO: 4) and 11618130.0.184 (SEQ ID NO: 16).

FIG. 11 is a representation of an alignment of the proteins encoded by clones 14578444.0.143 (SECP4; SEQ ID NO:8) and 14578444.0.47 (SECP 5; SEQ ID NO: 10).

FIG. 14 is a representation of a real-time expression analysis of the clones of the invention.

DETAILED DESCRIPTION OF THE INVENTION

Figure 12:
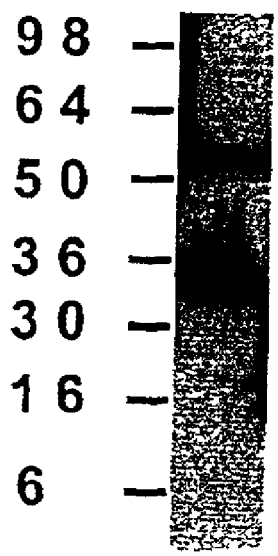
FIG. 12 is a representation of a Western blot of a polypeptide expressed in 293 cells of a polynucleotide containing sequences encoded by clone 11618130.

The invention provides novel polynucleotides and the polypeptides encoded thereby. Included in the invention are ten novel nucleic acid sequences and their encoded polypeptides. These sequences are collectively referred to as "SECP nucleic acids" or "SECP polynucleotides" and the corresponding encoded polypeptide is referred to as a "SECP polypeptide" or "SECP protein". For example, a SECP nucleic acid according to the invention is a nucleic acid including a SECP nucleic acid, and a SECP polypeptide according to the invention is a polypeptide that includes the amino acid sequence of a SECP polypeptide. Unless indicated otherwise, "SECP" is meant to refer to any of the novel sequences disclosed herein. Each of the nucleic acid and amino acid sequences have been assigned a unique SECP Identification Number, with designations SECP1 through SECP9.

TABLE 1 provides a cross-reference to the assigned SECP Number, Clone or Probe Identification Number, and Sequence Identification Number (SEQ ID NO:) for both the nucleic acid and encoded polypeptides of SECP1–9.

TABLE 1

| CLONE/PROBE | FIG. | SEQ ID NO: (Nucleic Acid) | SEQ ID NO: (Polypeptide) |
|---|---|---|---|
| 21433858 | 1 | 1 | 2 |
| 11618130.0.27 | 2 | 3 | 4 |
| 11696905-0-47 | 3 | 5 | 6 |
| 14578444.0.143 | 4 | 7 | 8 |
| 14578444.0.47 | 5 | 9 | 10 |
| 14998905.0.65 | 6 | 11 | 12 |
| 16406477.0.206 | 7 | 13 | 14 |
| 11618130.0.184 | 8 | 15 | 16 |
| 21637262.0.64 | 9 | 17 | 18 |
| 11618130 Forward | | 19 | |
| 11618130 Reverse | | 20 | |
| PSec-V5-His | | 21 | |

TABLE 1-continued

| CLONE/PROBE | FIG. | SEQ ID NO: (Nucleic Acid) | SEQ ID NO: (Polypeptide) |
|---|---|---|---|
| Forward PSec-V5-His Reverse | | 22 | |
| 16406477 Forward | | 23 | |
| 16406477 Reverse | | 24 | |
| Ag 383 (F) | | 25 | |
| Ag 383 (R) | | 26 | |
| Ag 383 (P) | | 27 | |
| Ag 53 (F) | | 28 | |
| Ag 53 (R) | | 29 | |
| Ag 53 (P) | | 30 | |
| Ag 127 (F) | | 31 | |
| Ag 127 (R) | | 32 | |
| Ag 127 (P) | | 33 | |
| Ab 5 (F) | | 34 | |
| Ab 5 (R) | | 35 | |
| Ab 5 (P) | | 36 | |

Nucleic acid sequences and polypeptide sequences for SECP nucleic acids and polypeptides, as disclosed herein, are provided in the following section of the Specification.

SECP nucleic acids, and their encoded polypeptides, according to the invention are useful in a variety of applications and contexts. For example, various SECP nucleic acids and polypeptides according to the invention are useful, inter alia, as novel members of the protein families according to the presence of domains and sequence relatedness to previously described proteins.

SECP nucleic acids and polypeptides according to the invention can also be used to identify cell types based on the presence or absence of various SECP nucleic acids according to the invention. Additional utilities for SECP nucleic acids and polypeptides are discussed below.

SECP1

A SECP1 nucleic acid and polypeptide according to the invention includes the nucleic acid sequence (SEQ ID NO: 1) and encoded polypeptide sequence (SEQ ID NO: 2) of clone 21433858. FIG. 1 illustrates the nucleic acid and amino acid sequences, as well as the alignment between these two sequences.

This clone includes a nucleotide sequence (SEQ ID NO: 1) of 6373 bp. The nucleotide sequence includes an open reading frame (ORF) encoding a polypeptide of 1588 amino acid residues (SEQ ID NO: 2) with a predicted molecular weight of 178042.1 Daltons. The start codon is located at nucleotides 235–237 and the stop codon is located at nucleotides 4999–5001. The protein encoded by clone 21433858 is predicted by the PSORT program to localize in the plasma membrane with a certainty of 0.7300. The program SignalP predicts that there is a signal peptide with the most probable cleavage site located between residues 23 and 24, in the sequence CMG-DE.

Real-time gene expression analysis was performed on SECP1 (clone 21433858). The results demonstrate that RNA sequences with homology to clone 21433858 are detected in various cell types. The relative abundance of RNA homologous to clone 21433858 is shown in FIG. 14 (see also Examples, below). Cell types endothelial cells (treated and untreated), pancreas, adipose, adrenal gland, thyroid, mammary gland, myometrium, uterus, placenta, prostate, testis, and in neoplastic cells derived from ovarian carcinoma OVCAR-3, ovarian carcinoma OVCAR-5, ovarian carcinoma OVCAR-8, ovarian carcinoma IGROV-1, ovarian carcinoma (ascites) SK-OV-3, breast carcinoma BT-549, prostate carcinoma (bone metastases) PC-3, Melanoma M14, and melanoma (met) SK-MEL-5. Accordingly, SECP1 nucleic acids according to the invention can be used to identify one or more of these cell types. The presence of RNA sequences homologous to a SECP1 nucleic in a sample indicates that the sample contains one or more of the above-cell types.

A search of sequence databases using BLASTX reveals that residues 299–1588 of the polypeptide encoded clone 21433858 are 100% identical to the 1290 residue human KIAA0960 protein (ACC: SPTREMBL-ACC:Q9UPZ6). In addition, the protein of clone 21433858 has 542 of 543 residues (99%) identical to, and 543 of 543 residues (100%) positive with, the 543 residue fragment of a human hypothetical protein (SPTREMBL-ACC:O60407).

The proteins of the invention encoded by clone 21433858 include the protein disclosed as being encoded by the ORF described herein, as well as any mature protein arising therefrom as a result of post-translational modifications. Thus, the proteins of the invention encompass both a precursor and any active forms of the clone 21433858 protein.

SECP2

A SECP2 nucleic acid and polypeptide according to the invention includes a nucleic acid sequence (SEQ ID NO:3) and an encoded polypeptide sequence (SEQ ID NO:4) of clone 11618130.0.27. FIG. 2 illustrates the nucleic acid sequence and amino acid sequence, as well as the alignment between these two sequences.

This clone includes a nucleotide sequence (SEQ ID NO:3) of 1894 nucleotides. The nucleotide sequence includes an open reading frame (ORF) encoding a polypeptide of 267 amino acid residues with a predicted molecular weight of 28043 Daltons. The start codon is at nucleotides 732–734 and the stop codon is at nucleotides 1534–1536. The protein encoded by clone 11618130.0.27 is predicted by the PSORT program to localize in the microbody (peroxisome) with a certainty of 0.5035. The program SignalP predicts that there is no signal peptide in the encoded polypeptide.

A search of the sequence databases using BLAST P and BLASTX reveals that clone 11618130.0.27 has 330 of 333 residues (99%) identical to and positive with a 571 residue human protein termed PRO351 (PCT Publication WO9946281-A2 published Sep. 16, 1999). In addition, it was found to have 83 of 250 residues (33%) identical to, and 119 of 250 residues (47%) positive with the 343 residue human prostasin precursor (EC 3.4.21.-) (SWISSPROT-ACC:Q16651).

The proteins of the invention encoded by clone 11618130.0.27 includes the protein disclosed as being encoded by the ORF described herein, as well as any mature protein arising therefrom as a result of post-translational modification. Thus, the protein of the invention encompasses both a precursor and any active forms of the 11618130.0.27 protein.

SECP3

A SECP3 nucleic acid and polypeptide according to the invention includes the nucleic acid sequence (SEQ ID NO:5) and encoded polypeptide sequence (SEQ ID NO:6) of clone 11696905-0-47. FIG. 3 illustrates the nucleic acid sequence and amino acid sequence, as well as the alignment between these two sequences.

Clone 11696905-0-47 was obtained from fetal brain. In addition, RNA sequences were also found to be present in tissues including, uterus, pregnant and non-pregnant uterus, ovarian tumor, placenta, bone marrow, hippocampus, synovial membrane, fetal heart, fetal lung, pineal gland and melanocytes. This clone includes a nucleotide sequence of 1855 bp (SEQ ID NO:5). The nucleotide sequence includes an open reading frame (ORF) encoding a polypeptide of 405 amino acid residues (SEQ ID NO:6) with a predicted molecular weight of 44750 Daltons. The start codon is located at nucleotides 154–156 and the stop codon is located at nucleotides 1369–1371. The protein encoded by clone 11696905-0-47 is predicted by the PSORT program to localize extracellularly with a certainty of 0.7332. The program SignalP predicts that there is a signal peptide with the most probable cleavage site located between residues 25 and 26, in the sequence AQG-GP.

Real-time gene expression analysis was performed on SECP3 (clone 11696905-0-47). The results demonstrate that RNA sequences homologous to clone 11696905-0-47 are detected in various cell types. Cell types include adipose, adrenal gland, thyroid, brain, heart, skeletal muscle, bone marrow, colon, bladder, liver, lung, mammary gland, placenta, and testis, and in neoplastic cells derived from renal carcinoma A498, lung carcinoma NCI-H460, and melanoma SK-MEL-28.

Accordingly, SECP3 nucleic acids according to the invention can be used to identify one or more of these cell types. The presence of RNA sequences homologous to a SECP3 nucleic in a sample indicates that the sample contains one or more of the above-cell types.

A search of the sequence databases using BLASTX reveals that clone 11696905-0-47 has 403 of 405 residues (99%) identical to, and 404 of 405 residues (99%) positive with, the 405 residue human angiopoietin-related protein (SPTREMBL-ACC:Q9Y5B3). Angiopoietin homologues are useful to stimulate cell growth and tissue development. The polypeptides of clone 11696905-0-47 tend to be found as multimeric proteins (see Example 7) and are believed to have angiogenic or hematopoietic activity. They can thus be used in assays for angiogenic activity, as well as used therapeutically to stimulate restoration of vascular structure in various tissues. Examples of such uses include, but are not limited to, treatment of full-thickness skin wounds, including venous stasis ulcers and other chronic, non-healing wounds, as well as fracture repair, skin grafting, reconstructive surgery, and establishment of vascular networks in transplanted cells and tissues.

The proteins of the invention encoded by clone 11696905-0-47 include the protein disclosed as being encoded by the ORF described herein, as well as any mature protein arising therefrom as a result of post-translational modifications. Thus, the proteins of the invention encompass both a precursor and any active forms of the clone 11696905-0-47 protein.

SECP4

A SECP4 nucleic acid and polypeptide according to the invention includes the nucleic acid sequence (SEQ ID NO:7) and encoded polypeptide sequence (SEQ ID NO:8) of 14578444.0.143. FIG. 4 illustrates the nucleic acid sequence and amino acid sequence, as well as the alignment between these two sequences.

Clone 14578444.0.143 was obtained from fetal brain. This clone includes a nucleotide sequence (SEQ ID NO:7) of 3026 bp. The nucleotide sequence includes an open reading frame (ORF) encoding a polypeptide of 776 amino acid residues (SEQ ID NO:8) with a predicted molecular weight of 86220.8 Daltons. The start codon is located at nucleotides 55–57 and the stop codon is located at nucleotides 2384–2386. The protein encoded by clone 14578444.0.143 is predicted by the PSORT program to localize in the endoplasmic reticulum (membrane) with a certainty of 0.8200. The program SignalP predicts that there is a signal peptide with the most probable cleavage site located between residues 23 and 24 in the sequence AEA-RE.

A search of the sequence databases using BLASTX reveals that clone 14578444.0.143 has 655 of 757 residues (86%) identical to, and 702 of 757 residues (92%) positive with, the 956 residue murine matrilin-2 precursor protein (SWISSPROT-ACC:O08746), extending over residues 1–754 of the reference protein. Additional similarities are found with lower identities in residues 649–837 of the murine protein. Additionally, the search shows that there is a lower degree of similarity to murine matrilin-4 precursor. The protein of clone 14578444.0.143 also has 595 of 606 residues (98%) identical to, and 598 of 606 residues (98%) positive with, the 632 residue human matrilin-3 (PCT publication WO9904002-A1).

The matrilin proteins and polynucleotides can be used for treating a variety of developmental disorders (e.g., renal tubular acidosis, anemia, Cushing's syndrome). The proteins can serve as targets for antagonists that should be of use in treating diseases related to abnormal vesicle trafficking. These may include, but are not limited to, diseases such as cystic fibrosis, glucose-galactose malabsorption syndrome, hypercholesterolaemia, diabetes mellitus, diabetes insipidus, hyper- and hypoglycemia, Graves disease, goiter, Cushing's disease, Addison's disease, gastrointestinal disorders including ulcerative colitis, gastric and duodenal ulcers, and other conditions associated with abnormal vesicle trafficking including AIDS, and allergies including hay fever, asthma, and urticaria (hives), autoimmune hemolytic anemia, proliferative glomerulonephritis, inflammatory bowel disease, multiple sclerosis, myasthenia gravis, rheumatoid and osteoarthritis, scleroderma, Chediak-Higashi and Sjogren's syndromes, systemic lupus erythematosus, toxic shock syndrome, traumatic tissue damage, and viral, bacterial, fungal, helminth, protozoal infections, a neoplastic disorder (e.g., adenocarcinoma, leukemia, lymphoma, melanoma, myeloma, sarcoma, teratocarcinoma, and cancers), or an immune disorder, (e.g., AIDS, Addison's disease, adult respiratory distress syndrome, allergies, anemia, asthma, atherosclerosis, bronchitis, cholecystitis, Crohn's disease and ulcerative colitis).

The proteins of the invention encoded by clone 14578444.0.143 include the protein disclosed as being encoded by the ORF described herein, as well as any mature protein arising therefrom as a result of post-translational modifications. Thus, the proteins of the invention encompass both a precursor and any active forms of the proteins encoded by clone 14578444.0.143 (SECP4).

SECP5

A SECP5 nucleic acid and polypeptide according to the invention includes the nucleic acid sequence (SEQ ID NO:9) and encoded polypeptide sequence (SEQ ID NO:10) of clone 14578444.0.47. FIG. 5 illustrates the nucleic acid sequence and amino acid sequence, as well as the alignment between these two sequences.

Clone 14578444.0.47 was obtained from fetal brain. This clone includes a nucleotide sequence (SEQ ID NO:9) of 3447 bp. The nucleotide sequence includes an open reading frame (ORF) encoding a polypeptide of 959 amino acid residues (SEQ ID NO: 10) with a predicted molecular weight of 107144 Daltons. The start codon is located at nucleotides 55–57 and the stop codon is located at nucleotides 2933–2935. The protein encoded by clone 14578444.0.47 is predicted by the PSORT program to localize to the endoplasmic reticulum (membrane) with a certainty of 0.8200. The program SignalP predicts that there is a signal peptide with the most probable cleavage site located between residues 23 and 24 in the sequence AEA-RE.

A search of the sequence databases using BLASTX reveals that clone 14578444.0.47 has 829 of 959 residues (86%) identical to, and 887 of 959 residues (92%) positive with, the 956 residue murine matrilin-2 precursor protein (ACC: SWISSPROT-ACC:O08746). The protein encoded by clone 14578444.0.47 also has 594 of 606 residues (98%) identical to, and 597 of 606 residues (98%) positive with, the 632 residue human matrilin-3 (PCT publication WO9904002). In addition, the protein encoded by clone 14578444.0.47 also has 616 of 678 residues (90%) identical to, and 632 of 678 residues (93%) positive with the 915 residue human protein PRO219 (PCT publication WO9914328-A2).

The proteins encoded by clones 14578444.0.143 (SECP4) and 14578444.0.47 (SECP5) are compared in an amino acid residue alignment shown in FIG. 11. It can be seen that the main portion of the two proteins starting with their amino-termini are virtually identical, and that short sequences in each corresponding to the carboxyl-terminal sequence of the shorter protein, clone 14578444.0.143, differ from one another. Furthermore, clone 14578444.0.47 has an extended carboxyl-terminal sequence that is missing in clone 14578444.0.143. Therefore, clones 14578444.0.143 (SECP4) and 14578444.0.47 (SECP5) are apparently related to one another as splice variants, with respect to their sequences at the carboxyl-terminal ends.

The matrilin proteins and polynucleotides can be used for treating a variety of developmental disorders (e.g., renal tubular acidosis, anemia, Cushing's syndrome). The proteins can serve as targets for antagonists that should be of use in treating diseases related to abnormal vesicle trafficking. These may include, but are not limited to, diseases such as cystic fibrosis, glucose-galactose malabsorption syndrome, hypercholesterolaemia, diabetes mellitus, diabetes insipidus, hyper- and hypoglycemia, Graves disease, goiter, Cushing's disease, Addison's disease, gastrointestinal disorders including ulcerative colitis, gastric and duodenal ulcers, and other conditions associated with abnormal vesicle trafficking including AIDS, and allergies including hay fever, asthma, and urticaria (hives), autoimmune hemolytic anemia, proliferative glomerulonephritis, inflammatory bowel disease, multiple sclerosis, myasthenia gravis, rheumatoid and osteoarthritis, scleroderma, Chediak-Higashi and Sjogren's syndromes, systemic lupus erythematosus, toxic shock syndrome, traumatic tissue damage, and viral, bacterial, fungal, helminth, protozoal infections, a neoplastic disorder (e.g., adenocarcinoma, leukemia, lymphoma, melanoma, myeloma, sarcoma, teratocarcinoma, and cancers), or an immune disorder, (e.g., AIDS, Addison's disease, adult respiratory distress syndrome, allergies, anemia, asthma, atherosclerosis, bronchitis, cholecystitis, Crohn's disease and ulcerative colitis).

The proteins of the invention encoded by clone 14578444.0.47 include the protein disclosed as being encoded by the ORF described herein, as well as any mature protein arising therefrom as a result of post-translational modifications. Thus, the proteins of the invention encompass both a precursor and any active forms of the proteins encoded by clone 14578444.0.47 (SECP5).

SECP6

A SECP6 nucleic acid and polypeptide according to the invention includes the nucleic acid sequence (SEQ ID NO:11) and encoded polypeptide sequence (SEQ ID NO:12) of clone 14998905.0.65. FIG. 6 illustrates the nucleic acid sequence and amino acid sequence, as well as the alignment between these two sequences.

Clone 14998905.0.65 was obtained from lymphoid tissue, in particular, from the lymph node. This clone includes a nucleotide sequence (SEQ ID NO:11) of 967 bp. The nucleotide sequence includes an open reading frame (ORF) encoding a polypeptide of 245 amino acid residues (SEQ ID NO:12) with a predicted molecular weight of 27327.2 Daltons. The start codon is located at nucleotides 166–168 and the stop codon is located at nucleotides 902–904. The protein encoded by clone 14998905.0.65 is predicted by the PSORT program to localize in the microbody (peroxisome) with a certainty of 0.7480. PSORT predicts that there is no amino-terminal signal sequence. Conversely, the program SignalP predicts that there is a signal peptide with the most probable cleavage site located between residues 20 and 21, in the sequence GIG-AE.

A search of the sequence databases using BLASTX reveals that clone 14998905.0.65 has 204 of 226 residues (90%) identical to, and 214 of 226 residues (94%) positive with, the 834 residue murine semaphorin 4C precursor protein (SWISSPROT-ACC:Q64151). Semaphorin 4C is indicated as being a Type I membrane protein widely expressed in the nervous system during development. In addition, it contains one immunoglobulin-like C2-type domain. The protein encoded by clone 14998905.0.65 also has similarities to mouse CD100 antigen (PCT publication WO9717368-A1) and to human semaphorin (JP10155490-A).

The proteins of the invention encoded by clone 14998905.0.65 include the protein disclosed as being encoded by the ORF described herein, as well as any mature protein arising therefrom as a result of post-translational modifications. Thus, the proteins of the invention encompass both a precursor and any active forms of the clone 14998905.0.65 protein.

SECP7

A SECP7 nucleic acid and polypeptide according to the invention includes the nucleic acid sequence (SEQ ID NO: 13) and encoded polypeptide sequence (SEQ ID NO:14) of clone 16406477.0.206. FIG. 7 illustrates the nucleic acid sequence and amino acid sequence, as well as the alignment between these two sequences.

Clone 16406477.0.206 was obtained from testis. In addition, sequences of clone 16406477.0.206 were also found in an RNA pool derived from adrenal gland, mammary gland, prostate gland, testis, uterus, bone marrow, melanoma, pituitary gland, thyroid gland and spleen. This clone includes a nucleotide sequence (SEQ ID NO:13) comprising of 1359 bp with an open reading frame (ORF) encoding a polypeptide of 385 amino acid residues (SEQ ID NO:14) with a predicted molecular weight of 43087.3 Daltons. The start codon is located at nucleotides 45–47 and the stop codon is located at nucleotides 1201–1203. The protein encoded by clone 16406477.0.206 is predicted by the PSORT program to localize extracellularly with a certainty of 0.5804 and to have a cleavable amino-terminal signal sequence. The program SignalP predicts that there is a signal peptide with the most probable cleavage site located between residues 39 and 40, in the sequence CWG-AG.

Real-time expression analysis was performed on SECP7 (clone 16406477.0.206). The results demonstrate that RNA homologous to this clone is found in multiple cell and tissue types. These cells and tissues include brain, mammary gland, and testis, and in neoplastic cells derived from ovarian carcinoma OVCAR-3, ovarian carcinoma OVCAR-5, ovarian carcinoma OVCAR-8, ovarian carcinoma IGROV-1, breast carcinoma (pleural effusion) T47D, breast carcinoma BT-549, melanoma M14. Real-time gene expression analysis was performed on SECP3 (clone 11696905-0-47). The results demonstrate that RNA sequences homologous to clone 11696905-0-47 are detected in various cell types. Cell types include adipose, adrenal gland, thyroid, brain, heart, skeletal muscle, bone marrow, colon, bladder, liver, lung, mammary gland, placenta, and testis, and in neoplastic cells derived from renal carcinoma A498, lung carcinoma NCI-H460, and melanoma SK-MEL-28.

Accordingly, SECP7 nucleic acids according to the invention can be used to identify one or more of these cell types. The presence of RNA sequences homologous to a SECP7 nucleic in a sample indicates that the sample contains one or more of the above-cell types.

A search of the sequence databases using BLASTX reveals that clone 16406477.0.206 is 100% identical to a human testis-specific protein TSP50 (SPTREMBL-ACC:Q9U138) with a trypsin/chymotrypsin-like domain. In addition, the protein encoded by clone 16406477.0.206 has low similarity to the 343 residue human prostasin precursor (EC 3.4.21.-) (SWISSPROT ACC:Q16651).

The proteins of the invention encoded by clone 16406477.0.206 include the protein disclosed as being encoded by the ORF described herein, as well as any mature protein arising therefrom as a result of post-translational modifications. Thus, the proteins of the invention encompass both a precursor and any active forms of the clone 16406477.0.206 protein.

SECP8

A SECP8 nucleic acid and polypeptide according to the invention includes the nucleic acid sequence (SEQ ID NO:15) and encoded polypeptide sequence (SEQ ID NO:16) of clone 11618130.0.184. FIG. 8 illustrates the nucleic acid sequence and amino acid sequence, as well as the alignment between these two sequences.

Clone 11618130.0.184 includes a nucleotide sequence (SEQ ID NO:15) of 1445 bp. The nucleotide sequence includes an open reading frame (ORF) encoding a polypeptide of 198 amino acid residues (SEQ ID NO:16) with a predicted molecular weight of 20659 Daltons. The start codon is located at nucleotides 732–734 and the stop codon is located at nucleotides 1326–1328. The protein encoded by clone 11618130.0.184 is predicted by the PSORT program to localize in the cytoplasm. The program SignalP predicts that there is no signal peptide.

Clones 11618130.0.184 (SECP8) and 11618130.0.27 (SECP2) resemble each other in that they are identical over most of their common sequences, and differ only at the carboxyl-terminal end. In addition, clone 11618130.0.27 extends further at the carboxyl-terminal end than does clone 11618130.0.184. An alignment of clones 11618130.0.27 and 11618130.0.184 is shown in FIG. 10.

The proteins of the invention encoded by clone 11618130.0.184 include the protein disclosed as being encoded by the ORF described herein, as well as any mature protein arising therefrom as a result of post-translational modifications. Thus, the proteins of the invention encompass both a precursor and any active forms of the 11618130.0.184 protein.

SECP9

A SECP9 nucleic acid and polypeptide according to the invention includes the nucleic acid sequence (SEQ ID NO:17) and encoded polypeptide sequence (SEQ ID NO:18) of clone 21637262.0.64. FIG. 9 illustrates the nucleic acid sequence and amino acid sequence, as well as the alignment between these two sequences.

Clone 21637262.0.64 was obtained from salivary gland. This clone includes a nucleotide sequence (SEQ ID NO:17) of 1600 bp. The nucleotide sequence includes an open reading frame (ORF) encoding a polypeptide of 435 amino acid residues (SEQ ID NO:18) with a predicted molecular weight of 47162.5 Daltons. The start codon is located at nucleotides 51–53 and the stop codon is located at nucleotides 1356–1358. The protein encoded by clone 21637262.0.64 is predicted by the PSORT program to localize in the cytoplasm with a certainty of 0.4500. The program PSORT and program SignalP predict that the protein appears to have no amino-terminal signal sequence.

Real-time expression analysis was performed on SECP9 (clone 21637262.0.64). The results demonstrate that RNA homologous to this clone is present in multiple tissue and cell types. The relative amounts of RNA in various cell types are shown in FIG. 14 (see also the Examples, below). The cells include myometrium, placenta, uterus, prostate, and testis, and neoplastic cells derived from breast carcinoma (pleural effusion) T47D, breast carcinoma (pleural effusion) MDA-MB-231, breast carcinoma BT-549, ovarian carcinoma OVCAR-3, ovarian carcinoma OVCAR-5, prostate carcinoma (bone metastases) PC-3, melanoma M14, and melanoma LOX IMVI.

Accordingly, SECP9 nucleic acids according to the invention can be used to identify one or more of these cell types. The presence of RNA sequences homologous to a SECP9 nucleic in a sample indicates that the sample contains one or more of the above-cell types.

A search of the sequence databases using BLASTX reveals that clone 21637262.0.64 has 23 of 420 residues (29%) identical to, and 201 of 420 residues (47%) positive with, the 1130 residue murine protein repetin (SWISSPROT-ACC:P97347). Repetin is a member of the "fused gene" subgroup within the S100 gene family that is an epidermal differentiation protein.

The proteins of the invention encoded by clone 21637262.0.64 include the protein disclosed as being encoded by the ORF described herein, as well as any mature protein arising therefrom as a result of post-translational modifications. Thus, the proteins of the invention encompass both a precursor and any active forms of the clone 21637262.0.64 protein.

SECP Nucleic Acids

The novel nucleic acids of the invention include those that encode a SECP or SECP-like protein, or biologically-active portions thereof. The nucleic acids include nucleic acids encoding polypeptides that include the amino acid sequence of one or more of SEQ ID NO:1, 3, 5, 7, 9, 11, 13, 15, and/or 17. The encoded polypeptides can thus include, e.g., the amino acid sequences of SEQ ID NO: 2, 4, 6, 8, 10, 12, 14, 16, and/or 18.

In some embodiments, a SECP polypeptide or protein, as disclosed herein, includes the product of a naturally-occurring polypeptide, precursor form, pro-protein, or mature form of the polypeptide. The naturally-occurring polypeptide, precursor, or pro-protein includes, e.g., the full-length gene product, encoded by the corresponding gene. The naturally-occurring polypeptide also includes the polypeptide, precursor or pro-protein encoded by an open reading frame (ORF) described herein. As used herein, the term "identical" residues corresponds to those residues in a comparison between two sequences where the equivalent nucleotide base or amino acid residue in an alignment of two sequences is the same residue. Residues are alternatively described as "similar" or "positive" when the comparisons between two sequences in an alignment show that residues in an equivalent position in a comparison are either the same amino acid residue or a conserved amino acid residue, as defined below.

As used herein, a "mature" form of a polypeptide or protein disclosed in the present invention is the product of a naturally occurring polypeptide or precursor form or pro-protein. The naturally occurring polypeptide, precursor or proprotein includes, by way of nonlimiting example, the full length gene product, encoded by the corresponding gene. Alternatively, it may be defined as the polypeptide, precursor or proprotein encoded by an open reading frame described herein. The product "mature" form arises, again by way of nonlimiting example, as a result of one or more naturally occurring processing steps as they may take place within the cell, or host cell, in which the gene product arises. Examples of such processing steps leading to a "mature" form of a polypeptide or protein include the cleavage of the amino-terminal methionine residue encoded by the initiation codon of an open reading frame, or the proteolytic cleavage of a signal peptide or leader sequence. Thus, a mature form arising from a precursor polypeptide or protein that has residues 1 to N, where residue 1 is the amino-terminal methionine, would have residues 2 through N remaining after removal of the amino-terminal methionine. Alternatively, a mature form arising from a precursor polypeptide or protein having residues 1 to N, in which an amino-terminal signal sequence from residue 1 to residue M is cleaved, would have the residues from residue M+1 to residue N remaining. Further, as used herein, a "mature" form of a polypeptide or protein may arise from a step of post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

In some embodiments, a nucleic acid encoding a polypeptide having the amino acid sequence of one or more of SEQ ID NO:2, 4, 6, 8, 10, 12, 14, 16, and/or 18, includes the nucleic acid sequence of any of SEQ ID NO:1, 3, 5, 7, 9, 11, 13, 15, and/or 17, or a fragment thereof. Additionally, the invention includes mutant or variant nucleic acids of any of SEQ ID NO:1, 3, 5, 7, 9, 11, 13, 15, and/or 17, or a fragment thereof, any of whose bases may be changed from the disclosed sequence while still encoding a protein that maintains its SECP-like biological activities and physiological functions. The invention further includes the complement of the nucleic acid sequence of any of SEQ ID NO:1, 3, 5, 7, 9, 11, 13, 15, and/or 17, including fragments, derivatives, analogs and homologs thereof. The invention additionally includes nucleic acids or nucleic acid fragments, or complements thereto, whose structures include chemical modifications.

Also included are nucleic acid fragments sufficient for use as hybridization probes to identify SECP-encoding nucleic acids (e.g., SECP mRNA) and fragments for use as polymerase chain reaction (PCR) primers for the amplification or mutation of SECP nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments, and homologs thereof. The nucleic acid molecule can be single-stranded or double-stranded, but preferably is double-stranded DNA.

The term "probes" refer to nucleic acid sequences of variable length, preferably between at least about 10 nucleotides (nt), 100 nt, or as many as about, e.g., 6,000 nt, depending upon the specific use. Probes are used in the detection of identical, similar, or complementary nucleic acid sequences. Longer length probes are usually obtained from a natural or recombinant source, are highly specific and much slower to hybridize than oligomers. Probes may be single- or double-stranded, and may also be designed to have specificity in PCR, membrane-based hybridization technologies, or ELISA-like technologies.

The term "isolated" nucleic acid molecule is a nucleic acid that is separated from other nucleic acid molecules that are present in the natural source of the nucleic acid. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules. Preferably, an "isolated" nucleic acid is free of sequences which naturally flank the nucleic acid (i.e., sequences located at the 5'- and 3'-termini of the nucleic acid) in the genomic DNA of the organism from which the nucleic acid is derived. For example, in various embodiments, the isolated SECP nucleic acid molecule can contain less than approximately 50 kb, 25 kb, 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the invention, e.g., a nucleic acid molecule having the nucleotide sequence of SEQ ID NO:1, 3, 5, 7, 9, 11, 13, 15, and/or 17, or a complement of any of these nucleotide sequences, can be isolated using standard molecular biology techniques and the sequence information provided herein. Using all or a portion of the nucleic acid sequence of any of SEQ ID NO:1, 3, 5, 7, 9, 11, 13, 15, and/or 17 as a hybridization probe, SECP nucleic acid sequences can be isolated using standard hybridization and cloning techniques (e.g., as described in Sambrook et al., eds., MOLECULAR CLONING: A LABORATORY MANUAL 2$^{nd}$ Ed., Cold Spring Harbor Laboratory Press, Cold Spring Harbor, N.Y., 1989; and Ausubel, et al., eds., CURRENT PROTOCOLS IN MOLECULAR BIOLOGY, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to SECP nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment, an oligonucleotide comprising a nucleic acid molecule less than 100 nt in length would further comprise at lease 6 contiguous nucleotides of any of SEQ ID NO:1, 3, 5, 7, 9, 11, 13, 15, and/or 17, or a complement thereof. Oligonucleotides may be chemically synthesized and may also be used as probes.

In another embodiment, an isolated nucleic acid molecule of the invention comprises a nucleic acid molecule that is a complement of the nucleotide sequence shown in any of SEQ ID NO:1, 3, 5, 7, 9, 11, 13, 15, and/or 17. In still another embodiment, an isolated nucleic acid molecule of the invention comprises a nucleic acid molecule that is a complement of the nucleotide sequence shown in any of SEQ ID NO:1, 3, 5, 7, 9, 11, 13, 15, and/or 17, or a portion of this nucleotide sequence. A nucleic acid molecule that is complementary to the nucleotide sequence shown in is one that is sufficiently complementary to the nucleotide sequence shown in of any of SEQ ID NO:1, 3, 5, 7, 9, 11, 13, 15, and/or 17, that it can hydrogen bond with little or no mismatches to the nucleotide sequence shown in of any of SEQ ID NO:1, 3, 5, 7, 9, 11, 13, 15, and/or 17, thereby forming a stable duplex.

As used herein, the term "complementary" refers to Watson-Crick or Hoogsteen base-pairing between nucleotides units of a nucleic acid molecule, whereas the term "binding" is defined as the physical or chemical interaction between two polypeptides or compounds or associated polypeptides or compounds or combinations thereof. Binding includes ionic, non-ionic, Von der Waals, hydrophobic interactions, and the like. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Additionally, the nucleic acid molecule of the invention can comprise only a portion of the nucleic acid sequence of any of SEQ ID NO:1, 3, 5, 7, 9, 11, 13, 15, and/or 17, e.g., a fragment that can be used as a probe or primer, or a fragment encoding a biologically active portion of SECP. Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild-type.

Derivatives and analogs may be full-length or other than full-length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 80%, 85%, 90%, 95%, 98%, or even 99% identity (with a preferred identity of 80–99%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman (Adv. Appl. Math., 1981, 2: 482–489), which is incorporated herein by reference in its entirety.

The term "homologous nucleic acid sequence" or "homologous amino acid sequence," or variations thereof, refer to sequences characterized by a homology at the nucleotide level or amino acid level as previously discussed. Homologous nucleotide sequences encode those sequences coding for isoforms of SECP polypeptide. Isoforms can be expressed in different tissues of the same organism as a result of, e.g., alternative splicing of RNA. Alternatively, isoforms can be encoded by different genes. In the invention, homologous nucleotide sequences include nucleotide sequences encoding for a SECP polypeptide of species other than humans, including, but not limited to, mammals, and thus can include, e.g., mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include the nucleotide sequence encoding human SECP protein. Homologous nucleic acid sequences include those nucleic acid sequences that encode conservative amino acid substitutions (see below) in any of SEQ ID NO:1, 3, 5, 7, 9, 11, 13, 15, and/or 17, as well as a polypeptide having SECP activity. Biological activities of the SECP proteins are described below. A homologous amino acid sequence does not encode the amino acid sequence of a human SECP polypeptide.

The nucleotide sequence determined from the cloning of the human SECP gene allows for the generation of probes and primers designed for use in identifying the cell types disclosed and/or cloning SECP homologues in other cell types, e.g., from other tissues, as well as SECP homologues from other mammals. The probe/primer typically comprises a substantially-purified oligonucleotide. The oligonucleotide typically comprises a region of nucleotide sequence that hybridizes under stringent conditions to at least about 12, 25, 50, 100, 150, 200, 250, 300, 350 or 400 or more consecutive sense strand nucleotide sequence of SEQ ID NO:1, 3, 5, 7, 9, 11, 13, 15, and/or 17; or an anti-sense strand nucleotide sequence of SEQ ID NO:1, 3, 5, 7, 9, 11, 13, 15, and/or 17; or of a naturally occurring mutant of SEQ ID NO:1, 3, 5, 7, 9, 11, 13, 15, and/or 17.

Probes based upon the human SECP nucleotide sequence can be used to detect transcripts or genomic sequences encoding the same or homologous proteins. In various embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which mis-express a SECP protein, such as by measuring a level of a SECP-encoding nucleic acid in a sample of cells from a subject e.g., detecting SECP mRNA levels or determining whether a genomic SECP gene has been mutated or deleted.

The term "a polypeptide having a biologically-active portion of SECP" refers to polypeptides exhibiting activity similar, but not necessarily identical to, an activity of a polypeptide of the invention, including mature forms, as measured in a particular biological assay, with or without dose dependency. A nucleic acid fragment encoding a "biologically-active portion of SECP" can be prepared by isolating a portion of SEQ ID NO:1, 3, 5, 7, 9, 11, 13, 15, and/or 17, that encodes a polypeptide having a SECP biological activity, expressing the encoded portion of SECP protein (e.g., by recombinant expression in vitro), and assessing the activity of the encoded portion of SECP.

SECP Variants

The invention further encompasses nucleic acid molecules that differ from the disclosed SECP nucleotide sequences due to degeneracy of the genetic code. These nucleic acids therefore encode the same SECP protein as those encoded by the nucleotide sequence shown in SEQ ID NO:1, 3, 5, 7, 9, 11, 13, 15, and/or 17. In another embodiment, an isolated nucleic acid molecule of the invention has a nucleotide sequence encoding a protein having an amino acid sequence shown in any of SEQ ID NO:1, 3, 5, 7, 9, 11, 13, 15, and/or 17.

In addition to the human SECP nucleotide sequence shown in any of SEQ ID NO:1, 3, 5, 7, 9, 11, 13, 15, and/or 17, it will be appreciated by those skilled in the art that DNA sequence polymorphisms that lead to changes in the amino acid sequences of SECP may exist within a population (e.g., the human population). Such genetic polymorphism in the SECP gene may exist among individuals within a population due to natural allelic variation. As used herein, the terms "gene" and "recombinant gene" refer to nucleic acid molecules comprising an open reading frame encoding a SECP protein, preferably a mammalian SECP protein. Such natural allelic variations can typically result in 1–5% variance in the nucleotide sequence of the SECP gene. Any and all such nucleotide variations and resulting amino acid polymorphisms in SECP that are the result of natural allelic variation and that do not alter the functional activity of SECP are intended to be within the scope of the invention.

Additionally, nucleic acid molecules encoding SECP proteins from other species, and thus that have a nucleotide sequence that differs from the human sequence of any of SEQ ID NO:1, 3, 5, 7, 9, 11, 13, 15, and/or 17, are intended to be within the scope of the invention. Nucleic acid molecules corresponding to natural allelic variants and homologues of the SECP cDNAs of the invention can be isolated based on their homology to the human SECP nucleic acids disclosed herein using the human cDNAs, or a portion thereof, as a hybridization probe according to standard hybridization techniques under stringent hybridization conditions.

In another embodiment, an isolated nucleic acid molecule of the invention is at least 6 nucleotides in length and hybridizes under stringent conditions to the nucleic acid molecule comprising the nucleotide sequence of any of SEQ ID NO:1, 3, 5, 7, 9, 11, 13, 15, and/or 17. In another embodiment, the nucleic acid is at least 10, 25, 50, 100, 250, 500 or 750 nucleotides in length. In yet another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding SECP proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target sequence hybridize to the target sequence at equilibrium. Since the target sequences are generally present at excess, at $T_m$, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in CURRENT PROTOCOLS IN MOLECULAR BIOLOGY, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. An isolated nucleic acid molecule of the invention that hybridizes under stringent conditions to the sequence of any of SEQ ID NO:1, 3, 5, 7, 9, 11, 13, 15, and/or 17 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of any of SEQ ID NO:1, 3, 5, 7, 9, 11, 13, 15, and/or 17, or fragments, analogs or derivatives thereof, under conditions of moderate stringency is provided. A non-limiting example of moderate stringency hybridization conditions are hybridization in 6×SSC, 5× Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well known in the art. See, e.g., Ausubel et al. (eds.), 1993, CURRENT PROTO- COLS IN MOLECULAR BIOLOGY, John Wiley & Sons, NY, and Kriegler, 1990. GENE TRANSFER AND EXPRESSION, A LABORATORY MANUAL, Stockton Press, NY.

In a third embodiment, a nucleic acid that is hybridizable to the nucleic acid molecule comprising the nucleotide sequence of any of SEQ ID NO:1, 3, 5, 7, 9, 11, 13, 15, and/or 17, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel, et al., (eds.), 1993. CURRENT PROTOCOLS IN MOLECULAR BIOLOGY, John Wiley & Sons, NY, and Kriegler, 1990. GENE TRANSFER AND EXPRESSION, A LABORATORY MANUAL, Stockton Press, NY; Shilo and Weinberg, 1981. *Proc. Natl. Acad. Sci. USA* 78: 6789–6792.

Conservative Mutations

In addition to naturally-occurring allelic variants of the SECP sequence that may exist in the population, the skilled artisan will further appreciate that changes can be introduced by mutation into the nucleotide sequence of any of SEQ ID NO:1, 3, 5, 7, 9, 11, 13, 15, and/or 17, thereby leading to changes in the amino acid sequence of the encoded SECP protein, without altering the functional ability of the SECP protein. For example, nucleotide substitutions leading to amino acid substitutions at "non-essential" amino acid residues can be made in the sequence of any of SEQ ID NO:1, 3, 5, 7, 9, 11, 13, 15, and/or 17. A "non-essential" amino acid residue is a residue that can be altered from the wild-type sequence of SECP without altering the biological activity, whereas an "essential" amino acid residue is required for biological activity. For example, amino acid residues that are conserved among the SECP proteins of the invention, are predicted to be particularly non-amenable to such alteration.

Amino acid residues that are conserved among members of a SECP family members are predicted to be less amenable to alteration. For example, a SECP protein according to the invention can contain at least one domain that is a typically conserved region in a SECP family member. As such, these conserved domains are not likely to be amenable to mutation. Other amino acid residues, however, (e.g., those that are not conserved or only semi-conserved among members of the SECP family) may not be as essential for activity and thus are more likely to be amenable to alteration.

Another aspect of the invention pertains to nucleic acid molecules encoding SECP proteins that contain changes in amino acid residues that are not essential for activity. Such SECP proteins differ in amino acid sequence from any of any of SEQ ID NO:2, 4, 6, 8, 10, 12, 14, 16, and/or 18, yet retain biological activity. In one embodiment, the isolated nucleic acid molecule comprises a nucleotide sequence encoding a protein, wherein the protein comprises an amino acid sequence at least about 75% homologous to the amino acid sequence of any of SEQ ID NO:2, 4, 6, 8, 10, 12, 14, 16, and/or 18. Preferably, the protein encoded by the nucleic acid is at least about 80% homologous to any of SEQ ID NO:2, 4, 6, 8, 10, 12, 14, 16, and/or 18, more preferably at least about 90%, 95%, 98%, and most preferably at least about 99% homologous to SEQ ID NO:2, 4, 6, 8, 10, 12, 14, 16, and/or 18.

An isolated nucleic acid molecule encoding a SECP protein homologous to the protein of any of SEQ ID NO:2, 4, 6, 8, 10, 12, 14, 16, and/or 18 can be created by introducing one or more nucleotide substitutions, additions or deletions into the corresponding nucleotide sequence (i.e., SEQ ID NO:1, 3, 5, 7, 9, 11, 13, 15, and/or 17), such that one or more amino acid substitutions, additions or deletions are introduced into the encoded protein.

Mutations can be introduced into SEQ ID NO:1, 3, 5, 7, 9, 11, 13, 15, and/or 17 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Thus, a predicted nonessential amino acid residue in SECP is replaced with another amino acid residue from the same side chain family. Alternatively, in another embodiment, mutations can be introduced randomly along all or part of a SECP coding sequence, such as by saturation mutagenesis, and the resultant mutants can be screened for SECP biological activity to identify mutants that retain activity. Following mutagenesis of SEQ ID NO:1, 3, 5, 7, 9, 11, 13, 15, and/or 17, the encoded protein can be expressed by any recombinant technology known in the art and the activity of the protein can be determined.

In one embodiment, a mutant SECP protein can be assayed for: (i) the ability to form protein:protein interactions with other SECP proteins, other cell-surface proteins, or biologically-active portions thereof; (ii) complex formation between a mutant SECP protein and a SECP receptor; (iii) the ability of a mutant SECP protein to bind to an intracellular target protein or biologically active portion thereof; (e.g., avidin proteins); (iv) the ability to bind BRA protein; or (v) the ability to specifically bind an anti-SECP protein antibody.

Antisense Nucleic Acids

Another aspect of the invention pertains to isolated antisense nucleic acid molecules that are hybridizable to or complementary to the nucleic acid molecule comprising the nucleotide sequence of SEQ ID NO:1, 3, 5, 7, 9, 11, 13, 15, and/or 17, or fragments, analogs or derivatives thereof. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire SECP coding strand, or to only a portion thereof. Nucleic acid molecules encoding fragments, homologs, derivatives and analogs of a SECP protein of any of SEQ ID NO:2, 4, 6, 8, 10, 12, 14, 16, and/or 18 or antisense nucleic acids complementary to a SECP nucleic acid sequence of SEQ ID NO:2, 4, 6, 8, 10, 12, 14, 16, and/or 18, are additionally provided.

In one embodiment, an antisense nucleic acid molecule is antisense to a "coding region" of the coding strand of a nucleotide sequence encoding SECP. The term "coding region" refers to the region of the nucleotide sequence comprising codons which are translated into amino acid residues (e.g., the protein coding region of a human SECP that corresponds to any of SEQ ID NO:2, 4, 6, 8, 10, 12, 14, 16, and/or 18. In another embodiment, the antisense nucleic acid molecule is antisense to a "non-coding region" of the coding strand of a nucleotide sequence encoding SECP. The term "non-coding region" refers to 5'- and 3'-terminal sequences which flank the coding region that are not translated into amino acids (i.e., also referred to as 5' and 3' non-translated regions).

Given the coding strand sequences encoding the SECP proteins disclosed herein (e.g., SEQ ID NO:1, 3, 5, 7, 9, 11, 13, 15, and/or 17), antisense nucleic acids of the invention can be designed according to the rules of Watson and Crick or Hoogsteen base-pairing. The antisense nucleic acid molecule can be complementary to the entire coding region of SECP mRNA, but more preferably is an oligonucleotide that is antisense to only a portion of the coding or non-coding region of SECP mRNA. For example, the antisense oligonucleotide can be complementary to the region surrounding the translation start site of SECP mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally-occurring nucleotides or variously modified nucleotides designed to increase the biological stability of the molecules or to increase the physical stability of the duplex formed between the antisense and sense nucleic acids, e.g., phosphorothioate derivatives and acridine-substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a SECP protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface (e.g., by linking the antisense nucleic acid molecules to peptides or antibodies that bind to cell surface receptors or antigens). The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual α-units, the strands run parallel to each other (see, Gaultier, et al., 1987. *Nucl. Acids Res.* 15: 6625–6641). The antisense nucleic acid molecule can also comprise a 2'-o-methylribonucleotide (Inoue, et al., 1987. *Nucl. Acids Res.* 15: 6131–6148) or a chimeric RNA-DNA analogue (Inoue, et al., 1987. *FEBS Lett.* 215: 327–330).

Ribozymes and PNA Moieties

Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

In still another embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes; described by Haselhoff and Gerlach, 1988. *Nature* 334: 585–591) can be used to catalytically-cleave SECP mRNA transcripts to thereby inhibit translation of SECP mRNA. A ribozyme having specificity for a SECP-encoding nucleic acid can be designed based upon the nucleotide sequence of a SECP DNA disclosed herein (i.e., SEQ ID NO:1, 3, 5, 7, 9, 11, 13, 15, and/or 17). For example, a derivative of a *Tetrahymena* L-19 IVS RNA can be constructed in which the nucleotide sequence of the active site is complementary to the nucleotide sequence to be cleaved in a SECP-encoding mRNA. See, e.g., Cech, et al., U.S. Pat. No. 4,987,071; and Cech, et al., U.S. Pat. No. 5,116,742. Alternatively, SECP mRNA can be used to select a catalytic RNA having a specific ribonuclease activity from a pool of RNA molecules (Bartel, et al., 1993. *Science* 261: 1411–1418).

Alternatively, SECP gene expression can be inhibited by targeting nucleotide sequences complementary to the regulatory region of the SECP (e.g., the SECP promoter and/or enhancers) to form triple helical structures that prevent transcription of the SECP gene in target cells. See, e.g., Helene, 1991. *Anticancer Drug Des.* 6: 569–84; Helene, et al., 1992. *Ann. N.Y. Acad. Sci.* 660: 27–36; and Maher, 1992. *Bioassays* 14: 807–15.

In various embodiments, the nucleic acids of SECP can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (Hyrup, et al., 1996. *Bioorg. Med. Chem.* 4: 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup, et al., 1996. supra; Perry-O'Keefe, et al., 1996. *Proc. Natl. Acad. Sci. USA* 93: 14670–14675.

PNAs of SECP can be used in therapeutic and diagnostic applications. For example, PNAs can be used as antisense or antigene agents for sequence-specific modulation of gene expression by, e.g., inducing transcription or translation arrest or inhibiting replication. PNAs of SECP can also be used, e.g., in the analysis of single base pair mutations in a gene by, e.g., PNA directed PCR clamping; as artificial restriction enzymes when used in combination with other enzymes, e.g., S1 nucleases (see, Hyrup, 1996., supra); or as probes or primers for DNA sequence and hybridization (see, Hyrup, et al., 1996.; Perry-O'Keefe, 1996., supra).

In another embodiment, PNAs of SECP can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of SECP can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (see, Hyrup, 1996., supra). The synthesis of PNA-DNA chimeras can be performed as described in Finn, et al., (1996. *Nucl. Acids Res.* 24: 3357–3363). For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA (Mag, et al., 1989. *Nucl. Acid Res.* 17: 5973–5988). PNA monomers are then coupled in a stepwise manner to produce a chimeric molecule with a 5' PNA segment and a 3' DNA segment (see, Finn, et al., 1996., supra). Alternatively, chimeric molecules can be synthesized with a 5' DNA segment and a 3' PNA segment. See, e.g., Petersen, et al., 1975. *Bioorg. Med. Chem. Lett.* 5: 1119–11124.

In other embodiments, the oligonucleotide may include other appended groups such as peptides (e.g., for targeting host cell receptors in vivo), or agents facilitating transport across the cell membrane (see, e.g., Letsinger, et al., 1989. *Proc. Natl. Acad. Sci. U.S.A.* 86: 6553–6556; Lemaitre, et al., 1987. *Proc. Natl. Acad. Sci.* 84: 648–652; PCT Publication No. WO88/09810) or the blood-brain barrier (see, e.g., PCT Publication No. WO 89/10134). In addition, oligonucleotides can be modified with hybridization triggered cleavage agents (see, e.g., Krol, et al., 1988. *BioTechniques* 6:958–976) or intercalating agents (see, e.g., Zon, 1988. *Pharm. Res.* 5: 539–549). To this end, the oligonucleotide may be conjugated to another molecule, e.g., a peptide, a hybridization triggered cross-linking agent, a transport agent, a hybridization-triggered cleavage agent, and the like.

Characterization of SECP Polypeptides

A polypeptide according to the invention includes a polypeptide including the amino acid sequence of SECP polypeptides whose sequences are provided in SEQ ID NO:2, 4, 6, 8, 10, 12, 14, 16, and/or 18. The invention also includes a mutant or variant protein any of whose residues may be changed from the corresponding residues shown in SEQ ID NO:2, 4, 6, 8, 10, 12, 14, 16, and/or 18, while still encoding a protein that maintains its SECP activities and physiological functions, or a functional fragment thereof.

In general, a SECP variant that preserves SECP-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated SECP proteins, and biologically-active portions thereof, or derivatives, fragments, analogs or homologs thereof. Also provided are polypeptide fragments suitable for use as immunogens to raise anti-SECP antibodies. In one embodiment, native SECP proteins can be isolated from cells or tissue sources by an appropriate purification scheme using standard protein purification techniques. In another embodiment, SECP proteins are produced by recombinant DNA techniques. Alternative to recombinant expression, a SECP protein or polypeptide can be synthesized chemically using standard peptide synthesis techniques.

An "isolated" or "purified" polypeptide or protein or biologically-active portion thereof is substantially free of cellular material or other contaminating proteins from the cell or tissue source from which the SECP protein is derived, or substantially free from chemical precursors or other chemicals when chemically synthesized. The language "substantially free of cellular material" includes preparations of SECP proteins in which the protein is separated from cellular components of the cells from which it is isolated or recombinantly-produced. In one embodiment, the language "substantially free of cellular material" includes preparations of SECP proteins having less than about 30% (by dry weight) of non-SECP proteins (also referred to herein as a "contaminating protein"), more preferably less than about 20% of non-SECP proteins, still more preferably less than about 10% of non-SECP proteins, and most preferably less than about 5% of non-SECP proteins. When the SECP protein or biologically-active portion thereof is recombinantly-produced, it is also preferably substantially free of culture medium, i.e., culture medium represents less than about 20%, more preferably less than about 10%, and most preferably less than about 5% of the volume of the SECP protein preparation.

The phrase "substantially free of chemical precursors or other chemicals" includes preparations of SECP protein in which the protein is separated from chemical precursors or other chemicals that are involved in the synthesis of the protein. In one embodiment, the language "substantially free of chemical precursors or other chemicals" includes preparations of SECP protein having less than about 30% (by dry weight) of chemical precursors or non-SECP chemicals, more preferably less than about 20% chemical precursors or non-SECP chemicals, still more preferably less than about 10% chemical precursors or non-SECP chemicals, and most preferably less than about 5% chemical precursors or non-SECP chemicals.

Biologically-active portions of a SECP protein include peptides comprising amino acid sequences sufficiently homologous to or derived from the amino acid sequence of the SECP protein which include fewer amino acids than the full-length SECP proteins, and exhibit at least one activity of a SECP protein. Typically, biologically-active portions comprise a domain or motif with at least one activity of the SECP protein. A biologically-active portion of a SECP protein can be a polypeptide which is, for example, 10, 25, 50, 100 or more amino acids in length.

A biologically-active portion of a SECP protein of the invention may contain at least one of the above-identified conserved domains. Moreover, other biologically active portions, in which other regions of the protein are deleted, can be prepared by recombinant techniques and evaluated for one or more of the functional activities of a native SECP protein.

In an embodiment, the SECP protein has an amino acid sequence shown in any of SEQ ID NO:1, 3, 5, 7, 9, 11, 13, 15, and/or 17. In other embodiments, the SECP protein is substantially homologous to any of SEQ ID NO:1, 3, 5, 7, 9, 11, 13, 15, and/or 17, and retains the functional activity of the protein of any of SEQ ID NO:1, 3, 5, 7, 9, 11, 13, 15, and/or 17, yet differs in amino acid sequence due to natural allelic variation or mutagenesis, as described in detail below. Accordingly, in another embodiment, the SECP protein is a protein that comprises an amino acid sequence at least about 45% homologous, and more preferably about 55, 65, 70, 75, 80, 85, 90, 95, 98 or even 99% homologous to the amino acid sequence of any of SEQ ID NO:1, 3, 5, 7, 9, 11, 13, 15, and/or 17 and retains the functional activity of the SECP proteins of the corresponding polypeptide having the sequence of SEQ ID NO:1, 3, 5, 7, 9, 11, 13, 15, and/or 17.

Determining Homology Between Two or More Sequences

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch, 1970. *J. Mol. Biol.* 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NO:1, 3, 5, 7, 9, 11, 13, 15, and/or 17.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

Chimeric and Fusion Proteins

The invention also provides SECP chimeric or fusion proteins. As used herein, a SECP "chimeric protein" or "fusion protein" comprises a SECP polypeptide operatively-linked to a non-SECP polypeptide. An "SECP polypeptide" refers to a polypeptide having an amino acid sequence corresponding to a SECP protein shown in SEQ ID NO:2, 4, 6, 8, 10, 12, 14, 16, and/or 18, whereas a "non-SECP polypeptide" refers to a polypeptide having an amino acid sequence corresponding to a protein that is not substantially homologous to the SECP protein (e.g., a protein that is different from the SECP protein and that is derived from the same or a different organism). Within a SECP fusion protein the SECP polypeptide can correspond to all or a portion of a SECP protein. In one embodiment, a SECP fusion protein comprises at least one biologically-active portion of a SECP protein. In another embodiment, a SECP fusion protein comprises at least two biologically-active portions of a SECP protein. In yet another embodiment, a SECP fusion protein comprises at least three biologically-active portions of a SECP protein. Within the fusion protein, the term "operatively-linked" is intended to indicate that the SECP polypeptide and the non-SECP polypeptide are fused in-frame with one another. The non-SECP polypeptide can be fused to the amino-terminus or carboxyl-terminus of the SECP polypeptide.

In one embodiment, the fusion protein is a GST-SECP fusion protein in which the SECP sequences are fused to the carboxyl-terminus of the GST (glutathione S-transferase) sequences. Such fusion proteins can facilitate the purification of recombinant SECP polypeptides.

In another embodiment, the fusion protein is a SECP protein containing a heterologous signal sequence at its amino-terminus. In certain host cells (e.g., mammalian host cells), expression and/or secretion of SECP can be increased through use of a heterologous signal sequence.

In yet another embodiment, the fusion protein is a SECP-immunoglobulin fusion protein in which the SECP sequences are fused to sequences derived from a member of the immunoglobulin protein family. The SECP-immunoglobulin fusion proteins of the invention can be incorporated into pharmaceutical compositions and administered to a subject to inhibit an interaction between a SECP ligand and a SECP protein on the surface of a cell, to thereby suppress SECP-mediated signal transduction in vivo. The SECP-immunoglobulin fusion proteins can be used to affect the bioavailability of a SECP cognate ligand. Inhibition of the SECP ligand/SECP interaction may be useful therapeutically for both the treatment of proliferative and differentiative disorders, as well as modulating (e.g., promoting or inhibiting) cell survival. Moreover, the SECP-immunoglobulin fusion proteins of the invention can be used as immunogens to produce anti-SECP antibodies in a subject, to purify SECP ligands, and in screening assays to identify molecules that inhibit the interaction of SECP with a SECP ligand.

A SECP chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g. Ausubel, et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A SECP-encoding nucleic acid can be cloned into such an expression vector such that the fusion moiety is linked in-frame to the SECP protein.

SECP Agonists and Antagonists

The invention also pertains to variants of the SECP proteins that function as either SECP agonists (i.e., mimetics) or as SECP antagonists. Variants of the SECP protein can be generated by mutagenesis (e.g., discrete point mutation or truncation of the SECP protein). An agonist of a SECP protein can retain substantially the same, or a subset of, the biological activities of the naturally-occurring form of a SECP protein. An antagonist of a SECP protein can inhibit one or more of the activities of the naturally occurring form of a SECP protein by, for example, competitively binding to a downstream or upstream member of a cellular signaling cascade which includes the SECP protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the SECP proteins.

Variants of the SECP proteins that function as either SECP agonists (ie., mimetics) or as SECP antagonists can be identified by screening combinatorial libraries of mutants (e.g., truncation mutants) of the SECP proteins for SECP protein agonist or antagonist activity. In one embodiment, a variegated library of SECP variants is generated by combinatorial mutagenesis at the nucleic acid level and is encoded by a variegated gene library. A variegated library of SECP variants can be produced by, for example, enzymatically-ligating a mixture of synthetic oligonucleotides into gene sequences such that a degenerate set of potential SECP sequences is expressible as individual polypeptides, or alternatively, as a set of larger fusion proteins (e.g., for phage display) containing the set of SECP sequences therein. There are a variety of methods which can be used to produce libraries of potential SECP variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential SECP sequences. Methods for synthesizing degenerate oligonucleotides are well-known within the art. See, e.g., Narang, 1983. *Tetrahedron* 39: 3; Itakura, et al., 1984. *Annu. Rev. Biochem.* 53: 323; Itakura, et al., 1984. *Science* 198: 1056; Ike, et al., 1983. *Nucl. Acids Res.* 11: 477.

Polypeptide Libraries

In addition, libraries of fragments of the SECP protein coding sequences can be used to generate a variegated population of SECP fragments for screening and subsequent selection of variants of a SECP protein. In one embodiment, a library of coding sequence fragments can be generated by treating a double-stranded PCR fragment of a SECP coding sequence with a nuclease under conditions wherein nicking occurs only about once per molecule, denaturing the double stranded DNA, renaturing the DNA to form double-stranded DNA that can include sense/antisense pairs from different nicked products, removing single stranded portions from reformed duplexes by treatment with $S_1$ nuclease, and ligating the resulting fragment library into an expression vector. By this method, expression libraries can be derived which encodes amino-terminal and internal fragments of various sizes of the SECP proteins.

Various techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of SECP proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify SECP variants. See, e.g., Arkin and Yourvan, 1992. *Proc. Natl. Acad. Sci. USA* 89: 7811–7815; Delgrave, et al., 1993. *Protein Engineering* 6:327–331.

Anti-SECP Antibodies

The invention encompasses antibodies and antibody fragments, such as $F_{ab}$ or $(F_{ab})_2$, that bind immunospecifically to any of the SECP polypeptides of said invention.

An isolated SECP protein, or a portion or fragment thereof, can be used as an immunogen to generate antibodies that bind to SECP polypeptides using standard techniques for polyclonal and monoclonal antibody preparation. The full-length SECP proteins can be used or, alternatively, the invention provides antigenic peptide fragments of SECP proteins for use as immunogens. The antigenic SECP peptides comprises at least 4 amino acid residues of the amino acid sequence shown in SEQ ID NO:2, 4, 6, 8, 10, 12, 14, 16, and/or 18, and encompasses an epitope of SECP such that an antibody raised against the peptide forms a specific immune complex with SECP. Preferably, the antigenic peptide comprises at least 6, 8, 10, 15, 20, or 30 amino acid residues. Longer antigenic peptides are sometimes preferable over shorter antigenic peptides, depending on use and according to methods well known to someone skilled in the art.

In certain embodiments of the invention, at least one epitope encompassed by the antigenic peptide is a region of SECP that is located on the surface of the protein (e.g., a hydrophilic region). As a means for targeting antibody production, hydropathy plots showing regions of hydrophilicity and hydrophobicity may be generated by any method well known in the art, including, for example, the Kyte-Doolittle or the Hopp-Woods methods, either with or without Fourier transformation (see, e.g., Hopp and Woods, 1981. *Proc. Nat. Acad. Sci. USA* 78: 3824–3828; Kyte and Doolittle, 1982. *J. Mol. Biol.* 157: 105–142, each incorporated herein by reference in their entirety).

As disclosed herein, SECP protein sequences of SEQ ID NO:2, 4, 6, 8, 10, 12, 14, 16, and/or 18, or derivatives, fragments, analogs, or homologs thereof, may be utilized as immunogens in the generation of antibodies that immunospecifically-bind these protein components. The term "antibody" as used herein refers to immunoglobulin molecules and immunologically-active portions of immunoglobulin molecules, i.e., molecules that contain an antigen binding site that specifically-binds (immunoreacts with) an antigen, such as SECP. Such antibodies include, but are not limited to, polyclonal, monoclonal, chimeric, single chain, $F_{ab}$ and $F_{(ab)2}$ fragments, and an $F_{ab}$ expression library. In a specific embodiment, antibodies to human SECP proteins are disclosed. Various procedures known within the art may be used for the production of polyclonal or monoclonal antibodies to a SECP protein sequence of SEQ ID NO:2, 4, 6, 8, 10, 12, 14, 16, and/or 18, or a derivative, fragment, analog, or homolog thereof.

For the production of polyclonal antibodies, various suitable host animals (e.g., rabbit, goat, mouse or other mammal) may be immunized by injection with the native protein, or a synthetic variant thereof, or a derivative of the foregoing. An appropriate immunogenic preparation can contain, for example, recombinantly-expressed SECP protein or a chemically-synthesized SECP polypeptide. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as *Bacille Calmette-Guerin* and *Corynebacterium parvum*, or similar immunostimulatory agents. If desired, the antibody molecules directed against SECP can be isolated from the mammal (e.g., from the blood) and further purified by well known techniques, such as protein A chromatography to obtain the IgG fraction.

The term "monoclonal antibody" or "monoclonal antibody composition", as used herein, refers to a population of antibody molecules that contain only one species of an antigen binding site capable of immunoreacting with a particular epitope of SECP. A monoclonal antibody composition thus typically displays a single binding affinity for a particular SECP protein with which it immunoreacts. For preparation of monoclonal antibodies directed towards a particular SECP protein, or derivatives, fragments, analogs or homologs thereof, any technique that provides for the production of antibody molecules by continuous cell line culture may be utilized. Such techniques include, but are not limited to, the hybridoma technique (see, e.g., Kohler & Milstein, 1975. *Nature* 256: 495–497); the trioma technique; the human B-cell hybridoma technique (see, e.g., Kozbor, et al., 1983. *Immunol. Today* 4: 72) and the EBV hybridoma technique to produce human monoclonal antibodies (see, e.g., Cole, et al., 1985. In: MONOCLONAL ANTIBODIES AND CANCER THERAPY, Alan R. Liss, Inc., pp. 77–96). Human monoclonal antibodies may be utilized in the practice of the invention and may be produced by using human hybridomas (see, e.g., Cote, et al., 1983. *Proc Natl Acad Sci USA* 80: 2026–2030) or by transforming human B-cells with Epstein Barr Virus in vitro (see, e.g., Cole, et al., 1985. In: MONOCLONAL ANTIBODIES AND CANCER THERAPY, Alan R. Liss, Inc., pp. 77–96). Each of the above citations is incorporated herein by reference in their entirety.

According to the invention, techniques can be adapted for the production of single-chain antibodies specific to a SECP protein (see, e.g. U.S. Pat. No. 4,946,778). In addition, methods can be adapted for the construction of $F_{ab}$ expression libraries (see, e.g., Huse, et al., 1989. *Science* 246: 1275–1281) to allow rapid and effective identification of monoclonal $F_{ab}$ fragments with the desired specificity for a SECP protein or derivatives, fragments, analogs or homologs thereof. Non-human antibodies can be "humanized" by techniques well known in the art. See, e.g., U.S. Pat. No. 5,225,539. Antibody fragments that contain the idiotypes to a SECP protein may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Additionally, recombinant anti-SECP antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in International Application No. PCT/US86/02269; European Patent Application No. 184,187; European Patent Application No. 171,496; European Patent Application No. 173,494; PCT International Publication No. WO 86/01533; U.S. Pat. No. 4,816,567; U.S. Pat. No. 5,225,539; European Patent Application No. 125,023; Better, et al., 1988. *Science* 240: 1041–1043; Liu, et al., 1987. *Proc. Natl. Acad. Sci. USA* 84: 3439–3443; Liu, et al., 1987. *J. Immunol.* 139: 3521–3526; Sun, et al., 1987. *Proc. Natl. Acad. Sci. USA* 84: 214–218; Nishimura, et al., 1987. *Cancer Res.* 47: 999–1005; Wood, et al., 1985. *Nature* 314:446–449; Shaw, et al., 1988. *J. Natl. Cancer Inst.* 80: 1553–1559); Morrison (1985) *Science* 229:1202–1207; Oi, et al. (1986) *BioTechniques* 4:214; Jones, et al., 1986. *Nature* 321: 552–525; Verhoeyan, et al., 1988. *Science* 239: 1534; and Beidler, et al., 1988. *J. Immunol.* 141: 4053–4060. Each of the above citations are incorporated herein by reference in their entirety.

In one embodiment, methods for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of a SECP protein is facilitated by generation of hybridomas that bind to the fragment of a SECP protein possessing such a domain. Thus, antibodies that are specific for a desired domain within a SECP protein, or derivatives, fragments, analogs or homologs thereof, are also provided herein.

Anti-SECP antibodies may be used in methods known within the art relating to the localization and/or quantitation of a SECP protein (e.g., for use in measuring levels of the SECP protein within appropriate physiological samples, for use in diagnostic methods, for use in imaging the protein, and the like). In a given embodiment, antibodies for SECP proteins, or derivatives, fragments, analogs or homologs thereof, that contain the antibody derived binding domain, are utilized as pharmacologically-active compounds (hereinafter "Therapeutics").

An anti-SECP antibody (e.g., monoclonal antibody) can be used to isolate a SECP polypeptide by standard techniques, such as affinity chromatography or immunoprecipitation. An anti-SECP antibody can facilitate the purification of natural SECP polypeptide from cells and of recombinantly-produced SECP polypeptide expressed in host cells. Moreover, an anti-SECP antibody can be used to detect SECP protein (e.g., in a cellular lysate or cell supernatant) in order to evaluate the abundance and pattern of expression of the SECP protein. Anti-SECP antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

SECP Recombinant Expression Vectors and Host Cells

Another aspect of the invention pertains to vectors, preferably expression vectors, containing a nucleic acid encoding a SECP protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present Specification, "plasmid" and "vector" can be used interchangeably, as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The phrase "regulatory sequence" is intended to includes promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., SECP proteins, mutant forms of SECP proteins, fusion proteins, etc.).

The recombinant expression vectors of the invention can be designed for expression of SECP proteins in prokaryotic or eukaryotic cells. For example, SECP proteins can be expressed in bacterial cells such as *Escherichia coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using $T_7$ promoter regulatory sequences and $T_7$ polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor $X_a$, thrombin, and enterokinase. Typical fusion expression vectors include pGEX (Pharmacia Biotech Inc; Smith and Johnson, 1988. *Gene* 67: 31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *Escherichia coli* expression vectors include pTrc (Amrann et al., (1988) *Gene* 69:301–315) and pET 11d (Studier, et al., GENE EXPRESSION TECHNOLOGY: METHODS IN ENZYMOLOGY 185, Academic Press, San Diego, Calif. (1990) 60–89).

One strategy to maximize recombinant protein expression in *Escherichia coli* is to express the protein in a host bacteria with an impaired capacity to proteolytically-cleave the recombinant protein. See, e.g., Gottesman, GENE EXPRESSION TECHNOLOGY: METHODS IN ENZYMOLOGY 185, Academic Press, San Diego, Calif. (1990) 119–128. Another strategy is to alter the nucleic acid sequence of the nucleic acid to be inserted into an expression vector so that the individual codons for each amino acid are those preferentially utilized in Escherichia coli (see, e.g., Wada, et al., 1992. Nucl. Acids Res. 20: 2111–2118). Such alteration of nucleic acid sequences of the invention can be carried out by standard DNA synthesis techniques.

In another embodiment, the SECP expression vector is a yeast expression vector. Examples of vectors for expression in yeast Saccharomyces cerivisae include pYepSec1 (Baldari, et al., 1987. EMBO J. 6: 229–234), pMFa (Kurjan and Herskowitz, 1982. Cell 30: 933–943), pJRY88 (Schultz et al., 1987. Gene 54: 113–123), pYES2 (Invitrogen Corporation, San Diego, Calif.), and picZ (In Vitrogen, Corp.; San Diego, Calif.).

Alternatively, SECP can be expressed in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156–2165) and the pVL series (Lucklow and Summers, 1989. Virology 170: 31–39).

In yet another embodiment, a nucleic acid of the invention is expressed in mammalian cells using a mammalian expression vector. Examples of mammalian expression vectors include pCDM8 (Seed, 1987. Nature 329: 840) and pMT2PC (Kaufman, et al., 1987. EMBO J. 6: 187–195). When used in mammalian cells, the expression vector's control functions are often provided by viral regulatory elements. For example, commonly used promoters are derived from polyoma, adenovirus 2, cytomegalovirus, and simian virus 40 (SV 40). For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; see, Pinkert, et al., 1987. Genes Dev. 1: 268–277), lymphoid-specific promoters (see, Calame and Eaton, 1988. Adv. Immunol. 43: 235–275), in particular promoters of T cell receptors (see, Winoto and Baltimore, 1989. EMBO J. 8: 729–733) and immunoglobulins (see, Banerji, et al., 1983. Cell 33: 729–740; Queen and Baltimore, 1983. Cell 33: 741–748), neuron-specific promoters (e.g., the neurofilament promoter; see, Byrne and Ruddle, 1989. Proc. Natl. Acad. Sci. USA 86: 5473–5477), pancreas-specific promoters (see, Edlund, et al., 1985. Science 230: 912–916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374–379) and the α-fetoprotein promoter (see, Campes and Tilghman, 1989. Genes Dev. 3: 537–546).

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to SECP mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," Reviews-Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, SECP protein can be expressed in bacterial cells such as Escherichia coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding SECP or can be introduced on a separate vector. Cells stably-transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) SECP protein. Accordingly, the invention further provides methods for producing SECP protein using the host cells of the invention. In one embodiment, the method comprises culturing the host cell of invention (i.e., into which a recombinant expression vector encoding SECP protein has been introduced) in a suitable medium such that SECP protein is produced. In another embodiment, the method further comprises isolating SECP protein from the medium or the host cell.

Transgenic Animals

The host cells of the invention can also be used to produce non-human transgenic animals. For example, in one embodiment, a host cell of the invention is a fertilized oocyte or an embryonic stem cell into which SECP protein-coding sequences have been introduced. These host cells can then be used to create non-human transgenic animals in which exogenous SECP sequences have been introduced into their genome or homologous recombinant animals in which endogenous SECP sequences have been altered. Such animals are useful for studying the function and/or activity of SECP protein and for identifying and/or evaluating modulators of SECP protein activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous SECP gene has been altered by homologous recombination between the endogenous gene and an exogenous DNA molecule introduced into a cell of the animal, e.g., an embryonic cell of the animal, prior to development of the animal.

A transgenic animal of the invention can be created by introducing SECP-encoding nucleic acid into the male pronuclei of a fertilized oocyte (e.g., by micro-injection, retroviral infection) and allowing the oocyte to develop in a pseudopregnant female foster animal. The human SECP cDNA sequences of SEQ ID NO:1, 3, 5, 7, 9, 11, 13, 15, and/or 17, can be introduced as a transgene into the genome of a non-human animal. Alternatively, a non-human homologue of the human SECP gene, such as a mouse SECP gene, can be isolated based on hybridization to the human SECP cDNA (described further supra) and used as a transgene. Intronic sequences and polyadenylation signals can also be included in the transgene to increase the efficiency of expression of the transgene. A tissue-specific regulatory sequencers) can be operably-linked to the SECP transgene to direct expression of SECP protein to particular cells. Methods for generating transgenic animals via embryo manipulation and micro-injection, particularly animals such as mice, have become conventional in the art and are described, for example, in U.S. Pat. Nos. 4,736,866; 4,870,009; and 4,873,191; and Hogan, 1986. In: MANIPULATING THE MOUSE EMBRYO, Cold Spring Harbor Laboratory Press, Cold Spring Harbor, N.Y. Similar methods are used for production of other transgenic animals. A transgenic founder animal can be identified based upon the presence of the SECP transgene in its genome and/or expression of SECP mRNA in tissues or cells of the animals. A transgenic founder animal can then be used to breed additional animals carrying the transgene. Moreover, transgenic animals carrying a transgene-encoding SECP protein can further be bred to other transgenic animals carrying other transgenes.

To create a homologous recombinant animal, a vector is prepared which contains at least a portion of a SECP gene into which a deletion, addition or substitution has been introduced to thereby alter, e.g., functionally disrupt, the SECP gene. The SECP gene can be a human gene (e.g., the cDNA of SEQ ID NO:1, 3, 5, 7, 9, 11, 13, 15, and/or 17), but more preferably, is a non-human homologue of a human SECP gene. For example, a mouse homologue of human SECP gene of SEQ ID NO:1, 3, 5, 7, 9, 11, 13, 15, and/or 17, can be used to construct a homologous recombination vector suitable for altering an endogenous SECP gene in the mouse genome. In one embodiment, the vector is designed such that, upon homologous recombination, the endogenous SECP gene is functionally disrupted (i.e., no longer encodes a functional protein; also referred to as a "knock out" vector).

Alternatively, the vector can be designed such that, upon homologous recombination, the endogenous SECP gene is mutated or otherwise altered but still encodes functional protein (e.g., the upstream regulatory region can be altered to thereby alter the expression of the endogenous SECP protein). In the homologous recombination vector, the altered portion of the SECP gene is flanked at its 5'- and 3'-termini by additional nucleic acid of the SECP gene to allow for homologous recombination to occur between the exogenous SECP gene carried by the vector and an endogenous SECP gene in an embryonic stem cell. The additional flanking SECP nucleic acid is of sufficient length for successful homologous recombination with the endogenous gene. Typically, several kilobases (Kb) of flanking DNA (both at the 5'- and 3'-termini) are included in the vector. See, e.g., Thomas, et al., 1987. Cell 51: 503 for a description of homologous recombination vectors. The vector is ten introduced into an embryonic stem cell line (e.g., by electroporation) and cells in which the introduced SECP gene has homologously-recombined with the endogenous SECP gene are selected. See, e.g., Li, et al., 1992. Cell 69: 915.

The selected cells are then micro-injected into a blastocyst of an animal (e.g., a mouse) to form aggregation chimeras. See, e.g., Bradley, 1987. In: TERATOCARCINOMAS AND EMBRYONIC STEM CELLS: A PRACTICAL APPROACH, Robertson, ed. IRL, Oxford, pp. 113–152. A chimeric embryo can then be implanted into a suitable pseudopregnant female foster animal and the embryo brought to term. Progeny harboring the homologously-recombined DNA in their germ cells can be used to breed animals in which all cells of the animal contain the homologously-recombined DNA by germline transmission of the transgene. Methods for constructing homologous recombination vectors and homologous recombinant animals are described further in Bradley, 1991. Curr. Opin. Biotechnol. 2: 823–829; PCT International Publication Nos.: WO 90/11354; WO 91/01140; WO 92/0968; and WO 93/04169.

In another embodiment, transgenic non-human animals can be produced that contain selected systems that allow for regulated expression of the transgene. One example of such a system is the cre/loxP recombinase system of bacteriophage P1. For a description of the cre/loxP recombinase system, See, e.g., Lakso, et al., 1992. Proc. Natl. Acad. Sci. USA 89: 6232–6236. Another example of a recombinase system is the FLP recombinase system of Saccharomyces cerevisiae. See, O'Gorman, et al., 1991. Science 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, et al., 1997. *Nature* 385: 810–813. In brief, a cell (e.g., a somatic cell) from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell (e.g., the somatic cell) is isolated.

Pharmaceutical Compositions

The SECP nucleic acid molecules, SECP proteins, and anti-SECP antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically-acceptable carrier. As used herein, "pharmaceutically-acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and other non-aqueous (ie., lipophilic) vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a SECP protein or anti-SECP antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including, liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad. Sci. USA* 91: 3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

Screening and Detection Methods

The nucleic acid molecules, proteins, protein homologues, and antibodies described herein can be used in one or more of the following methods: (A) screening assays; (B) detection assays (e.g., chromosomal mapping, cell and tissue typing, forensic biology), (C) predictive medicine (e.g., diagnostic assays, prognostic assays, monitoring clinical trials, and pharmacogenomics); and (D) methods of treatment (e.g., therapeutic and prophylactic).

The isolated nucleic acid molecules of the present invention can be used to express SECP protein (e.g., via a recombinant expression vector in a host cell in gene therapy applications), to detect SECP mRNA (e.g., in a biological sample) or a genetic lesion in an SECP gene, and to modulate SECP activity, as described further below. In addition, the SECP proteins can be used to screen drugs or compounds that modulate the SECP protein activity or expression as well as to treat disorders characterized by insufficient or excessive production of SECP protein or production of SECP protein forms that have decreased or aberrant activity compared to SECP wild-type protein. In addition, the anti-SECP antibodies of the present invention can be used to detect and isolate SECP proteins and modulate SECP activity.

The invention further pertains to novel agents identified by the screening assays described herein and uses thereof for treatments as previously described.

Screening Assays

The invention provides a method (also referred to herein as a "screening assay") for identifying modulators, i.e., candidate or test compounds or agents (e.g., peptides, peptidomimetics, small molecules or other drugs) that bind to SECP proteins or have a stimulatory or inhibitory effect on, e.g., SECP protein expression or SECP protein activity. The invention also includes compounds identified in the screening assays described herein.

In one embodiment, the invention provides assays for screening candidate or test compounds which bind to or modulate the activity of the membrane-bound form of a SECP protein or polypeptide or biologically-active portion thereof. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g., Lam, 1997. *Anticancer Drug Design* 12: 145.

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. *Proc. Natl. Acad. Sci. U.S.A.* 90: 6909; Erb, et al., 1994. *Proc. Natl. Acad. Sci. U.S.A.* 91: 11422; Zuckermann, et al., 1994. *J. Med. Chem.* 37: 2678; Cho, et al., 1993. *Science* 261: 1303; Carrell, et al., 1994. *Angew. Chem. Int. Ed. Engl.* 33: 2059; Carell, et al., 1994. *Angew. Chem. Int. Ed. Engl.* 33: 2061; and Gallop, et al., 1994. *J. Med. Chem.* 37: 1233.

Libraries of compounds may be presented in solution (e.g., Houghten, 1992. *Biotechniques* 13: 412–421), or on beads (Lam, 1991. *Nature* 354: 82–84), on chips (Fodor, 1993. *Nature* 364: 555–556), bacteria (Ladner, U.S. Pat. No.

5,223,409), spores (Ladner, U.S. Pat. No. 5,233,409), plasmids (Cull, et al., 1992. *Proc. Natl. Acad. Sci. USA* 89: 1865–1869) or on phage (Scott and Smith, 1990. *Science* 249: 386–390; Devlin, 1990. *Science* 249: 404–406; Cwirla, et al., 1990. *Proc. Natl. Acad. Sci. U.S.A.* 87: 6378–6382; Felici, 1991. *J. Mol. Biol.* 222: 301–310; Ladner, U.S. Pat. No. 5,233,409.).

In one embodiment, an assay is a cell-based assay in which a cell which expresses a membrane-bound form of SECP protein, or a biologically-active portion thereof, on the cell surface is contacted with a test compound and the ability of the test compound to bind to a SECP protein determined. The cell, for example, can of mammalian origin or a yeast cell. Determining the ability of the test compound to bind to the SECP protein can be accomplished, for example, by coupling the test compound with a radioisotope or enzymatic label such that binding of the test compound to the SECP protein or biologically-active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of SECP protein, or a biologically-active portion thereof, on the cell surface with a known compound which binds SECP to form an assay mixture, contacting the assay mixture with a test compound, and determining the ability of the test compound to interact with a SECP protein, wherein determining the ability of the test compound to interact with a SECP protein comprises determining the ability of the test compound to preferentially bind to SECP protein or a biologically-active portion thereof as compared to the known compound.

In another embodiment, an assay is a cell-based assay comprising contacting a cell expressing a membrane-bound form of SECP protein, or a biologically-active portion thereof, on the cell surface with a test compound and determining the ability of the test compound to modulate (e.g., stimulate or inhibit) the activity of the SECP protein or biologically-active portion thereof. Determining the ability of the test compound to modulate the activity of SECP or a biologically-active portion thereof can be accomplished, for example, by determining the ability of the SECP protein to bind to or interact with a SECP target molecule. As used herein, a "target molecule" is a molecule with which a SECP protein binds or interacts in nature, for example, a molecule on the surface of a cell which expresses a SECP interacting protein, a molecule on the surface of a second cell, a molecule in the extracellular milieu, a molecule associated with the internal surface of a cell membrane or a cytoplasmic molecule. An SECP target molecule can be a non-SECP molecule or a SECP protein or polypeptide of the invention. In one embodiment, a SECP target molecule is a component of a signal transduction pathway that facilitates transduction of an extracellular signal (e.g. a signal generated by binding of a compound to a membrane-bound SECP molecule) through the cell membrane and into the cell. The target, for example, can be a second intercellular protein that has catalytic activity or a protein that facilitates the association of downstream signaling molecules with SECP.

Determining the ability of the SECP protein to bind to or interact with a SECP target molecule can be accomplished by one of the methods described above for determining direct binding. In one embodiment, determining the ability of the SECP protein to bind to or interact with a SECP target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a SECP-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the invention is a cell-free assay comprising contacting a SECP protein or biologically-active portion thereof with a test compound and determining the ability of the test compound to bind to the SECP protein or biologically-active portion thereof. Binding of the test compound to the SECP protein can be determined either directly or indirectly as described above. In one such embodiment, the assay comprises contacting the SECP protein or biologically-active portion thereof with a known compound which binds SECP to form an assay mixture, contacting the assay mixture with a test compound, and determining the ability of the test compound to interact with a SECP protein, wherein determining the ability of the test compound to interact with a SECP protein comprises determining the ability of the test compound to preferentially bind to SECP or biologically-active portion thereof as compared to the known compound.

In still another embodiment, an assay is a cell-free assay comprising contacting SECP protein or biologically-active portion thereof with a test compound and determining the ability of the test compound to modulate (e.g. stimulate or inhibit) the activity of the SECP protein or biologically-active portion thereof. Determining the ability of the test compound to modulate the activity of SECP can be accomplished, for example, by determining the ability of the SECP protein to bind to a SECP target molecule by one of the methods described above for determining direct binding. In an alternative embodiment, determining the ability of the test compound to modulate the activity of SECP protein can be accomplished by determining the ability of the SECP protein further modulate a SECP target molecule. For example, the catalytic/enzymatic activity of the target molecule on an appropriate substrate can be determined as described, supra.

In yet another embodiment, the cell-free assay comprises contacting the SECP protein or biologically-active portion thereof with a known compound which binds SECP protein to form an assay mixture, contacting the assay mixture with a test compound, and determining the ability of the test compound to interact with a SECP protein, wherein determining the ability of the test compound to interact with a SECP protein comprises determining the ability of the SECP protein to preferentially bind to or modulate the activity of a SECP target molecule.

The cell-free assays of the invention are amenable to use of both the soluble form or the membrane-bound form of SECP protein. In the case of cell-free assays comprising the membrane-bound form of SECP protein, it may be desirable to utilize a solubilizing agent such that the membrane-bound form of SECP protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl) dimethylamminiol-2-hydroxy-1-propane sulfonate (CHAPSO).

In more than one embodiment of the above assay methods of the invention, it may be desirable to immobilize either SECP protein or its target molecule to facilitate separation of complexed from uncomplexed forms of one or both of the proteins, as well as to accommodate automation of the assay. Binding of a test compound to SECP protein, or interaction of SECP protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-SECP fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or SECP protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, supra. Alternatively, the complexes can be dissociated from the matrix, and the level of SECP protein binding or activity determined using standard techniques.

Other techniques for immobilizing proteins on matrices can also be used in the screening assays of the invention. For example, either the SECP protein or its target molecule can be immobilized utilizing conjugation of biotin and streptavidin. Biotinylated SECP protein or target molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with SECP protein or target molecules, but which do not interfere with binding of the SECP protein to its target molecule, can be derivatized to the wells of the plate, and unbound target or SECP protein trapped in the wells by antibody conjugation. Methods for detecting such complexes, in addition to those described above for the GST-immobilized complexes, include immunodetection of complexes using antibodies reactive with the SECP protein or target molecule, as well as enzyme-linked assays that rely on detecting an enzymatic activity associated with the SECP protein or target molecule.

In another embodiment, modulators of SECP protein expression are identified in a method wherein a cell is contacted with a candidate compound and the expression of SECP mRNA or protein in the cell is determined. The level of expression of SECP mRNA or protein in the presence of the candidate compound is compared to the level of expression of SECP mRNA or protein in the absence of the candidate compound. The candidate compound can then be identified as a modulator of SECP mRNA or protein expression based upon this comparison. For example, when expression of SECP mRNA or protein is greater (ie., statistically significantly greater) in the presence of the candidate compound than in its absence, the candidate compound is identified as a stimulator of SECP mRNA or protein expression. Alternatively, when expression of SECP mRNA or protein is less (statistically significantly less) in the presence of the candidate compound than in its absence, the candidate compound is identified as an inhibitor of SECP mRNA or protein expression. The level of SECP mRNA or protein expression in the cells can be determined by methods described herein for detecting SECP mRNA or protein.

In yet another aspect of the invention, the SECP proteins can be used as "bait proteins" in a two-hybrid assay or three hybrid assay (see, e.g., U.S. Pat. No. 5,283,317; Zervos, et al., 1993. Cell 72: 223–232; Madura, et al., 1993. J. Biol. Chem. 268: 12046–12054; Bartel, et al., 1993. Biotechniques 14: 920–924; Iwabuchi, et al., 1993. Oncogene 8: 1693–1696; and Brent WO 94/10300), to identify other proteins that bind to or interact with SECP ("SECP-binding proteins" or "SECP-bp") and modulate SECP activity. Such SECP-binding proteins are also likely to be involved in the propagation of signals by the SECP proteins as, for example, upstream or downstream elements of the SECP pathway.

The two-hybrid system is based on the modular nature of most transcription factors, which consist of separable DNA-binding and activation domains. Briefly, the assay utilizes two different DNA constructs. In one construct, the gene that codes for SECP is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a SECP-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with SECP.

The invention further pertains to novel agents identified by the aforementioned screening assays and uses thereof for treatments as described herein.

Detection Assays

Portions or fragments of the cDNA sequences identified herein (and the corresponding complete gene sequences) can be used in numerous ways as polynucleotide reagents. By way of example, and not of limitation, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. Some of these applications are described in the subsections below.

Chromosome Mapping

Once the sequence (or a portion of the sequence) of a gene has been isolated, this sequence can be used to map the location of the gene on a chromosome. This process is called chromosome mapping. Accordingly, portions or fragments of the SECP sequences shown in SEQ ID NO:1, 3, 5, 7, 9, 11, 13, 15, and/or 17, or fragments or derivatives thereof, can be used to map the location of the SECP genes, respectively, on a chromosome. The mapping of the SECP sequences to chromosomes is an important first step in correlating these sequences with genes associated with disease.

Briefly, SECP genes can be mapped to chromosomes by preparing PCR primers (preferably 15–25 bp in length) from the SECP sequences. Computer analysis of the SECP, sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the SECP sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. See, e.g., D'Eustachio, et al., 1983. *Science* 220: 919–924. Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the SECP sequences to design oligonucleotide primers, sub-localization can be achieved with panels of fragments from specific chromosomes.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases, will suffice to get good results at a reasonable amount of time. For a review of this technique, see, Verma, et al., HUMAN CHROMOSOMES: A MANUAL OF BASIC TECHNIQUES (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to non-coding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. Such data are found, e.g., in McKusick, MENDELIAN INHERITANCE IN MAN, available on-line through Johns Hopkins University Welch Medical Library). The relationship between genes and disease, mapped to the same chromosomal region, can then be identified through linkage analysis (co-inheritance of physically adjacent genes), described in, e.g., Egeland, et al., 1987. *Nature,* 325: 783–787.

Additionally, differences in the DNA sequences between individuals affected and unaffected with a disease associated with the SECP gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

The SECP sequences of the invention can also be used to identify individuals from minute biological samples. In this technique, an individual's genomic DNA is digested with one or more restriction enzymes, and probed on a Southern blot to yield unique bands for identification. The sequences of the invention are useful as additional DNA markers for RFLP ("restriction fragment length polymorphisms," as described in U.S. Pat. No. 5,272,057).

Furthermore, the sequences of the invention can be used to provide an alternative technique that determines the actual base-by-base DNA sequence of selected portions of an individual's genome. Thus, the SECP sequences described herein can be used to prepare two PCR primers from the 5'- and 3'-termini of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the invention can be used to obtain such identification sequences from individuals and from tissue. The SECP sequences of the invention uniquely represent portions of the human genome. Allelic variation occurs to some degree in the coding regions of these sequences, and to a greater degree in the non-coding regions. It is estimated that allelic variation between individual humans occurs with a frequency of about once per each 500 bases. Much of the allelic variation is due to single nucleotide polymorphisms (SNPs), which include restriction fragment length polymorphisms (RFLPs).

Each of the sequences described herein can, to some degree, be used as a standard against which DNA from an individual can be compared for identification purposes. Because greater numbers of polymorphisms occur in the non-coding regions, fewer sequences are necessary to differentiate individuals. The non-coding sequences can comfortably provide positive individual identification with a panel of perhaps 10 to 1,000 primers that each yield a non-coding amplified sequence of 100 bases. If predicted coding sequences, such as those in SEQ ID NO:1, 3, 5, 7, 9, 11, 13, 15, and/or 17 are used, a more appropriate number of primers for positive individual identification would be 500–2,000.

Predictive Medicine

The invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the invention relates to diagnostic assays for determining SECP protein and/or nucleic acid expression as well as SECP activity, in the context of a biological sample (e.g., blood, serum, cells, tissue) to thereby determine whether an individual is afflicted with a disease or disorder, or is at risk of developing a disorder, associated with aberrant SECP expression or activity. The invention also provides for prognostic (or predictive) assays for determining whether an individual is at risk of developing a disorder associated with SECP protein, nucleic acid expression or activity. For example, mutations in a SECP gene can be assayed in a biological sample. Such assays can be used for prognostic or predictive purpose to thereby prophylactically treat an individual prior to the onset of a disorder characterized by or associated with SECP protein, nucleic acid expression or activity.

Another aspect of the invention provides methods for determining SECP protein, nucleic acid expression or SECP activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs, compounds) on the expression or activity of SECP in clinical trials.

Use of Partial SECP Sequences in Forensic Biology

DNA-based identification techniques can also be used in forensic biology. Forensic biology is a scientific field employing genetic typing of biological evidence found at a crime scene as a means for positively identifying, e.g., a perpetrator of a crime. To make such an identification, PCR technology can be used to amplify DNA sequences taken from very small biological samples such as tissues (e.g., hair or skin, or body fluids, e.g., blood, saliva, or semen found at a crime scene). The amplified sequence can then be compared to a standard, thereby allowing identification of the origin of the biological sample.

The sequences of the invention can be used to provide polynucleotide reagents, e.g., PCR primers, targeted to specific loci in the human genome, that can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to non-coding regions of SEQ ID NO:1, 3, 5, 7, 9, 11, 13, 15, and/or 17 are particularly appropriate for this use as greater numbers of polymorphisms occur in the non-coding regions, making it easier to differentiate individuals using this technique. Examples of polynucleotide reagents include the SECP sequences or portions thereof, e.g., fragments derived from the non-coding regions of one or more of SEQ ID NO:1, 3, 5, 7, 9, 11, 13, 15, and/or 17, having a length of at least 20 bases, preferably at least 30 bases.

The SECP sequences described herein can further be used to provide polynucleotide reagents, e.g., labeled or labelable probes that can be used, for example, in an in situ hybridization technique, to identify a specific tissue (e.g., brain tissue, etc). This can be very useful in cases where a forensic pathologist is presented with a tissue of unknown origin. Panels of such SECP probes can be used to identify tissue by species and/or by organ type.

In a similar fashion, these reagents, e.g., SECP primers or probes can be used to screen tissue culture for contamination (i.e., screen for the presence of a mixture of different types of cells in a culture).

Predictive Medicine

The invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the invention relates to diagnostic assays for determining SECP protein and/or nucleic acid expression as well as SECP activity, in the context of a biological sample (e.g., blood, serum, cells, tissue) to thereby determine whether an individual is afflicted with a disease or disorder, or is at risk of developing a disorder, associated with aberrant SECP expression or activity. The invention also provides for prognostic (or predictive) assays for determining whether an individual is at risk of developing a disorder associated with SECP protein, nucleic acid expression or activity. For example, mutations in a SECP gene can be assayed in a biological sample. Such assays can be used for prognostic or predictive purpose to thereby prophylactically treat an individual prior to the onset of a disorder characterized by or associated with SECP protein, nucleic acid expression, or biological activity.

Another aspect of the invention provides methods for determining SECP protein, nucleic acid expression or activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs, compounds) on the expression or activity of SECP in clinical trials.

These and various other agents are described in further detail in the following sections.

Diagnostic Assays

An exemplary method for detecting the presence or absence of SECP in a biological sample involves obtaining a biological sample from a test subject and contacting the biological sample with a compound or an agent capable of detecting SECP protein or nucleic acid (e.g., mRNA, genomic DNA) that encodes SECP protein such that the presence of SECP is detected in the biological sample. An agent for detecting SECP mRNA or genomic DNA is a labeled nucleic acid probe capable of hybridizing to SECP mRNA or genomic DNA. The nucleic acid probe can be, for example, a full-length SECP nucleic acid, such as the nucleic acid of SEQ ID NO:1, 3, 5, 7, 9, 11, 13, 15, and/or 17, or a portion thereof, such as an oligonucleotide of at least 15, 30, 50, 100, 250 or 500 nucleotides in length and sufficient to specifically hybridize under stringent conditions to SECP mRNA or genomic DNA. Other suitable probes for use in the diagnostic assays of the invention are described herein.

An agent for detecting SECP protein is an antibody capable of binding to SECP protein, preferably an antibody with a detectable label. Antibodies can be polyclonal, or more preferably, monoclonal. An intact antibody, or a fragment thereof (e.g., $F_{ab}$ or $F_{(ab)2}$) can be used. The term "labeled", with regard to the probe or antibody, is intended to encompass direct labeling of the probe or antibody by coupling (ie., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect SECP mRNA, protein, or genomic DNA in a biological sample in vitro as well as in vivo. For example, in vitro techniques for detection of SECP mRNA include Northern hybridizations and in situ hybridizations. In vitro techniques for detection of SECP protein include enzyme linked immunosorbent assays (ELISAs), Western blots, immunoprecipitations, and immunofluorescence. In vitro techniques for detection of SECP genomic DNA include Southern hybridizations. Furthermore, in vivo techniques for detection of SECP protein include introducing into a subject a labeled anti-SECP antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting SECP protein, mRNA, or genomic DNA, such that the presence of SECP protein, mRNA or genomic DNA is detected in the biological sample, and comparing the presence of SECP protein, mRNA or genomic DNA in the control sample with the presence of SECP protein, mRNA or genomic DNA in the test sample.

The invention also encompasses kits for detecting the presence of SECP in a biological sample. For example, the kit can comprise: a labeled compound or agent capable of detecting SECP protein or mRNA in a biological sample; means for determining the amount of SECP in the sample; and means for comparing the amount of SECP in the sample with a standard. The compound or agent can be packaged in a suitable container. The kit can further comprise instructions for using the kit to detect SECP protein or nucleic acid.

Prognostic Assays

The diagnostic methods described herein can furthermore be utilized to identify subjects having or at risk of developing a disease or disorder associated with aberrant SECP expression or activity. For example, the assays described herein, such as the preceding diagnostic assays or the following assays, can be utilized to identify a subject having or at risk of developing a disorder associated with SECP protein, nucleic acid expression or activity. Alternatively, the prognostic assays can be utilized to identify a subject having or at risk for developing a disease or disorder. Thus, the invention provides a method for identifying a disease or disorder associated with aberrant SECP expression or activity in which a test sample is obtained from a subject and SECP protein or nucleic acid (e.g., mRNA, genomic DNA) is detected, wherein the presence of SECP protein or nucleic acid is diagnostic for a subject having or at risk of developing a disease or disorder associated with aberrant SECP expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant SECP expression or activity. For example, such methods can be used to determine whether a subject can be effectively treated with an agent for a disorder. Thus, the invention provides methods for determining whether a subject can be effectively treated with an agent for a disorder associated with aberrant SECP expression or activity in which a test sample is obtained and SECP protein or nucleic acid is detected (e.g., wherein the presence of SECP protein or nucleic acid is diagnostic for a subject that can be administered the agent to treat a disorder associated with aberrant SECP expression or activity).

The methods of the invention can also be used to detect genetic lesions in a SECP gene, thereby determining if a subject with the lesioned gene is at risk for a disorder characterized by aberrant cell proliferation and/or differentiation. In various embodiments, the methods include detecting, in a sample of cells from the subject, the presence or absence of a genetic lesion characterized by at least one of an alteration affecting the integrity of a gene encoding a SECP-protein, or the mis-expression of the SECP gene. For example, such genetic lesions can be detected by ascertaining the existence of at least one of: (i) a deletion of one or more nucleotides from a SECP gene; (ii) an addition of one or more nucleotides to a SECP gene; (iii) a substitution of one or more nucleotides of a SECP gene, (iv) a chromosomal rearrangement of a SECP gene; (v) an alteration in the level of a messenger RNA transcript of a SECP gene, (vi) aberrant modification of a SECP gene, such as of the methylation pattern of the genomic DNA, (vii) the presence of a non-wild-type splicing pattern of a messenger RNA transcript of a SECP gene, (viii) a non-wild-type level of a SECP protein, (ix) allelic loss of a SECP gene, and (x) inappropriate post-translational modification of a SECP protein. As described herein, there are a large number of assay techniques known in the art which can be used for detecting lesions in a SECP gene. A preferred biological sample is a peripheral blood leukocyte sample isolated by conventional means from a subject. However, any biological sample containing nucleated cells may be used, including, for example, buccal mucosal cells.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran, et al., 1988. *Science* 241: 1077–1080; and Nakazawa, et al., 1994. *Proc. Natl. Acad. Sci. USA* 91: 360–364), the latter of which can be particularly useful for detecting point mutations in the SECP-gene (see, Abravaya, et al., 1995. *Nucl. Acids Res.* 23: 675–682). This method can include the steps of collecting a sample of cells from a patient, isolating nucleic acid (e.g., genomic, mRNA or both) from the cells of the sample, contacting the nucleic acid sample with one or more primers that specifically hybridize to a SECP gene under conditions such that hybridization and amplification of the SECP gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (see, Guatelli, et al., 1990. *Proc. Natl. Acad. Sci. USA* 87: 1874–1878), transcriptional amplification system (see, Kwoh, et al., 1989. *Proc. Natl. Acad. Sci. USA* 86: 1173–1177); Qβ Replicase (see, Lizardi, et al, 1988. *BioTechnology* 6: 1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a SECP gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,493,531) can be used to score for the presence of specific mutations by development or loss of a ribozyme cleavage site.

In other embodiments, genetic mutations in SECP can be identified by hybridizing a sample and control nucleic acids, e.g., DNA or RNA, to high-density arrays containing hundreds or thousands of oligonucleotides probes. See, e.g., Cronin, et al., 1996. *Human Mutation* 7: 244–255; Kozal, et al., 1996. *Nat. Med.* 2: 753–759. For example, genetic mutations in SECP can be identified in two dimensional arrays containing light-generated DNA probes as described in Cronin, et al., supra. Briefly, a first hybridization array of probes can be used to scan through long stretches of DNA in a sample and control to identify base changes between the sequences by making linear arrays of sequential overlapping probes. This step allows the identification of point mutations. This is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the SECP gene and detect mutations by comparing the sequence of the sample SECP with the corresponding wild-type (control) sequence. Examples of sequencing reactions include those based on techniques developed by Maxim and Gilbert, 1977. *Proc. Natl. Acad. Sci. USA* 74: 560 or Sanger, 1977. *Proc. Natl. Acad. Sci. USA* 74: 5463. It is also contemplated that any of a variety of automated sequencing procedures can be utilized when performing the diagnostic assays (see, e.g., Naeve, et al., 1995. *Biotechniques* 19: 448), including sequencing by mass spectrometry (see, e.g., PCT International Publication No. WO 94/16101; Cohen, et al., 1996. *Adv. Chromatography* 36: 127–162; and Griffin, et al., 1993. *Appl. Biochem. Biotechnol.* 38: 147–159).

Other methods for detecting mutations in the SECP gene include methods in which protection from cleavage agents is used to detect mismatched bases in RNA/RNA or RNA/DNA heteroduplexes. See, e.g., Myers, et al., 1985. *Science* 230: 1242. In general, the art technique of "mismatch cleavage" starts by providing heteroduplexes of formed by hybridizing (labeled) RNA or DNA containing the wild-type SECP sequence with potentially mutant RNA or DNA obtained from a tissue sample. The double-stranded duplexes are treated with an agent that cleaves single-stranded regions of the duplex such as which will exist due to basepair mismatches between the control and sample strands. For instance, RNA/DNA duplexes can be treated with RNase and DNA/DNA hybrids treated with $S_1$ nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton, et al., 1988. *Proc. Natl. Acad. Sci. USA* 85: 4397; Saleeba, et al., 1992. *Methods Enzymol.* 217: 286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in SECP cDNAs obtained from samples of cells. For example, the mutY enzyme of *E. coli* cleaves A at G/A mismatches and the thymidine DNA glycosylase from HeLa cells cleaves T at G/T mismatches. See, e.g., Hsu, et al., 1994. *Carcinogenesis* 15: 1657–1662. According to an exemplary embodiment, a probe based on a SECP sequence, e.g., a wild-type SECP sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in SECP genes. For example, single strand conformation polymorphism (SSCP) may be used to detect differences in electrophoretic mobility between mutant and wild type nucleic acids. See, e.g., Orita, et al., 1989. *Proc. Natl. Acad. Sci. USA:* 86: 2766; Cotton, 1993. *Mutat. Res.* 285: 125–144; Hayashi, 1992. *Genet. Anal. Tech. Appl.* 9: 73–79. Single-stranded DNA fragments of sample and control SECP nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility. See, e.g., Keen, et al., 1991. *Trends Genet.* 7: 5.

In yet another embodiment, the movement of mutant or wild-type fragments in polyacrylamide gels containing a gradient of denaturant is assayed using denaturing gradient gel electrophoresis (DGGE). See, e.g., Myers, et al., 1985. *Nature* 313: 495. When DGGE is used as the method of analysis, DNA will be modified to insure that it does not completely denature, for example by adding a GC clamp of approximately 40 bp of high-melting GC-rich DNA by PCR.

In a further embodiment, a temperature gradient is used in place of a denaturing gradient to identify differences in the mobility of control and sample DNA. See, e.g., Rosenbaum and Reissner, 1987. *Biophys. Chem.* 265: 12753.

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found. See, e.g., Saiki, et al., 1986. *Nature* 324: 163; Saiki, et al., 1989. *Proc. Natl. Acad. Sci. USA* 86: 6230. Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization; see, e.g., Gibbs, et al., 1989. *Nucl. Acids Res.* 17: 2437–2448) or at the extreme 3'-terminus of one primer where, under appropriate conditions, mismatch can prevent, or reduce polymerase extension (see, e.g., Prossner, 1993. *Tibtech.* 11: 238). In addition it may be desirable to introduce a novel restriction site in the region of the mutation to create cleavage-based detection. See, e.g., Gasparini, et al., 1992. *Mol. Cell Probes* 6: 1. It is anticipated that in certain embodiments amplification may also be performed using Taq ligase for amplification. See, e.g., Barany, 1991. *Proc. Natl. Acad. Sci. USA* 88: 189. In such cases, ligation will occur only if there is a perfect match at the 3'-terminus of the 5' sequence, making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a SECP gene.

Furthermore, any cell type or tissue, preferably peripheral blood leukocytes, in which SECP is expressed may be utilized in the prognostic assays described herein. However, any biological sample containing nucleated cells may be used, including, for example, buccal mucosal cells.

Pharmacogenomics

Agents, or modulators that have a stimulatory or inhibitory effect on SECP activity (e.g., SECP gene expression), as identified by a screening assay described herein can be administered to individuals to treat (prophylactically or therapeutically) disorders (e.g., cancer or immune disorders associated with aberrant SECP activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of SECP protein, expression of SECP nucleic acid, or mutation content of SECP genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum, 1996. *Clin. Exp. Pharmacol. Physiol.* 23: 983–985; Linder, 1997. *Clin. Chem.,* 43: 254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. At the other extreme are the so called ultra-rapid metabolizers who do not respond to standard doses. Recently, the molecular basis of ultra-rapid metabolism has been identified to be due to CYP2D6 gene amplification.

Thus, the activity of SECP protein, expression of SECP nucleic acid, or mutation content of SECP genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a SECP modulator, such as a modulator identified by one of the exemplary screening assays described herein.

Monitoring of Effects During Clinical Trials

Monitoring the influence of agents (e.g., drugs, compounds) on the expression or activity of SECP (e.g., the ability to modulate aberrant cell proliferation and/or differentiation) can be applied not only in basic drug screening, but also in clinical trials. For example, the effectiveness of an agent determined by a screening assay as described herein to increase SECP gene expression, protein levels, or upregulate SECP activity, can be monitored in clinical trails of subjects exhibiting decreased SECP gene expression, protein levels, or down-regulated SECP activity. Alternatively, the effectiveness of an agent determined by a screening assay to decrease SECP gene expression, protein levels, or down-regulate SECP activity, can be monitored in clinical trails of subjects exhibiting increased SECP gene expression, protein levels, or up-regulated SECP activity. In such clinical trials, the expression or activity of SECP and, preferably, other genes that have been implicated in, for example, a cellular proliferation or immune disorder can be used as a "read out" or markers of the immune responsiveness of a particular cell.

By way of example, and not of limitation, genes, including SECP, that are modulated in cells by treatment with an agent (e.g., compound, drug or small molecule) that modulates SECP activity (e.g., identified in a screening assay as described herein) can be identified. Thus, to study the effect of agents on cellular proliferation disorders, for example, in a clinical trial, cells can be isolated and RNA prepared and analyzed for the levels of expression of SECP and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of SECP or other genes. In this manner, the gene expression pattern can serve as a marker, indicative of the physiological response of the cells to the agent. Accordingly, this response state may be determined before, and at various points during, treatment of the individual with the agent.

In one embodiment, the invention provides a method for monitoring the effectiveness of treatment of a subject with an agent (e.g., an agonist, antagonist, protein, peptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of a SECP protein, mRNA, or genomic DNA in the pre-administration sample; (iii) obtaining one or more post-administration samples from the subject; (iv) detecting the level of expression or activity of the SECP protein, mRNA, or genomic DNA in the post-administration samples; (v) comparing the level of expression or activity of the SECP protein, mRNA, or genomic DNA in the pre-administration sample with the SECP protein, mRNA, or genomic DNA in the post administration sample or samples; and (vi) altering the administration of the agent to the subject accordingly. For example, increased administration of the agent may be desirable to increase the expression or activity of SECP to higher levels than detected, i.e., to increase the effectiveness of the agent. Alternatively, decreased administration of the agent may be desirable to decrease expression or activity of SECP to lower levels than detected, i.e., to decrease the effectiveness of the agent.

Methods of Treatment

The invention provides for both prophylactic and therapeutic methods of treating a subject at risk of (or susceptible to) a disorder or having a disorder associated with aberrant SECP expression or activity. These methods of treatment will be discussed more fully, below.

Disease and Disorders

Diseases and disorders that are characterized by increased (relative to a subject not suffering from the disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to: (i) an aforementioned peptide, or analogs, derivatives, fragments or homologs thereof; (ii) antibodies to an aforementioned peptide; (iii) nucleic acids encoding an aforementioned peptide; (iv) administration of antisense nucleic acid and nucleic acids that are "dysfunctional" (i.e., due to a heterologous insertion within the coding sequences of coding sequences to an aforementioned peptide) that are utilized to "knockout" endoggenous function of an aforementioned peptide by homologous recombination (see, e.g., Capecchi, 1989. *Science* 244: 1288–1292); or (v) modulators (i.e., inhibitors, agonists and antagonists, including additional peptide mimetic of the invention or antibodies specific to a peptide of the invention) that alter the interaction between an aforementioned peptide and its binding partner.

Diseases and disorders that are characterized by decreased (relative to a subject not suffering from the disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, an aforementioned peptide, or analogs, derivatives, fragments or homologs thereof, or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of an aforementioned peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, and the like).

Prophylactic Methods

In one aspect, the invention provides a method for preventing, in a subject, a disease or condition associated with an aberrant SECP expression or activity, by administering to the subject an agent that modulates SECP expression or at least one SECP activity. Subjects at risk for a disease that is caused or contributed to by aberrant SECP expression or activity can be identified by, for example, any or a combination of diagnostic or prognostic assays as described herein. Administration of a prophylactic agent can occur prior to the manifestation of symptoms characteristic of the SECP aberrancy, such that a disease or disorder is prevented or, alternatively, delayed in its progression. Depending upon the type of SECP aberrancy, for example, a SECP agonist or SECP antagonist agent can be used for treating the subject. The appropriate agent can be determined based on screening assays described herein.

Therapeutic Methods

Another aspect of the invention pertains to methods of modulating SECP expression or activity for therapeutic purposes. The modulatory method of the invention involves contacting a cell with an agent that modulates one or more of the activities of SECP protein activity associated with the cell. An agent that modulates SECP protein activity can be an agent as described herein, such as a nucleic acid or a protein, a naturally-occurring cognate ligand of a SECP protein, a peptide, a SECP peptidomimetic, or other small molecule. In one embodiment, the agent stimulates one or more SECP protein activity. Examples of such stimulatory agents include active SECP protein and a nucleic acid molecule encoding SECP that has been introduced into the cell. In another embodiment, the agent inhibits one or more SECP protein activity. Examples of such inhibitory agents include antisense SECP nucleic acid molecules and anti-SECP antibodies. These modulatory methods can be performed in vitro (e.g., by culturing the cell with the agent) or, alternatively, in vivo (e.g., by administering the agent to a subject). As such, the invention provides methods of treating an individual afflicted with a disease or disorder characterized by aberrant expression or activity of a SECP protein or nucleic acid molecule. In one embodiment, the method involves administering an agent (e.g., an agent identified by a screening assay described herein), or combination of agents that modulates (e.g., up-regulates or down-regulates)

SECP expression or activity. In another embodiment, the method involves administering a SECP protein or nucleic acid molecule as therapy to compensate for reduced or aberrant SECP expression or activity.

Stimulation of SECP activity is desirable in situations in which SECP is abnormally down-regulated and/or in which increased SECP activity is likely to have a beneficial effect. One example of such a situation is where a subject has a disorder characterized by aberrant cell proliferation and/or differentiation (e.g., cancer or immune associated disorders). Another example of such a situation is where the subject has a gestational disease (e.g., pre-clampsia).

Determination of the Biological Effect of the Therapeutic

In various embodiments of the invention, suitable in vitro or in vivo assays are performed to determine the effect of a specific Therapeutic and whether its administration is indicated for treatment of the affected tissue.

In various specific embodiments, in vitro assays may be performed with representative cells of the type(s) involved in the patient's disorder, to determine if a given Therapeutic exerts the desired effect upon the cell type(s). Compounds for use in therapy may be tested in suitable animal model systems including, but not limited to rats, mice, chicken, cows, monkeys, rabbits, and the like, prior to testing in human subjects. Similarly, for in vivo testing, any of the animal model system known in the art may be used prior to administration to human subjects.

Prophylactic and Therapeutic Uses of the Compositions of the Invention

The SECP nucleic acids and proteins of the invention may be useful in a variety of potential prophylactic and therapeutic applications. By way of a non-limiting example, a cDNA encoding the SECP protein of the invention may be useful in gene therapy, and the protein may be useful when administered to a subject in need thereof.

Both the novel nucleic acids encoding the SECP proteins, and the SECP proteins of the invention, or fragments thereof, may also be useful in diagnostic applications, wherein the presence or amount of the nucleic acid or the protein are to be assessed. These materials are further useful in the generation of antibodies which immunospecifically-bind to the novel substances of the invention for use in therapeutic or diagnostic methods.

The invention will be further illustrated in the following non-limiting examples.

EXAMPLE 1

Radiation Hybrid Mapping Provides the Chromosomal Location of SECP 2 (Clone 11618130.0.27)

Radiation hybrid mapping using human chromosome markers was carried out to determine the chromosomal location of a SECP2 nuclei acid of the invention. The procedure used to obtain these results is described generally in Steen, et al., 1999. A High-Density Integrated Genetic Linkage and Radiation Hybrid Map of the Laboratory Rat, *Genome Res.* 9: AP1–AP8 (Published Online on May 21, 1999). A panel of 93 cell clones containing randomized radiation-induced human chromosomal fragments was then screened in 96 well plates using PCR primers designed to identify the sought clones in a unique fashion. Clone 11618130.0.27, a SECP2 nucleic acid was located on chromosome 16 at a map distance of 26.0 cR from marker WI-3768 and −70.5 cR from marker TIGR-A002K05.

EXAMPLE 2

Molecular Cloning of Clone 11618130

Oligonucleotide PCR primers were designed to amplify a DNA segment coding for the full length open reading frame of clone 11618130. The forward primer included a Bgl II restriction site and the consensus Kozak sequence CCACC. The reverse primer contained an in-frame XhoI restriction site. Both primers contained a CTCGTC 5'-terminus clamp. The nucleotide sequences of the primers were:

11618130 Forward Primer:
CTCGTCAGATCTCCACCATGAGTGATGAGGACAGCT (SEQ ID NO:19) GTGTAG 11618130 Reverse Primer:
CTCGTCCTCGAGGCAGCTGGTTGGTTGGCTTATGTT (SEQ ID NO:20) G The PCR reactions included: 5 ng human fetal brain cDNA template; 1 μM of each of the 11618130 Forward and 11618130 Reverse primers; 5 μM dNTP (Clontech Laboratories; Palo Alto, Calif.) and 1 μl of 50× Advantage-HF 2 polymerase (Clontech Laboratories; Palo Alto, Calif.) in 50 μl total reaction volume. The following PCR conditions were used:

a) 96° C. 3 minutes
b) 96° C. 30 seconds denaturation
c) 70° C. 30 seconds, primer annealing. This temperature was gradually decreased by 1° C./cycle
d) 72° C. 1 minute extension.
Repeat steps b–d a total of 10-times
e) 96° C. 30 seconds denaturation
f) 60° C. 30 seconds annealing
g) 72° C. 1 minute extension
Repeat steps e–g a total of 25-times
h) 72° C. 5 minutes final extension A single, amplified product of approximately 800 bp was detected by agarose gel electrophoresis. The PCR amplification product was then isolated by the QIAEX II® Gel Extraction System (QIAGEN, Inc; Valencia, Calif.) in a final volume of 20 μl.

A total of 10 μl of the isolated fragment was digested with Bgl II and XhoI restriction enzymes, and ligated into the BamHI- and XhoI-digested mammalian expression vector pCDNA3.1 V5His (Invitrogen; Carlsbad, Calif.). The construct was sequenced, and the cloned insert was verified as a sequence identical to the ORF coding for the full length 11618130. The construct was designated pcDNA3.1-11618130-S178-2.

EXAMPLE 3

Expression of 11618130 In Human Embryonic Kidney 293 Cells

The vector pcDNA3.1-11618130-S178-2 described in Example 2 was subsequently transfected into human embryonic kidney 293 cells (ATCC No. CRL-1573; Manassas, Va.) using the LipofectaminePlus Reagent following the manufacturer's instructions (Gibco/BRL/Life Technologies; Rockville, Md.) The cell pellet and supernatant were harvested 72 hours after transfection, and examined for 11618130 expression by use of SDS-PAGE under reducing conditions and Western blotting with an anti-V5 antibody. FIG. 12 shows that 11618130 was expressed as a protein having an apparent molecular weight (Mr) of approximately 34 kilo Daltons (kDa) which was intracellularly expressed in the 293 cells. These experimental results were consistent with the predicted molecular weight of 28043 Daltons for the protein of clone 11618130.0.27 and with the predicted localization of the protein intracellularly in the microbody (peroxisome). A second band of approximately 54 kDa was also found, which may represent a non-reducible dimer of this protein.

EXAMPLE 4

Preparation of Mammalian Expression Vector pSecV5His

The oligonucleotide primers, pSec-V5-His Forward and pSec-V5-His Reverse, were generated to amplify a fragment from the pcDNA3.1-V5His (Invitrogen; Carlsbad, Calif.) expression vector that includes V5 and His6. The nucleotide sequences of these primers were:

```
pSec-V5-His Forward Primer:
CTCGTCCTCGAGGGTAAGCCTATCCCTAAC    (SEQ ID NO:21)

pSec-V5-His Reverse Primer:
CTCGTCGGGCCCCTGATCAGCGGGTTTAAAC   (SEQ ID NO:22)
```

The PCR product was digested with XhoI and ApaI, and ligated into the XhoI/ApaI-digested pSecTag2 B vector harboring an Ig kappa leader sequence (Invitrogen; Carlsbad, Calif.). The correct structure of the resulting vector (designated pSecV5His), including an in-frame Ig-kappa leader and V5-His6, was verified by DNA sequence analysis. The pSecV5His vector included an in-frame Ig kappa leader, a site for insertion of a clone of interest, V5 and His6, which allows heterologous protein expression and secretion by fusing any protein to the Ig kappa chain signal peptide. Detection and purification of the expressed protein was aided by the presence of the V5 epitope tag and 6× His tag at the carboxyl-terminus (Invitrogen; Carlsbad, Calif.).

EXAMPLE 5

Molecular Cloning of 16406477

Oligonucleotide PCR primers were designed to amplify a DNA segment encoding for the mature form of clone 16406477 from amino acid residues 38 to 385, recognition of the signal sequence predicted for this polypeptide. The forward primer contained an in-frame BamHI restriction site and the reverse primer contained an in-frame XhoI restriction site. Both primers contained the CTCGTC 5' clamp. The sequences of the primers were as follows:

```
16406477 Forward Primer:
CTCGTCGGATCCTGGGGCGCAGGGGAAGCCCCGGG    (SEQ ID NO:23)

16406477 Reverse Primer:
CTCGTCCTCGAGGAGGGCAGCAAGGAGGCTGAGGG    (SEQ ID NO:24)
GCAG
```

The PCR reactions contained: 5 ng human fetal brain cDNA template; 1 μM of each of the 16406477 Forward and 16406477 Reverse Primers; 5 μM dNTP (Clontech Laboratories; Palo Alto, Calif.) and 1 μl of 50× Advantage-HF 2 polymerase (Clontech Laboratories; Palo Alto, Calif.) in a 50 μl total reaction volume. PCR was then conducted using reaction conditions identical to those previously described in Example 2.

A single, amplified product of approximately 1 Kbp was detected by agarose gel electrophoresis. The product was then isolated by QIAEX II® Gel Extraction System (QUIAGEN, Inc; Valencia, Calif.) in a total reaction volume of 20 μl.

A total of 10 μl of the isolated fragment was digested with BamHI and XhoI restriction enzymes, and ligated into the pSecV5-His mammalian expression vector (see, Example 4) which had been previously-digested with BamHI and XhoI. The construct was sequenced, and the cloned insert was verified as possessing a sequence identical to that of the ORF coding for the mature fragment of clone 16406477. The construct was subsequently designated pSecV5His-16406477-S196-A.

EXAMPLE 6

Expression of 16406477 in Human Embryonic Kidney 293 Cells

Figure 13:
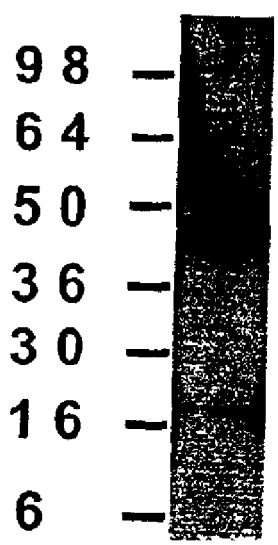
FIG. 13 is a representation of a Western blot of a polypeptide expressed in 293 cells of a polynucleotide containing sequence encoded by clone 16406477.

The pSecV5His-16406477-S196-A construct (see, Example 5) was subsequently transfected into 293 cells (ATCC No. CRL-1573; Manassas, Va.) using the LipofectaminePlus Reagent following the manufacturer's instructions (Gibco/BRL/Life Technologies). The cell pellet and supernatant were harvested 72 hours after transfection, and examined for 16406477 expression by use of SDS-PAGE under reducing conditions and Western blotting with an anti-V5 antibody. FIG. 13 demonstrates that 16406477 is expressed as a protein having an apparent molecular weight (Mr) of approximately 45 kDa which is retained intracellularly in the 293 cells. The Mr value which was found upon expression of the clone is consistent with the predicted molecular weight of 43087 Daltons.

EXAMPLE 7

Quantitative Tissue Expression Analysis of Clones of the Invention

The Quantitative Expression Analysis of several clones of the invention was preformed in 41 normal and 55 tumor samples (see, FIG. 14) by real-time quantitative PCR (TAQMAN®) by use of a Perkin-Elmer Biosystems ABI PRISM® 7700 Sequence Detection System. The following abbreviations are used in FIG. 14:

ca.=carcinoma,

*=established from metastasis, met=metastasis, s cell var=small cell variant, non-s=non-sm=non-small, squam=squamous, pl. eff=pl effusion=pleural effusion, glio=glioma, astro=astrocytoma, and neuro=neuroblastoma.

Initially, 96 RNA samples were normalized to β-actin and GAPDH. RNA (~50 ng total or ~1 ng poly(A)+) was converted to cDNA using the TAQMAN® Reverse Transcription Reagents Kit (PE Biosystems; Foster City, Calif.; Catalog No. N808-0234) and random hexamers according to the manufacturer's protocol. Reactions were performed in a 20 μl total volume, and incubated for 30 minutes at 48° C. cDNA (5 μl) was then transferred to a separate plate for the TAQMAN® reaction using β-actin and GAPDH TAQMAN® Assay Reagents (PE Biosystems; Catalog Nos. 4310881E and 4310884E, respectively) and TAQMAN® Universal PCR Master Mix (PE Biosystems; Catalog No. 4304447) according to the manufacturer's protocol. Reactions were performed in a 25 μl total volume using the following parameters: 2 minutes at 50° C.; 10 minutes at 95° C.; 15 seconds at 95° C./1 min. at 60° C. (40 cycles total).

Results were recorded as CT values (i.e., cycle at which a given sample crosses a threshold level of fluorescence) using a log scale, with the difference in RNA concentration between a given sample and the sample with the lowest CT value being represented as $2^{\delta CT}$. The percent relative expression is then obtained by taking the reciprocal of this RNA difference and multiplying by 100. The average CT values obtained for β-actin and GAPDH were used to normalize RNA samples. The RNA sample generating the highest CT value required no further diluting, while all other samples were diluted relative to this sample according to their β-actin/GAPDH average CT values.

Normalized RNA (5 µl) was converted to cDNA and analyzed via TAQMAN® using One Step RT-PCR Master Mix Reagents (PE Biosystems; Catalog No. 4309169) and gene-specific primers according to the manufacturer's instructions. Probes and primers were designed for each assay according to Perkin Elmer Biosystem's Primer Express Software package (Version I for Apple Computer's Macintosh Power PC) using the sequence of the respective clones as input. Default settings were used for reaction conditions and the following parameters were set before selecting primers: primer concentration=250 nM; primer melting temperature ($T_m$) range=58°–60° C.; primer optimal Tm=59° C.; maximum primer difference=2° C., probe does not posses a 5'-terminus G; probe $T_m$ must be 10° C. greater than primer $T_m$; and amplicon size 75 bp to 100 bp in length. The probes and primers were synthesized by Synthegen (Houston, Tex.). Probes were double-purified by HPLC to remove uncoupled dye and then evaluated by mass spectroscopy to verify coupling of reporter and quencher dyes to the 5'- and 3'-termini of the probe, respectively. Their final concentrations used were—Forward and Reverse Primers= 900 nM each; and probe=200 nM.

Subsequent PCR conditions were as follows. Normalized RNA from each tissue and each cell line was spotted in each well of a 96 well PCR plate (Perkin Elmer Biosystems). PCR reaction mixes, including two probes (i.e., SECP-specific and another gene-specific probe multiplexed with the SEPC-specific probe) were set up using 1× TaqMan™ PCR Master Mix for the PE Biosystems 7700, with 5 mM $MgCl_2$; dNTPs (dA, G, C, U at 1:1:1:2 ratios); 0.25 U/ml AmpliTaq Gold™ (PE Biosystems); 0.4 U/µl RNase inhibitor; and 0.25 U/µl Reverse Transcriptase. Reverse transcription was then performed at 48° C. for 30 minutes, followed by amplification/PCR cycles as follows: 95° C. 10 minuets, then 40 cycles of 95° C. for 15 seconds, and 60° C. for 1 minute.

The primer-probe sets employed in the expression analysis of each clone, and a summary of the results, are provided below. The complete experimental results are illustrated in FIG. 14. The panel of cell lines employed was identical in all cases except that samples 95 and 96 were gDNA and a melanoma UACC-257 (control), respectively, in the experiments for clone 11696905. The nucleotide sequences of the primer sets used for these clones are as follows:

```
Clone 11696905.0.47 Primer Set:

Ag 383 (F):  5'-GGCCTCTCCGTACCCTTCTC-3'                  (SEQ ID NO:25)

Ag 383 (R):  5'-AGAGGCTCTTGGCGCAGTT-3'                   (SEQ ID NO:26)

Ag 383 (P):  TET-5'-ACCAGGATCACGACCTCCGCAGG-3'-TAMPA     (SEQ ID NO:27)
```

Primer Set Ag 383 was designed to probe for nucleotides 403–478 in SEPC 3 (clone 11696905.0.47). The results indicate that the clone was prominently expressed in normal cells such as adipose, adrenal gland, various regions of the brain, skeletal muscle, bladder, liver and fetal liver, mammary gland, placenta, prostate and testis. It was also found to be expressed at levels much higher than comparable normal cells in cancers of the kidney and lung, and expressed at levels much lower than comparable normal cells in cancers of the central nervous system (CNS) and breast. These results suggest that SEPC 3 (clone 11696905.0.47), or fragments thereof, may be useful in probing for cancer in kidney and lung, and that the nucleic acid or the protein of clone 11696905.0.47 may be a target for therapeutic agents in such cancers. These nucleic acids and proteins may be useful as therapeutic agents in treating cancers of the CNS and breast.

```
Clone 16406477.0.206 Primer Set:

Ag 53 (F):  5'-GCCTGGCACGGACTATGTGT-3'                   (SEQ ID NO:28)

Ag 53 (R):  5'-GCCGTCAGCCTTGGAAAGT-3'                    (SEQ ID NO:29)

Ag 53 (P):  TET-5'-CCATTCCCGCTGCACTGTGACG-3'-TAMRA       (SEQ ID NO:30)
```

SEPC 7 (clone 16406477.0.206) was found to be expressed essentially exclusively in testis cells, with a low level of expression in the hypothalamus, among the cells tested.

| Clone 21433858 Primer Set: | |
|---|---|
| Ag 127 (F): 5'-CCTGCCAGGATGACTGTCAATT-3' | (SEQ ID NO:31) |
| Ag 127 (R): 5'-TGGTCCTAACTGCACCACAGTCT-3' | (SEQ ID NO:32) |
| Ag 127 (P): TET-5'-CCAGCTGGTCCAAGTTTTCTTCATGCAA-3'-TAMRA | (SEQ ID NO:33) |

Probe set Ag 127 targets nucleotides 2524–2601 of SECP1 (clone 21433858). The results show that the clone is expressed principally in normal tissues such as adipose, brain, bladder, fetal and adult kidney, mammary gland, myometrium, uterus, placenta, and testis. In comparison to normal lung tissue, it is highly expressed in a small cell lung cancer, a large cell lung cancer, and a non-small cell lung cancer. Therefore, SECP1 (clone 21433858), or a fragment thereof, may be useful as a diagnostic probe for such lung cancers. The nucleic acids or proteins of SECP1 (clone 21433858) may furthermore serve as targets for the treatment of cancer in these and other tissues.

| Clone 21637262.0.64 Primer Set: | |
|---|---|
| Ab5(F): 5'-GTGATCCTCAGGCTGGACCA-3' | (SEQ ID NO:34) |
| Ab5(R): 5'-TTCTGACTGGGCTGCATCC-3' | (SEQ ID NO:35) |
| Ab5(P): FAM-5'-CCAGTGTTTCCTCAGCACAGGGCC-3'-TAMRA | (SEQ ID NO:36) |

Probe set Ab5 targets nucleotides 1221–1298 in SECP9 (clone 21637262.0.64). The results shown in FIG. 14 demonstrate that SECP9 (clone 21637262.0.64) is expressed in cells from normal tissues including, especially, the salivary gland and trachea, among those cells examined.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid comprising a nucleic acid sequence encoding the polypeptide of SEQ ID NO: 6.

2. An isolated nucleic acid comprising a nucleic acid sequence encoding amino acids 26–405 of SEQ ID NO:6.

3. A vector comprising the nucleic acid claim 1.

4. A cell comprising the vector of claim 3.

5. An isolated nucleic acid comprising the nucleic acid sequence of SEQ ID NO: 5.

6. An isolated nucleic acid consisting essentially of the nucleic acid sequence of SEQ ID NO: 5.

7. An isolated nucleic acid consisting of the nucleic acid sequence of SEQ ID NO: 5.

8. An isolated nucleic acid comprising the compliment of the nucleic acid of claim 1.

9. An isolated nucleic acid comprising the compliment of the nucleic acid of claim 2.

10. An isolated nucleic acid comprising the compliment of the nucleic acid of claim 5.

* * * * *

SEQUENCE LISTING

```
<160> NUMBER OF SEQ ID NOS: 36

<210> SEQ ID NO 1
<211> LENGTH: 6373
<212> TYPE: DNA
<213> ORGANISM: Homo sapiens
<220> FEATURE:
<221> NAME/KEY: CDS
<222> LOCATION: (235)..(4998)
<221> NAME/KEY: misc_feature
<222> LOCATION: (6349)
<223> OTHER INFORMATION: Wherein n is a or t or g or c.

<400> SEQUENCE: 1
gacagagtgc agccttttca gactctgtga cacagttccc cttttgcaaa aatacttagc        60
gaggatcatt actttccaac agtcgtgtcc agagacctac tttgtaacac cgcagggaag       120
ttaatgtact aggtcttgaa aggtctttct ggaatgtgca gtaacttgta gttttcttct       180
agtagcactg ctaattttg tgttataatt tttgtaggtc catggggccg atgt atg         237
                                                                  Met
                                                                   1
```

```
                                                                          -continued gga gat gaa tgt ggt ccc gga ggc atc caa acg agg gct gtg tgg tgt        285
Gly Asp Glu Cys Gly Pro Gly Gly Ile Gln Thr Arg Ala Val Trp Cys
            5               10                  15 gct cat gtg gag gga tgg act aca ctg cat act aac tgt aag cag gcc        333
Ala His Val Glu Gly Trp Thr Thr Leu His Thr Asn Cys Lys Gln Ala
        20                  25                  30 gag aga ccc aat aac cag cag aat tgt ttc aaa gtt tgc gat tgg cac        381
Glu Arg Pro Asn Asn Gln Gln Asn Cys Phe Lys Val Cys Asp Trp His
    35                  40                  45 aaa gag ttg tac gac tgg aga ctg gga cct tgg aat cag tgt cag ccc        429
Lys Glu Leu Tyr Asp Trp Arg Leu Gly Pro Trp Asn Gln Cys Gln Pro
 50                  55                  60                  65 gtg att tca aaa agc cta gag aaa cct ctt gag tgc att aag ggg gaa        477
Val Ile Ser Lys Ser Leu Glu Lys Pro Leu Glu Cys Ile Lys Gly Glu
                 70                  75                  80 gaa ggt att cag gtg agg gag ata gcg tgc atc cag aaa gac aaa gac        525
Glu Gly Ile Gln Val Arg Glu Ile Ala Cys Ile Gln Lys Asp Lys Asp
             85                  90                  95 att cct gcg gag gat atc atc tgt gag tac ttt gag ccc aag cct ctc        573
Ile Pro Ala Glu Asp Ile Ile Cys Glu Tyr Phe Glu Pro Lys Pro Leu
        100                 105                 110 ctg gag cag gct tgc ctc att cct tgc cag caa gat tgc atc gtg tct        621
Leu Glu Gln Ala Cys Leu Ile Pro Cys Gln Gln Asp Cys Ile Val Ser
    115                 120                 125 gaa ttt tct gcc tgg tcc gaa tgc tcc aag acc tgc ggc agc ggg ctc        669
Glu Phe Ser Ala Trp Ser Glu Cys Ser Lys Thr Cys Gly Ser Gly Leu
130                 135                 140                 145 cag cac cgg acg cgt cat gtg gtg gcg ccc ccg cag ttc gga ggc tct        717
Gln His Arg Thr Arg His Val Val Ala Pro Pro Gln Phe Gly Gly Ser
                150                 155                 160 ggc tgt cca aac ctg acg gag ttc cag gtg tgc caa tcc agt cca tgc        765
Gly Cys Pro Asn Leu Thr Glu Phe Gln Val Cys Gln Ser Ser Pro Cys
            165                 170                 175 gag gcc gag gag ctc agg tac agc ctg cat gtg ggg ccc tgg agc acc        813
Glu Ala Glu Glu Leu Arg Tyr Ser Leu His Val Gly Pro Trp Ser Thr
        180                 185                 190 tgc tca atg ccc cac tcc cga caa gta aga caa gca agg aga cgc ggg        861
Cys Ser Met Pro His Ser Arg Gln Val Arg Gln Ala Arg Arg Arg Gly
    195                 200                 205 aag aat aaa gaa cgg gaa aag gac cgc agc aaa gga gta aag gat cca        909
Lys Asn Lys Glu Arg Glu Lys Asp Arg Ser Lys Gly Val Lys Asp Pro
210                 215                 220                 225 gaa gcc cgc gag ctt att aag aaa aag aga aac aga aac agg cag aac        957
Glu Ala Arg Glu Leu Ile Lys Lys Lys Arg Asn Arg Asn Arg Gln Asn
                230                 235                 240 aga caa gag aac aaa tat tgg gac atc cag att gga tat cag acc aga       1005
Arg Gln Glu Asn Lys Tyr Trp Asp Ile Gln Ile Gly Tyr Gln Thr Arg
            245                 250                 255 gag gtt atg tgc att aac aag acg ggg aaa gct gct gat tta agc ttt       1053
Glu Val Met Cys Ile Asn Lys Thr Gly Lys Ala Ala Asp Leu Ser Phe
        260                 265                 270 tgc cag caa gag aag ctt cca atg acc ttc cag tcc tgt gtg atc acc       1101
Cys Gln Gln Glu Lys Leu Pro Met Thr Phe Gln Ser Cys Val Ile Thr
    275                 280                 285 aaa gag tgc cag gtt tcc gag tgg tca gag tgg agc ccc tgc tca aaa       1149
Lys Glu Cys Gln Val Ser Glu Trp Ser Glu Trp Ser Pro Cys Ser Lys
290                 295                 300                 305 aca tgc cat gac atg gtg tcc cct gca ggc act cgt gta agg aca cga       1197
Thr Cys His Asp Met Val Ser Pro Ala Gly Thr Arg Val Arg Thr Arg
                310                 315                 320
```

```
acc atc agg cag ttt ccc att ggc agt gaa aag gag tgt cca gaa ttt      1245
Thr Ile Arg Gln Phe Pro Ile Gly Ser Glu Lys Glu Cys Pro Glu Phe
            325                 330                 335 gaa gaa aaa gaa ccc tgt ttg tct caa gga gat gga gtt gtc ccc tgt      1293
Glu Glu Lys Glu Pro Cys Leu Ser Gln Gly Asp Gly Val Val Pro Cys
        340                 345                 350 gcc acg tat ggc tgg aga act aca gag tgg act gag tgc cgt gtg gac      1341
Ala Thr Tyr Gly Trp Arg Thr Thr Glu Trp Thr Glu Cys Arg Val Asp
355                 360                 365 cct ttg ctc agt cag cag gac aag agg cgc ggc aac cag acg gcc ctc      1389
Pro Leu Leu Ser Gln Gln Asp Lys Arg Arg Gly Asn Gln Thr Ala Leu
370                 375                 380                 385 tgt gga ggg ggc atc cag acc cga gag gtg tac tgc gtg cag gcc aac      1437
Cys Gly Gly Gly Ile Gln Thr Arg Glu Val Tyr Cys Val Gln Ala Asn
                390                 395                 400 gaa aac ctc ctc tca caa tta agt acc cac aag aac aaa gaa gcc tca      1485
Glu Asn Leu Leu Ser Gln Leu Ser Thr His Lys Asn Lys Glu Ala Ser
            405                 410                 415 aag cca atg gac tta aaa tta tgc act gga cct atc cct aat act aca      1533
Lys Pro Met Asp Leu Lys Leu Cys Thr Gly Pro Ile Pro Asn Thr Thr
        420                 425                 430 cag ctg tgc cac att cct tgt cca act gaa tgt gaa gtt tca cct tgg      1581
Gln Leu Cys His Ile Pro Cys Pro Thr Glu Cys Glu Val Ser Pro Trp
435                 440                 445 tca gct tgg gga cct tgt act tat gaa aac tgt aat gat cag caa ggg      1629
Ser Ala Trp Gly Pro Cys Thr Tyr Glu Asn Cys Asn Asp Gln Gln Gly
450                 455                 460                 465 aaa aaa ggc ttc aaa ctg agg aag cgg cgc att acc aat gag ccc act      1677
Lys Lys Gly Phe Lys Leu Arg Lys Arg Arg Ile Thr Asn Glu Pro Thr
                470                 475                 480 gga ggc tct ggg gta acc gga aac tgc cct cac tta ctg gaa gcc att      1725
Gly Gly Ser Gly Val Thr Gly Asn Cys Pro His Leu Leu Glu Ala Ile
            485                 490                 495 ccc tgt gaa gag cct gcc tgt tat gac tgg aaa gcg gtg aga ctg gga      1773
Pro Cys Glu Glu Pro Ala Cys Tyr Asp Trp Lys Ala Val Arg Leu Gly
        500                 505                 510 gac tgc gag cca gat aac gga aag gag tgt ggt cca ggc acg caa gtt      1821
Asp Cys Glu Pro Asp Asn Gly Lys Glu Cys Gly Pro Gly Thr Gln Val
515                 520                 525 caa gag gtt gtg tgc atc aac agt gat gga gaa gaa gtt gac aga cag      1869
Gln Glu Val Val Cys Ile Asn Ser Asp Gly Glu Glu Val Asp Arg Gln
530                 535                 540                 545 ctg tgc aga gat gcc atc ttc ccc atc cct gtg gcc tgt gat gcc cca      1917
Leu Cys Arg Asp Ala Ile Phe Pro Ile Pro Val Ala Cys Asp Ala Pro
                550                 555                 560 tgc ccg aaa gac tgt gtg ctc agc aca tgg tct acg tgg tcc tcc tgc      1965
Cys Pro Lys Asp Cys Val Leu Ser Thr Trp Ser Thr Trp Ser Ser Cys
            565                 570                 575 tca cac acc tgc tca ggg aaa acg aca gaa ggg aaa cag ata cga gca      2013
Ser His Thr Cys Ser Gly Lys Thr Thr Glu Gly Lys Gln Ile Arg Ala
        580                 585                 590 cga tcc att ctg gcc tat gcg ggt gaa gaa ggt gga att cgc tgt cca      2061
Arg Ser Ile Leu Ala Tyr Ala Gly Glu Glu Gly Gly Ile Arg Cys Pro
595                 600                 605 aat agc agt gct ttg caa gaa gta cga agc tgt aat gag cat cct tgc      2109
Asn Ser Ser Ala Leu Gln Glu Val Arg Ser Cys Asn Glu His Pro Cys
610                 615                 620                 625 aca gtg tac cac tgg caa act ggt ccc tgg ggc cag tgc att gag gac      2157
Thr Val Tyr His Trp Gln Thr Gly Pro Trp Gly Gln Cys Ile Glu Asp
```

```
                         630                 635                 640
acc tca gta tcg tcc ttc aac aca act acg act tgg aat ggg gag gcc        2205
Thr Ser Val Ser Ser Phe Asn Thr Thr Thr Thr Trp Asn Gly Glu Ala
            645                 650                 655 tcc tgc tct gtc ggc atg cag aca aga aaa gtc atc tgt gtg cga gtc        2253
Ser Cys Ser Val Gly Met Gln Thr Arg Lys Val Ile Cys Val Arg Val
            660                 665                 670 aat gtg ggc caa gtg gga ccc aaa aaa tgt cct gaa agc ctt cga cct        2301
Asn Val Gly Gln Val Gly Pro Lys Lys Cys Pro Glu Ser Leu Arg Pro
675                 680                 685 gaa act gta agg cct tgt ctg ctt cct tgt aag aag gac tgt att gtg        2349
Glu Thr Val Arg Pro Cys Leu Leu Pro Cys Lys Lys Asp Cys Ile Val
690                 695                 700                 705 acc cca tat agt gac tgg aca tca tgc ccc tct tcg tgt aaa gaa ggg        2397
Thr Pro Tyr Ser Asp Trp Thr Ser Cys Pro Ser Ser Cys Lys Glu Gly
                710                 715                 720 gac tcc agt atc agg aag cag tct agg cat cgg gtc atc att cag ctg        2445
Asp Ser Ser Ile Arg Lys Gln Ser Arg His Arg Val Ile Ile Gln Leu
            725                 730                 735 cca gcc aac ggg ggc cga gac tgc aca gat ccc ctc tat gaa gag aag        2493
Pro Ala Asn Gly Gly Arg Asp Cys Thr Asp Pro Leu Tyr Glu Glu Lys
            740                 745                 750 gcc tgt gag gca cct caa gcg tgc caa agc tac agg tgg aag act cac        2541
Ala Cys Glu Ala Pro Gln Ala Cys Gln Ser Tyr Arg Trp Lys Thr His
755                 760                 765 aaa tgg cgc aga tgc caa tta gtc cct tgg agc gtg caa caa gac agc        2589
Lys Trp Arg Arg Cys Gln Leu Val Pro Trp Ser Val Gln Gln Asp Ser
770                 775                 780                 785 cct gga gca cag gaa ggc tgt ggg cct ggg cga cag gca aga gcc att        2637
Pro Gly Ala Gln Glu Gly Cys Gly Pro Gly Arg Gln Ala Arg Ala Ile
                790                 795                 800 act tgt cgc aag caa gat gga gga cag gct gga atc cat gag tgc cta        2685
Thr Cys Arg Lys Gln Asp Gly Gly Gln Ala Gly Ile His Glu Cys Leu
            805                 810                 815 cag tat gca ggc cct gtg cca gcc ctt acc cag gcc tgc cag atc ccc        2733
Gln Tyr Ala Gly Pro Val Pro Ala Leu Thr Gln Ala Cys Gln Ile Pro
            820                 825                 830 tgc cag gat gac tgt caa ttg acc agc tgg tcc aag ttt tct tca tgc        2781
Cys Gln Asp Asp Cys Gln Leu Thr Ser Trp Ser Lys Phe Ser Ser Cys
835                 840                 845 aat gga gac tgt ggt gca gtt agg acc aga aag cgc act ctt gtt gga        2829
Asn Gly Asp Cys Gly Ala Val Arg Thr Arg Lys Arg Thr Leu Val Gly
850                 855                 860                 865 aaa agt aaa aag aag gaa aaa tgt aaa aat tcc cat ttg tat ccc ctg        2877
Lys Ser Lys Lys Lys Glu Lys Cys Lys Asn Ser His Leu Tyr Pro Leu
                870                 875                 880 att gag act cag tat tgt cct tgt gac aaa tat aat gca caa cct gtg        2925
Ile Glu Thr Gln Tyr Cys Pro Cys Asp Lys Tyr Asn Ala Gln Pro Val
            885                 890                 895 ggg aac tgg tca gac tgt att tta cca gag gga aaa gtg gaa gtg ttg        2973
Gly Asn Trp Ser Asp Cys Ile Leu Pro Glu Gly Lys Val Glu Val Leu
            900                 905                 910 ctg gga atg aaa gta caa gga gac atc aag gaa tgc gga caa gga tat        3021
Leu Gly Met Lys Val Gln Gly Asp Ile Lys Glu Cys Gly Gln Gly Tyr
915                 920                 925 cgt tac caa gca atg gca tgc tac gat caa aat ggc agg ctt gtg gaa        3069
Arg Tyr Gln Ala Met Ala Cys Tyr Asp Gln Asn Gly Arg Leu Val Glu
930                 935                 940                 945 aca tct aga tgt aac agc cat ggt tac att gag gag gcc tgc atc atc        3117
```

-continued

```
Thr Ser Arg Cys Asn Ser His Gly Tyr Ile Glu Glu Ala Cys Ile Ile
            950                 955                 960 ccc tgc ccc tca gac tgc aag ctc agt gag tgg tcc aac tgg tcg cgc     3165
Pro Cys Pro Ser Asp Cys Lys Leu Ser Glu Trp Ser Asn Trp Ser Arg
            965                 970                 975 tgc agc aag tcc tgt ggg agt ggt gtg aag gtt cgt tct aaa tgg ctg     3213
Cys Ser Lys Ser Cys Gly Ser Gly Val Lys Val Arg Ser Lys Trp Leu
            980                 985                 990 cgt gaa aaa cca tat aat gga gga agg cct tgc ccc aaa ctg gac cat     3261
Arg Glu Lys Pro Tyr Asn Gly Gly Arg Pro Cys Pro Lys Leu Asp His
        995                 1000                1005 gtc aac cag gca cag gtg tat gag gtt gtc cca tgc cac agt gac tgc     3309
Val Asn Gln Ala Gln Val Tyr Glu Val Val Pro Cys His Ser Asp Cys
    1010                1015                1020                1025 aac cag tac cta tgg gtc aca gag ccc tgg agc atc tgc aag gtg acc     3357
Asn Gln Tyr Leu Trp Val Thr Glu Pro Trp Ser Ile Cys Lys Val Thr
                1030                1035                1040 ttt gtg aat atg cgg gag aac tgt gga gag ggc gtg caa acc cga aaa     3405
Phe Val Asn Met Arg Glu Asn Cys Gly Glu Gly Val Gln Thr Arg Lys
                1045                1050                1055 gtg aga tgc atg cag aat aca gca gat ggc cct tct gaa cat gta gag     3453
Val Arg Cys Met Gln Asn Thr Ala Asp Gly Pro Ser Glu His Val Glu
    1060                1065                1070 gat tac ctc tgt gac cca gaa gag atg ccc ctg ggc tct aga gtg tgc     3501
Asp Tyr Leu Cys Asp Pro Glu Glu Met Pro Leu Gly Ser Arg Val Cys
        1075                1080                1085 aaa tta cca tgc cct gag gac tgt gtg ata tct gaa tgg ggt cca tgg     3549
Lys Leu Pro Cys Pro Glu Asp Cys Val Ile Ser Glu Trp Gly Pro Trp
1090                1095                1100                1105 acc caa tgt gtt ttg cct tgc aat caa agc agt ttc cgg caa agg tca     3597
Thr Gln Cys Val Leu Pro Cys Asn Gln Ser Ser Phe Arg Gln Arg Ser
                1110                1115                1120 gct gat ccc atc aga caa cca gct gat gaa gga aga tct tgc cct aat     3645
Ala Asp Pro Ile Arg Gln Pro Ala Asp Glu Gly Arg Ser Cys Pro Asn
                1125                1130                1135 gct gtt gag aaa gaa ccc tgt aac ctg aac aaa aac tgc tac cac tat     3693
Ala Val Glu Lys Glu Pro Cys Asn Leu Asn Lys Asn Cys Tyr His Tyr
                1140                1145                1150 gat tat aat gta aca gac tgg agt aca tgt cag ctg agt gag aag gca     3741
Asp Tyr Asn Val Thr Asp Trp Ser Thr Cys Gln Leu Ser Glu Lys Ala
    1155                1160                1165 gtt tgt gga aat gga ata aaa aca agg atg ttg gat tgt gtt cga agt     3789
Val Cys Gly Asn Gly Ile Lys Thr Arg Met Leu Asp Cys Val Arg Ser
1170                1175                1180                1185 gat ggc aag tca gtt gac ctg aaa tat tgt gaa gcg ctt ggc ttg gag     3837
Asp Gly Lys Ser Val Asp Leu Lys Tyr Cys Glu Ala Leu Gly Leu Glu
                1190                1195                1200 aag aac tgg cag atg aac acg tcc tgc atg gtg gaa tgc cct gtg aac     3885
Lys Asn Trp Gln Met Asn Thr Ser Cys Met Val Glu Cys Pro Val Asn
            1205                1210                1215 tgt cag ctt tct gat tgg tct cct tgg tca gaa tgt tct caa aca tgt     3933
Cys Gln Leu Ser Asp Trp Ser Pro Trp Ser Glu Cys Ser Gln Thr Cys
        1220                1225                1230 ggc ctc aca gga aaa atg atc cga aga cga aca gtg acc cag ccc ttt     3981
Gly Leu Thr Gly Lys Met Ile Arg Arg Arg Thr Val Thr Gln Pro Phe
    1235                1240                1245 caa ggt gat gga aga cca tgc cct tcc ctg atg gac cag tcc aaa ccc     4029
Gln Gly Asp Gly Arg Pro Cys Pro Ser Leu Met Asp Gln Ser Lys Pro
1250                1255                1260                1265
```

```
                                            -continued tgc cca gtg aag cct tgt tat cgg tgg caa tat ggc cag tgg tct cca    4077
Cys Pro Val Lys Pro Cys Tyr Arg Trp Gln Tyr Gly Gln Trp Ser Pro
            1270                1275                1280 tgc caa gtg cag gag gcc cag tgt gga gaa ggg acc aga aca agg aac    4125
Cys Gln Val Gln Glu Ala Gln Cys Gly Glu Gly Thr Arg Thr Arg Asn
        1285                1290                1295 att tct tgt gta gta agt gat ggg tca gct gat gat ttc agc aaa gtg    4173
Ile Ser Cys Val Val Ser Asp Gly Ser Ala Asp Asp Phe Ser Lys Val
    1300                1305                1310 gtg gat gag gaa ttc tgt gct gac att gaa ctc att ata gat ggt aat    4221
Val Asp Glu Glu Phe Cys Ala Asp Ile Glu Leu Ile Ile Asp Gly Asn
        1315                1320                1325 aaa aat atg gtt ctg gag gaa tcc tgc agc cag cct tgc cca ggt gac    4269
Lys Asn Met Val Leu Glu Glu Ser Cys Ser Gln Pro Cys Pro Gly Asp
1330                1335                1340                1345 tgt tat ttg aag gac tgg tct tcc tgg agc ctg tgt cag ctg acc tgt    4317
Cys Tyr Leu Lys Asp Trp Ser Ser Trp Ser Leu Cys Gln Leu Thr Cys
            1350                1355                1360 gtg aat ggt gag gat cta ggc ttt ggt gga ata cag gtc aga tcc aga    4365
Val Asn Gly Glu Asp Leu Gly Phe Gly Gly Ile Gln Val Arg Ser Arg
        1365                1370                1375 ccg gtg att ata caa gaa cta gag aat cag cat ctg tgc cca gag cag    4413
Pro Val Ile Ile Gln Glu Leu Glu Asn Gln His Leu Cys Pro Glu Gln
    1380                1385                1390 atg tta gaa aca aaa tca tgt tat gat gga cag tgc tat gaa tat aaa    4461
Met Leu Glu Thr Lys Ser Cys Tyr Asp Gly Gln Cys Tyr Glu Tyr Lys
        1395                1400                1405 tgg atg gcc agt gct tgg aag ggc tct tcc cga aca gtg tgg tgt caa    4509
Trp Met Ala Ser Ala Trp Lys Gly Ser Ser Arg Thr Val Trp Cys Gln
1410                1415                1420                1425 agg tca gat ggt ata aat gta aca ggg ggc tgc ttg gtg atg agc cag    4557
Arg Ser Asp Gly Ile Asn Val Thr Gly Gly Cys Leu Val Met Ser Gln
            1430                1435                1440 cct gat gcc gac agg tct tgt aac cca ccg tgt agt caa ccc cac tcg    4605
Pro Asp Ala Asp Arg Ser Cys Asn Pro Pro Cys Ser Gln Pro His Ser
        1445                1450                1455 tac tgt agc gag aca aaa aca tgc cat tgt gaa gaa ggg tac act gaa    4653
Tyr Cys Ser Glu Thr Lys Thr Cys His Cys Glu Glu Gly Tyr Thr Glu
    1460                1465                1470 gtc atg tct tct aac agc acc ctt gag caa tgc aca ctt atc ccc gtg    4701
Val Met Ser Ser Asn Ser Thr Leu Glu Gln Cys Thr Leu Ile Pro Val
    1475                1480                1485 gtg gta tta ccc acc atg gag gac aaa aga gga gat gtg aaa acc agt    4749
Val Val Leu Pro Thr Met Glu Asp Lys Arg Gly Asp Val Lys Thr Ser
1490                1495                1500                1505 cgg gct gta cat cca acc caa ccc tcc agt aac cca gca gga cgg gga    4797
Arg Ala Val His Pro Thr Gln Pro Ser Ser Asn Pro Ala Gly Arg Gly
            1510                1515                1520 agg acc tgg ttt cta cag cca ttt ggg cca gat ggg aga cta aag acc    4845
Arg Thr Trp Phe Leu Gln Pro Phe Gly Pro Asp Gly Arg Leu Lys Thr
        1525                1530                1535 tgg gtt tac ggt gta gca gct ggg gca ttt gtg tta ctc atc ttt att    4893
Trp Val Tyr Gly Val Ala Ala Gly Ala Phe Val Leu Leu Ile Phe Ile
    1540                1545                1550 gtc tcc atg att tat cta gct tgc aaa aag cca aag aaa ccc aag aga    4941
Val Ser Met Ile Tyr Leu Ala Cys Lys Lys Pro Lys Lys Pro Gln Arg
    1555                1560                1565 agg caa aac aac cga ctg aaa cct tta acc tta gcc tat gat gga gat    4989
Arg Gln Asn Asn Arg Leu Lys Pro Leu Thr Leu Ala Tyr Asp Gly Asp
1570                1575                1580                1585
```

```
gcc gac atg taacatataa cttttcctgg caacaaccag tttcggcttt        5038
Ala Asp Met ctgacttcat agatgtccag aggccacaac aaatgtatcc aaactgtgtg gattaaaata    5098
tattttaatt tttaaaaatg gcatcataaa gacaagagtg aaaatcatac tgccactgga    5158
gatatttaag acagtaccac ttatatacag accatcaacc gtgagaatta taggagattt    5218
agctgaatac atgctgcatt ctgaaagttt tatgtcatct tttctgaaat ctaccgactg    5278
aaaaaccact ttcatctcta aaaataatg gtggaattgg ccagttagga tgcctgatac     5338
aagaccgtct gcagtgttaa tccataaaac ttcctagcat gaagagtttc taccaagatc    5398
tccacaatac tatggtcaaa ttaacatgtg tactcagttg aatgacacac attatgtcag    5458
attatgtact tgctaataag caattttaac aatgcataac aaataaactc taagctaagc    5518
agaaaatcca ctgaataaat tcagcatctt ggtggtcgat ggtagatttt attgacctgc    5578
atttcagaga caaagcctct tttttaagac ttcttgtctc tctccaaagt aagaatgctg    5638
gacaagtact agtgtcttag aagaacgagt cctcaagttc agtattttat agtggtaatt    5698
gtctggaaaa ctaatttact tgtgttaata caatacgttt ctactttccc tgattttcaa    5758
actggttgcc tgcatctttt ttgctatatg gaaggcacat ttttgcacta tattagtgca    5818
gcacgatagg cgcttaacca gtattgccat agaaactgcc tcttttcatg tgggatgaag    5878
acatctgtgc caagagtggc atgaagacat ttgcaagttc ttgtatcctg aagagagtaa    5938
agttcagttt ggatggcagc aagatgaaat cagctattac acctgctgta cacacacttc    5998
ctcatcactg cagccattgt gaaattgaca acatggcggt aatttaagtg ttgaagtccc    6058 taaccccctta accctctaaa aggtggattc ctctagttgg tttgtaattg ttctttgaag    6118
gctgtttatg actagatttt tatatttgtt atctttgtta agaaaaaaaa aagaaaaagg    6178
aactggatgt cttttttaatt ttgagcagat ggagaaaata aataatgtat caatgacctt    6238
tgtaactaaa ggaaaaaaaa aaaaaatgtg gattttcctt tctctctgat ttcccagttt    6298
cagattgaat gtctgtcttg caggcagtta tttcaaaatc catagtcttt ngcctttctc    6358
actggcaaaa tttga                                                     6373

<210> SEQ ID NO 2
<211> LENGTH: 1588
<212> TYPE: PRT
<213> ORGANISM: Homo sapiens

<400> SEQUENCE: 2

Met Gly Asp Glu Cys Gly Pro Gly Gly Ile Gln Thr Arg Ala Val Trp
 1               5                  10                  15

Cys Ala His Val Glu Gly Trp Thr Thr Leu His Thr Asn Cys Lys Gln
                20                  25                  30

Ala Glu Arg Pro Asn Asn Gln Gln Asn Cys Phe Lys Val Cys Asp Trp
            35                  40                  45

His Lys Glu Leu Tyr Asp Trp Arg Leu Gly Pro Trp Asn Gln Cys Gln
        50                  55                  60

Pro Val Ile Ser Lys Ser Leu Glu Lys Pro Leu Glu Cys Ile Lys Gly
 65                  70                  75                  80

Glu Glu Gly Ile Gln Val Arg Glu Ile Ala Cys Ile Gln Lys Asp Lys
                85                  90                  95

Asp Ile Pro Ala Glu Asp Ile Ile Cys Glu Tyr Phe Glu Pro Lys Pro
            100                 105                 110
```

```
Leu Leu Glu Gln Ala Cys Leu Ile Pro Cys Gln Gln Asp Cys Ile Val
            115                 120                 125

Ser Glu Phe Ser Ala Trp Ser Glu Cys Ser Lys Thr Cys Gly Ser Gly
    130                 135                 140

Leu Gln His Arg Thr Arg His Val Val Ala Pro Pro Gln Phe Gly Gly
145                 150                 155                 160

Ser Gly Cys Pro Asn Leu Thr Glu Phe Gln Val Cys Gln Ser Ser Pro
                165                 170                 175

Cys Glu Ala Glu Glu Leu Arg Tyr Ser Leu His Val Gly Pro Trp Ser
            180                 185                 190

Thr Cys Ser Met Pro His Ser Arg Gln Val Arg Gln Ala Arg Arg Arg
        195                 200                 205

Gly Lys Asn Lys Glu Arg Glu Lys Asp Arg Ser Lys Gly Val Lys Asp
    210                 215                 220

Pro Glu Ala Arg Glu Leu Ile Lys Lys Arg Asn Arg Asn Arg Gln
225                 230                 235                 240

Asn Arg Gln Glu Asn Lys Tyr Trp Asp Ile Gln Ile Gly Tyr Gln Thr
                245                 250                 255

Arg Glu Val Met Cys Ile Asn Lys Thr Gly Lys Ala Ala Asp Leu Ser
            260                 265                 270

Phe Cys Gln Gln Glu Lys Leu Pro Met Thr Phe Gln Ser Cys Val Ile
        275                 280                 285

Thr Lys Glu Cys Gln Val Ser Glu Trp Ser Glu Trp Ser Pro Cys Ser
    290                 295                 300

Lys Thr Cys His Asp Met Val Ser Pro Ala Gly Thr Arg Val Arg Thr
305                 310                 315                 320

Arg Thr Ile Arg Gln Phe Pro Ile Gly Ser Lys Glu Cys Pro Glu
                325                 330                 335

Phe Glu Glu Lys Glu Pro Cys Leu Ser Gln Gly Asp Gly Val Val Pro
            340                 345                 350

Cys Ala Thr Tyr Gly Trp Arg Thr Thr Glu Trp Thr Glu Cys Arg Val
        355                 360                 365

Asp Pro Leu Leu Ser Gln Gln Asp Lys Arg Arg Gly Asn Gln Thr Ala
    370                 375                 380

Leu Cys Gly Gly Gly Ile Gln Thr Arg Glu Val Tyr Cys Val Gln Ala
385                 390                 395                 400

Asn Glu Asn Leu Leu Ser Gln Leu Ser Thr His Lys Asn Lys Glu Ala
                405                 410                 415

Ser Lys Pro Met Asp Leu Lys Leu Cys Thr Gly Pro Ile Pro Asn Thr
            420                 425                 430

Thr Gln Leu Cys His Ile Pro Cys Pro Thr Glu Cys Glu Val Ser Pro
        435                 440                 445

Trp Ser Ala Trp Gly Pro Cys Thr Tyr Glu Asn Cys Asn Asp Gln Gln
    450                 455                 460

Gly Lys Lys Gly Phe Lys Leu Arg Lys Arg Arg Ile Thr Asn Glu Pro
465                 470                 475                 480

Thr Gly Gly Ser Gly Val Thr Gly Asn Cys Pro His Leu Leu Glu Ala
                485                 490                 495

Ile Pro Cys Glu Glu Pro Ala Cys Tyr Asp Trp Lys Ala Val Arg Leu
            500                 505                 510

Gly Asp Cys Glu Pro Asp Asn Gly Lys Glu Cys Gly Pro Gly Thr Gln
        515                 520                 525

Val Gln Glu Val Val Cys Ile Asn Ser Asp Gly Glu Glu Val Asp Arg
```

```
                530               535                540
Gln Leu Cys Arg Asp Ala Ile Phe Pro Ile Pro Val Ala Cys Asp Ala
545                 550                 555                 560

Pro Cys Pro Lys Asp Cys Val Leu Ser Thr Trp Ser Thr Trp Ser Ser
                565                 570                 575

Cys Ser His Thr Cys Ser Gly Lys Thr Thr Glu Gly Lys Gln Ile Arg
            580                 585                 590

Ala Arg Ser Ile Leu Ala Tyr Ala Gly Glu Gly Gly Ile Arg Cys
        595                 600                 605

Pro Asn Ser Ser Ala Leu Gln Glu Val Arg Ser Cys Asn Glu His Pro
    610                 615                 620

Cys Thr Val Tyr His Trp Gln Thr Gly Pro Trp Gly Gln Cys Ile Glu
625                 630                 635                 640

Asp Thr Ser Val Ser Ser Phe Asn Thr Thr Thr Trp Asn Gly Glu
                645                 650                 655

Ala Ser Cys Ser Val Gly Met Gln Thr Arg Lys Val Ile Cys Val Arg
            660                 665                 670

Val Asn Val Gly Gln Val Gly Pro Lys Lys Cys Pro Glu Ser Leu Arg
        675                 680                 685

Pro Glu Thr Val Arg Pro Cys Leu Leu Pro Cys Lys Lys Asp Cys Ile
    690                 695                 700

Val Thr Pro Tyr Ser Asp Trp Thr Ser Cys Pro Ser Ser Cys Lys Glu
705                 710                 715                 720

Gly Asp Ser Ser Ile Arg Lys Gln Ser Arg His Arg Val Ile Ile Gln
                725                 730                 735

Leu Pro Ala Asn Gly Gly Arg Asp Cys Thr Asp Pro Leu Tyr Glu Glu
            740                 745                 750

Lys Ala Cys Glu Ala Pro Gln Ala Cys Gln Ser Tyr Arg Trp Lys Thr
        755                 760                 765

His Lys Trp Arg Arg Cys Gln Leu Val Pro Trp Ser Val Gln Gln Asp
    770                 775                 780

Ser Pro Gly Ala Gln Glu Gly Cys Gly Pro Gly Arg Gln Ala Arg Ala
785                 790                 795                 800

Ile Thr Cys Arg Lys Gln Asp Gly Gly Gln Ala Gly Ile His Glu Cys
                805                 810                 815

Leu Gln Tyr Ala Gly Pro Val Pro Ala Leu Thr Gln Ala Cys Gln Ile
            820                 825                 830

Pro Cys Gln Asp Asp Cys Gln Leu Thr Ser Trp Ser Lys Phe Ser Ser
        835                 840                 845

Cys Asn Gly Asp Cys Gly Ala Val Arg Thr Arg Lys Arg Thr Leu Val
    850                 855                 860

Gly Lys Ser Lys Lys Lys Glu Lys Cys Lys Asn Ser His Leu Tyr Pro
865                 870                 875                 880

Leu Ile Glu Thr Gln Tyr Cys Pro Cys Asp Lys Tyr Asn Ala Gln Pro
                885                 890                 895

Val Gly Asn Trp Ser Asp Cys Ile Leu Pro Glu Gly Lys Val Glu Val
            900                 905                 910

Leu Leu Gly Met Lys Val Gln Gly Asp Ile Lys Glu Cys Gly Gln Gly
        915                 920                 925

Tyr Arg Tyr Gln Ala Met Ala Cys Tyr Asp Gln Asn Gly Arg Leu Val
    930                 935                 940

Glu Thr Ser Arg Cys Asn Ser His Gly Tyr Ile Glu Glu Ala Cys Ile
945                 950                 955                 960
```

```
Ile Pro Cys Pro Ser Asp Cys Lys Leu Ser Glu Trp Ser Asn Trp Ser
                965                 970                 975

Arg Cys Ser Lys Ser Cys Gly Ser Gly Val Lys Val Arg Ser Lys Trp
            980                 985                 990

Leu Arg Glu Lys Pro Tyr Asn Gly Gly Arg Pro Cys Pro Lys Leu Asp
        995                 1000                1005

His Val Asn Gln Ala Gln Val Tyr Glu Val Val Pro Cys His Ser Asp
    1010                1015                1020

Cys Asn Gln Tyr Leu Trp Val Thr Glu Pro Trp Ser Ile Cys Lys Val
1025                1030                1035                1040

Thr Phe Val Asn Met Arg Glu Asn Cys Gly Glu Gly Val Gln Thr Arg
            1045                1050                1055

Lys Val Arg Cys Met Gln Asn Thr Ala Asp Gly Pro Ser Glu His Val
                1060                1065                1070

Glu Asp Tyr Leu Cys Asp Pro Glu Met Pro Leu Gly Ser Arg Val
        1075                1080                1085

Cys Lys Leu Pro Cys Pro Glu Asp Cys Val Ile Ser Glu Trp Gly Pro
            1090                1095                1100

Trp Thr Gln Cys Val Leu Pro Cys Asn Gln Ser Ser Phe Arg Gln Arg
1105                1110                1115                1120

Ser Ala Asp Pro Ile Arg Gln Pro Ala Asp Glu Gly Arg Ser Cys Pro
                1125                1130                1135

Asn Ala Val Glu Lys Glu Pro Cys Asn Leu Asn Lys Asn Cys Tyr His
            1140                1145                1150

Tyr Asp Tyr Asn Val Thr Asp Trp Ser Thr Cys Gln Leu Ser Glu Lys
        1155                1160                1165

Ala Val Cys Gly Asn Gly Ile Lys Thr Arg Met Leu Asp Cys Val Arg
    1170                1175                1180

Ser Asp Gly Lys Ser Val Asp Leu Lys Tyr Cys Glu Ala Leu Gly Leu
1185                1190                1195                1200

Glu Lys Asn Trp Gln Met Asn Thr Ser Cys Met Val Glu Cys Pro Val
            1205                1210                1215

Asn Cys Gln Leu Ser Asp Trp Ser Pro Trp Ser Glu Cys Ser Gln Thr
        1220                1225                1230

Cys Gly Leu Thr Gly Lys Met Ile Arg Arg Arg Thr Val Thr Gln Pro
    1235                1240                1245

Phe Gln Gly Asp Gly Arg Pro Cys Pro Ser Leu Met Asp Gln Ser Lys
        1250                1255                1260

Pro Cys Pro Val Lys Pro Cys Tyr Arg Trp Gln Tyr Gly Gln Trp Ser
1265                1270                1275                1280

Pro Cys Gln Val Gln Glu Ala Gln Cys Gly Glu Gly Thr Arg Thr Arg
            1285                1290                1295

Asn Ile Ser Cys Val Val Ser Asp Gly Ser Ala Asp Asp Phe Ser Lys
        1300                1305                1310

Val Val Asp Glu Glu Phe Cys Ala Asp Ile Glu Leu Ile Ile Asp Gly
    1315                1320                1325

Asn Lys Asn Met Val Leu Glu Glu Ser Cys Ser Gln Pro Cys Pro Gly
    1330                1335                1340

Asp Cys Tyr Leu Lys Asp Trp Ser Ser Trp Ser Leu Cys Gln Leu Thr
1345                1350                1355                1360

Cys Val Asn Gly Glu Asp Leu Gly Phe Gly Gly Ile Gln Val Arg Ser
            1365                1370                1375
```

```
Arg Pro Val Ile Ile Gln Glu Leu Glu Asn Gln His Leu Cys Pro Glu
        1380                1385                1390

Gln Met Leu Glu Thr Lys Ser Cys Tyr Asp Gly Gln Cys Tyr Glu Tyr
    1395                1400                1405

Lys Trp Met Ala Ser Ala Trp Lys Gly Ser Ser Arg Thr Val Trp Cys
    1410                1415                1420

Gln Arg Ser Asp Gly Ile Asn Val Thr Gly Gly Cys Leu Val Met Ser
1425                1430                1435                1440

Gln Pro Asp Ala Asp Arg Ser Cys Asn Pro Pro Cys Ser Gln Pro His
            1445                1450                1455

Ser Tyr Cys Ser Glu Thr Lys Thr Cys His Cys Glu Glu Gly Tyr Thr
        1460                1465                1470

Glu Val Met Ser Ser Asn Ser Thr Leu Glu Gln Cys Thr Leu Ile Pro
    1475                1480                1485

Val Val Val Leu Pro Thr Met Glu Asp Lys Arg Gly Asp Val Lys Thr
    1490                1495                1500

Ser Arg Ala Val His Pro Thr Gln Pro Ser Ser Asn Pro Ala Gly Arg
1505                1510                1515                1520

Gly Arg Thr Trp Phe Leu Gln Pro Phe Gly Pro Asp Gly Arg Leu Lys
            1525                1530                1535

Thr Trp Val Tyr Gly Val Ala Ala Gly Ala Phe Val Leu Leu Ile Phe
        1540                1545                1550

Ile Val Ser Met Ile Tyr Leu Ala Cys Lys Lys Pro Lys Lys Pro Gln
        1555                1560                1565

Arg Arg Gln Asn Asn Arg Leu Lys Pro Leu Thr Leu Ala Tyr Asp Gly
    1570                1575                1580

Asp Ala Asp Met
1585

<210> SEQ ID NO 3
<211> LENGTH: 1894
<212> TYPE: DNA
<213> ORGANISM: Homo sapiens
<220> FEATURE:
<221> NAME/KEY: CDS
<222> LOCATION: (732)..(1532)

<400> SEQUENCE: 3
cacccctctg cctgccccag cccgcccatc gcttcccctt tggagcctcc tgctgggcca      60
ctggctggga tcaggacacc agtgatggta agtgctggcc cagactgaag ctcggagagg     120
cactctgctt gcccagcgtc acagtcttag ctcccaactg tcctggcttc cagtctccct     180
tgcttcccag atcccagact ctagcccccag ccccgtctct ttcaccagct cctgggaccc    240
tacgcaatct gcgcctgcgt ctcatcagtc gccccacatg taactgtatc tacaaccagc     300
tgcaccagcg acacctgtcc aacccggccc ggcctgggat gctatgtggg ggcccccagc     360 ctgggtgca gggcccctgt caggtctgat agggagaaga gaaggagcag aaggggaggg      420
gcctaaccct gggctggggg ttggactcac aggactgggg gaaagagctg caatcagagg     480
gtgtctgcca tagctgggct caggcatctg tccttggctt tgttgcctgg ctccagggag     540
attccggggg ccctgtgctg tgcctcgagc ctgacggaca ctgggttcag gctggcatca    600
tcagctttgc atcaagctgt gcccaggagg acgctcctgt gctgctgacc aacacagctg     660
ctcacagttc ctggctgcag gctcgagttc aggggcagc tttcctggcc agagcccag      720 agaccccgga g atg agt gat gag gac agc tgt gta gcc tgt gga tcc ttg    770
             Met Ser Asp Glu Asp Ser Cys Val Ala Cys Gly Ser Leu
```

```
                         1                   5                          10
agg aca gca ggt ccc cag gca gga gca ccc tcc cca tgg ccc tgg gag         818
Arg Thr Ala Gly Pro Gln Ala Gly Ala Pro Ser Pro Trp Pro Trp Glu
 15                  20                  25 gcc agg ctg atg cac cag gga cag ctg gcc tgt ggc gga gcc ctg gtg         866
Ala Arg Leu Met His Gln Gly Gln Leu Ala Cys Gly Gly Ala Leu Val
 30                  35                  40                  45 tca gag gag gcg gtg cta act gct gcc cac tgc ttc aat ggg cgc cag         914
Ser Glu Glu Ala Val Leu Thr Ala Ala His Cys Phe Asn Gly Arg Gln
                 50                  55                  60 gcc cca gag gaa tgg agc gta ggg ctg ggg acc aga ccg gag gag tgg         962
Ala Pro Glu Glu Trp Ser Val Gly Leu Gly Thr Arg Pro Glu Glu Trp
             65                  70                  75 ggc ctg aag cag ctc atc ctg cat gga gcc tac acc cac cct gag ggg        1010
Gly Leu Lys Gln Leu Ile Leu His Gly Ala Tyr Thr His Pro Glu Gly
         80                  85                  90 ggc tac gac atg gcc ctc ctg ctg gct cag cct gtg aca ctg gga            1058
Gly Tyr Asp Met Ala Leu Leu Leu Ala Gln Pro Val Thr Leu Gly
 95                 100                 105 gcc agc ctg cgg gcc ctc tgc ctg ccc tat ttt gac cac cac ctg cct        1106
Ala Ser Leu Arg Ala Leu Cys Leu Pro Tyr Phe Asp His His Leu Pro
110                 115                 120                 125 gat ggg gag cgt ggc tgg gtt ctg gga cgg gcc cgc cca gga gca ggc        1154
Asp Gly Glu Arg Gly Trp Val Leu Gly Arg Ala Arg Pro Gly Ala Gly
                130                 135                 140 atc agc tcc ctc cag aca gtg ccc gtg acc ctc ctg ggg cct agg gcc        1202
Ile Ser Ser Leu Gln Thr Val Pro Val Thr Leu Leu Gly Pro Arg Ala
            145                 150                 155 tgc agc cgg ctg cat gca gct cct ggg ggt gat ggc agc cct att ctg        1250
Cys Ser Arg Leu His Ala Ala Pro Gly Gly Asp Gly Ser Pro Ile Leu
        160                 165                 170 ccg ggg atg gtg tgt acc agt gct gtg ggt gag ctg ccc agc tgt gag        1298
Pro Gly Met Val Cys Thr Ser Ala Val Gly Glu Leu Pro Ser Cys Glu
175                 180                 185 ggc ctg tct ggg gca cca ctg gtg cat gag gtg agg ggc aca tgg ttc        1346
Gly Leu Ser Gly Ala Pro Leu Val His Glu Val Arg Gly Thr Trp Phe
190                 195                 200                 205 ctg gcc ggg ctg cac agc ttc gga gat gct tgc caa ggc ccc gcc agg        1394
Leu Ala Gly Leu His Ser Phe Gly Asp Ala Cys Gln Gly Pro Ala Arg
                210                 215                 220 ccg gcg gtc ttc acc gcg ctc cct gcc tat gag gac tgg gtc agc agt        1442
Pro Ala Val Phe Thr Ala Leu Pro Ala Tyr Glu Asp Trp Val Ser Ser
            225                 230                 235 ttg gac tgg cag gtc tac ttc gcc gag gaa cca gag ccc gag gct gag        1490
Leu Asp Trp Gln Val Tyr Phe Ala Glu Glu Pro Glu Pro Glu Ala Glu
        240                 245                 250 cct gga agc tgc ctg gcc aac ata agc caa cca acc agc tgc                1532
Pro Gly Ser Cys Leu Ala Asn Ile Ser Gln Pro Thr Ser Cys
255                 260                 265 tgacagggga cctggccatt ctcaggacaa gagaatgcag gcaggcaaat ggcattactg      1592
cccctgtcct ccccaccctg tcatgtgtga ttccaggcac cagggcaggc ccagaagccc      1652
agcagctgtg ggaaggaacc tgcctggggc cacaggtgcc ccctccccac cctgcaggac      1712 agggtgtct gtggacactc ccacacccaa ctctgctacc aagcaggcgt ctcagctttc       1772
ctcctccttt acccttcag atacaatcac gccagccccg ttgttttgaa aatttctttt       1832 tttgggggc agcagttttc cttttttaa acttaaataa attgttacaa aatagacttt        1892
ag                                                                     1894
```

<210> SEQ ID NO 4
<211> LENGTH: 267
<212> TYPE: PRT
<213> ORGANISM: Homo sapiens

<400> SEQUENCE: 4

Met Ser Asp Glu Asp Ser Cys Val Ala Cys Gly Ser Leu Arg Thr Ala
 1               5                  10                  15
Gly Pro Gln Ala Gly Ala Pro Ser Pro Trp Pro Trp Glu Ala Arg Leu
                20                  25                  30
Met His Gln Gly Gln Leu Ala Cys Gly Gly Ala Leu Val Ser Glu Glu
            35                  40                  45
Ala Val Leu Thr Ala Ala His Cys Phe Asn Gly Arg Gln Ala Pro Glu
        50                  55                  60
Glu Trp Ser Val Gly Leu Gly Thr Arg Pro Glu Glu Trp Gly Leu Lys
65                  70                  75                  80
Gln Leu Ile Leu His Gly Ala Tyr Thr His Pro Glu Gly Gly Tyr Asp
                85                  90                  95
Met Ala Leu Leu Leu Ala Gln Pro Val Thr Leu Gly Ala Ser Leu
            100                 105                 110
Arg Ala Leu Cys Leu Pro Tyr Phe Asp His His Leu Pro Asp Gly Glu
        115                 120                 125
Arg Gly Trp Val Leu Gly Arg Ala Arg Pro Gly Ala Gly Ile Ser Ser
    130                 135                 140
Leu Gln Thr Val Pro Val Thr Leu Leu Gly Pro Arg Ala Cys Ser Arg
145                 150                 155                 160
Leu His Ala Ala Pro Gly Gly Asp Gly Ser Pro Ile Leu Pro Gly Met
                165                 170                 175
Val Cys Thr Ser Ala Val Gly Glu Leu Pro Ser Cys Glu Gly Leu Ser
            180                 185                 190
Gly Ala Pro Leu Val His Glu Val Arg Gly Thr Trp Phe Leu Ala Gly
        195                 200                 205
Leu His Ser Phe Gly Asp Ala Cys Gln Gly Pro Ala Arg Pro Ala Val
    210                 215                 220
Phe Thr Ala Leu Pro Ala Tyr Glu Asp Trp Val Ser Ser Leu Asp Trp
225                 230                 235                 240
Gln Val Tyr Phe Ala Glu Glu Pro Glu Ala Glu Pro Gly Ser
                245                 250                 255
Cys Leu Ala Asn Ile Ser Gln Pro Thr Ser Cys
            260                 265

<210> SEQ ID NO 5
<211> LENGTH: 1855
<212> TYPE: DNA
<213> ORGANISM: Homo sapiens
<220> FEATURE:
<221> NAME/KEY: CDS
<222> LOCATION: (154)..(1368)

<400> SEQUENCE: 5
gcggatcctc acacgactgt gatccgattc tttccagcgg cttctgcaac caagcgggtc      60 ttaccccgg tcctccgcgt ctccagtcct cgcacctgga accccaacgt ccccgagagt      120
ccccgaatcc ccgctcccag gctacctaag agg atg agc ggt gct ccg acg gcc      174
                                    Met Ser Gly Ala Pro Thr Ala
                                     1               5

-continued

```
ggg gca gcc ctg atg ctc tgc gcc gcc acc gcc gtg cta ctg agc gct    222
Gly Ala Ala Leu Met Leu Cys Ala Ala Thr Ala Val Leu Leu Ser Ala
         10              15              20 cag ggc gga ccc gtg cag tcc aag tcg ccg cgc ttt gcg tcc tgg gac    270
Gln Gly Gly Pro Val Gln Ser Lys Ser Pro Arg Phe Ala Ser Trp Asp
 25              30              35 gag atg aat gtc ctg gcg cac gga ctc ctg cag ctc ggc cag ggg tgc    318
Glu Met Asn Val Leu Ala His Gly Leu Leu Gln Leu Gly Gln Gly Cys
 40              45              50              55 gcg aac acc gga gcg cac ccg cag tca gct gag cgc gct gga gcg cgc    366
Ala Asn Thr Gly Ala His Pro Gln Ser Ala Glu Arg Ala Gly Ala Arg
             60              65              70 ctg agc gcg tgc ggg tcc gcc tgt cag gga acc gag ggg tcc acc gac    414
Leu Ser Ala Cys Gly Ser Ala Cys Gln Gly Thr Glu Gly Ser Thr Asp
         75              80              85 ctc ccg tta gcc cct gag agc cgg gtg gac cct gag gtc ctt cac agc    462
Leu Pro Leu Ala Pro Glu Ser Arg Val Asp Pro Glu Val Leu His Ser
         90              95             100 ctg cag aca caa ctc aag gct cag aac agc agg atc cag caa ctc ttc    510
Leu Gln Thr Gln Leu Lys Ala Gln Asn Ser Arg Ile Gln Gln Leu Phe
    105             110             115 cac aag gtg gcc cag cag cag cgg cac ctg gag aag cag cac ctg cga    558
His Lys Val Ala Gln Gln Gln Arg His Leu Glu Lys Gln His Leu Arg
120             125             130             135 att cag cat ctg caa agc cag ttt ggc ctc ctg gac cac aag cac cta    606
Ile Gln His Leu Gln Ser Gln Phe Gly Leu Leu Asp His Lys His Leu
             140             145             150 gac cat gag gtg gcc aag cct gcc cga aga aag agg ctg ccc gag atg    654
Asp His Glu Val Ala Lys Pro Ala Arg Arg Lys Arg Leu Pro Glu Met
         155             160             165 gcc cag cca gtt gac ccg gct cac aat gtc agc cgc ctg cac cgg ctg    702
Ala Gln Pro Val Asp Pro Ala His Asn Val Ser Arg Leu His Arg Leu
        170             175             180 ccc agg gat tgc cag gag ctg ttc cag gtt ggg gag agg cag agt gga    750
Pro Arg Asp Cys Gln Glu Leu Phe Gln Val Gly Glu Arg Gln Ser Gly
185             190             195 cta ttt gaa atc cag cct cag ggg tct ccg cca ttt ttg gtg aac tgc    798
Leu Phe Glu Ile Gln Pro Gln Gly Ser Pro Pro Phe Leu Val Asn Cys
200             205             210             215 aag atg acc tca gat gga ggc tgg aca gta att cag agg cgc cac gat    846
Lys Met Thr Ser Asp Gly Gly Trp Thr Val Ile Gln Arg Arg His Asp
             220             225             230 ggc tca gtg gac ttc aac cgg ccc tgg gaa gcc tac aag gcg ggg ttt    894
Gly Ser Val Asp Phe Asn Arg Pro Trp Glu Ala Tyr Lys Ala Gly Phe
         235             240             245 ggg gat ccc cac ggc gag ttc tgg ctg ggt ctg gag aag gtg cat agc    942
Gly Asp Pro His Gly Glu Phe Trp Leu Gly Leu Glu Lys Val His Ser
         250             255             260 atg atg ggg gac cgc aac agc cgc ctg gcc gtg cag ctg cgg gac tgg    990
Met Met Gly Asp Arg Asn Ser Arg Leu Ala Val Gln Leu Arg Asp Trp
    265             270             275 gat ggc aac gcc gag ttg ctg cag ttc tcc gtg cac ctg ggt ggc gag   1038
Asp Gly Asn Ala Glu Leu Leu Gln Phe Ser Val His Leu Gly Gly Glu
280             285             290             295 gac acg gcc tat agc ctg cag ctc act gca ccc gtg gcc ggc cag ctg   1086
Asp Thr Ala Tyr Ser Leu Gln Leu Thr Ala Pro Val Ala Gly Gln Leu
             300             305             310 ggc gcc acc acc gtc cca ccc agc ggc ctc tcc gta ccc ttc tcc act   1134
Gly Ala Thr Thr Val Pro Pro Ser Gly Leu Ser Val Pro Phe Ser Thr
         315             320             325
```

```
tgg gac cag gat cac gac ctc cgc agg gac aag aac tgc gcc aag agc      1182
Trp Asp Gln Asp His Asp Leu Arg Arg Asp Lys Asn Cys Ala Lys Ser
            330                 335                 340 ctc tct gga ggc tgg tgg ttt ggc acc tgc agc cat tcc aac ctc aac      1230
Leu Ser Gly Gly Trp Trp Phe Gly Thr Cys Ser His Ser Asn Leu Asn
345                 350                 355 ggc cag tac ttc cgc tcc atc cca cag cag cgg cag aag ctt aag aag      1278
Gly Gln Tyr Phe Arg Ser Ile Pro Gln Gln Arg Gln Lys Leu Lys Lys
360                 365                 370                 375 gga atc ttc tgg aag acc tgg cgg ggc cgc tac tac ccg ctg cag gcc      1326
Gly Ile Phe Trp Lys Thr Trp Arg Gly Arg Tyr Tyr Pro Leu Gln Ala
            380                 385                 390 acc acc atg ttg atc cag ccc atg gca gca gag gca gcc tcc                1368
Thr Thr Met Leu Ile Gln Pro Met Ala Ala Glu Ala Ala Ser
            395                 400                 405 tagcgtcctg gctgggcctg gtcccaggcc cacgaaagac ggtgactctt ggctctgccc      1428
gaggatgtgg ccgttccctg cctgggcagg ggctccaagg agggggccatc tggaaacttg     1488 tggacagaga agaagaccac gactggagaa gccccctttc tgagtgcagg ggggctgcat      1548
gcgttgcctc ctgagatcga ggctgcagga tatgctcaga ctctagaggc gtggaccaag      1608
gggcatggag cttcactcct tgctggccag ggagttgggg actcagaggg accacttggg      1668
gccagccaga ctggcctcaa tggcggactc agtcacattg actgacgggg accagggctt      1728
gtgtgggtcg agagcgccct catggtgctg gtgctgttgt gtgtaggtcc cctggggaca      1788
caagcaggcg ccaatggtat ctgggcggag ctcacagagt tcttggaata aaagcaacct      1848
cagaaca                                                                1855

<210> SEQ ID NO 6
<211> LENGTH: 405
<212> TYPE: PRT
<213> ORGANISM: Homo sapiens

<400> SEQUENCE: 6

Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Asp Glu Met Asn Val Leu Ala His Gly Leu
        35                  40                  45

Leu Gln Leu Gly Gln Gly Cys Ala Asn Thr Gly Ala His Pro Gln Ser
    50                  55                  60

Ala Glu Arg Ala Gly Ala Arg Leu Ser Ala Cys Gly Ser Ala Cys Gln
65                  70                  75                  80

Gly Thr Glu Gly Ser Thr Asp Leu Pro Leu Ala Pro Glu Ser Arg Val
                85                  90                  95

Asp Pro Glu Val Leu His Ser Leu Gln Thr Gln Leu Lys Ala Gln Asn
            100                 105                 110

Ser Arg Ile Gln Gln Leu Phe His Lys Val Ala Gln Gln Gln Arg His
        115                 120                 125

Leu Glu Lys Gln His Leu Arg Ile Gln His Leu Gln Ser Gln Phe Gly
    130                 135                 140

Leu Leu Asp His Lys His Leu Asp His Glu Val Ala Lys Pro Ala Arg
145                 150                 155                 160

Arg Lys Arg Leu Pro Glu Met Ala Gln Pro Val Asp Pro Ala His Asn
                165                 170                 175
```

```
Val Ser Arg Leu His Arg Leu Pro Arg Asp Cys Gln Glu Leu Phe Gln
        180                 185                 190

Val Gly Glu Arg Gln Ser Gly Leu Phe Glu Ile Gln Pro Gln Gly Ser
        195                 200                 205

Pro Pro Phe Leu Val Asn Cys Lys Met Thr Ser Asp Gly Gly Trp Thr
        210                 215                 220

Val Ile Gln Arg Arg His Asp Gly Ser Val Asp Phe Asn Arg Pro Trp
225                 230                 235                 240

Glu Ala Tyr Lys Ala Gly Phe Gly Asp Pro His Gly Glu Phe Trp Leu
                245                 250                 255

Gly Leu Glu Lys Val His Ser Met Met Gly Asp Arg Asn Ser Arg Leu
            260                 265                 270

Ala Val Gln Leu Arg Asp Trp Asp Gly Asn Ala Glu Leu Leu Gln Phe
        275                 280                 285

Ser Val His Leu Gly Gly Glu Asp Thr Ala Tyr Ser Leu Gln Leu Thr
        290                 295                 300

Ala Pro Val Ala Gly Gln Leu Gly Ala Thr Thr Val Pro Pro Ser Gly
305                 310                 315                 320

Leu Ser Val Pro Phe Ser Thr Trp Asp Gln Asp His Asp Leu Arg Arg
                325                 330                 335

Asp Lys Asn Cys Ala Lys Ser Leu Ser Gly Gly Trp Trp Phe Gly Thr
            340                 345                 350

Cys Ser His Ser Asn Leu Asn Gly Gln Tyr Phe Arg Ser Ile Pro Gln
        355                 360                 365

Gln Arg Gln Lys Leu Lys Lys Gly Ile Phe Trp Lys Thr Trp Arg Gly
        370                 375                 380

Arg Tyr Tyr Pro Leu Gln Ala Thr Thr Met Leu Ile Gln Pro Met Ala
385                 390                 395                 400

Ala Glu Ala Ala Ser
                405

<210> SEQ ID NO 7
<211> LENGTH: 3026
<212> TYPE: DNA
<213> ORGANISM: Homo sapiens
<220> FEATURE:
<221> NAME/KEY: CDS
<222> LOCATION: (55)..(2382)

<400> SEQUENCE: 7
ggtagccgac gcgccggccg gcgcgtgacc ttgcccctct tgctcgcctt gaaa atg      57
                                                              Met
                                                              1 gaa aag atg ctc gca ggc tgc ttt ctg ctg atc ctc gga cag atc gtc     105
Glu Lys Met Leu Ala Gly Cys Phe Leu Leu Ile Leu Gly Gln Ile Val
            5                   10                  15 ctc ctc cct gcc gag gcc agg gag cgg tca cgt ggg agg tcc atc tct    153
Leu Leu Pro Ala Glu Ala Arg Glu Arg Ser Arg Gly Arg Ser Ile Ser
        20                  25                  30 agg ggc aga cac gct cgg acc cac ccg cag acg gcc ctt ctg gag agt    201
Arg Gly Arg His Ala Arg Thr His Pro Gln Thr Ala Leu Leu Glu Ser
    35                  40                  45 tcc tgt gag aac aag cgg gca gac ctg gtt ttc atc att gac agc tct    249
Ser Cys Glu Asn Lys Arg Ala Asp Leu Val Phe Ile Ile Asp Ser Ser
50                  55                  60                  65 cgc agt gtc aac acc cat gac tat gca aag gtc aag gag ttc atc gtg    297
Arg Ser Val Asn Thr His Asp Tyr Ala Lys Val Lys Glu Phe Ile Val
```

-continued

```
                 70                 75                 80
gac atc ttg caa ttc ttg gac att ggt cct gat gtc acc cga gtg ggc      345
Asp Ile Leu Gln Phe Leu Asp Ile Gly Pro Asp Val Thr Arg Val Gly
             85                 90                 95 ctg ctc caa tat ggc agc act gtc aag aat gag ttc tcc ctc aag acc      393
Leu Leu Gln Tyr Gly Ser Thr Val Lys Asn Glu Phe Ser Leu Lys Thr
            100                105                110 ttc aag agg aag tcc gag gtg gag cgt gct gtc aag agg atg cgg cat      441
Phe Lys Arg Lys Ser Glu Val Glu Arg Ala Val Lys Arg Met Arg His
    115                120                125 ctg tcc acg ggc acc atg act ggg ctg gcc atc cag tat gcc ctg aac      489
Leu Ser Thr Gly Thr Met Thr Gly Leu Ala Ile Gln Tyr Ala Leu Asn
130                135                140                145 atc gca ttc tca gaa gca gag ggg gcc cgg ccc ctg agg gag aat gtg      537
Ile Ala Phe Ser Glu Ala Glu Gly Ala Arg Pro Leu Arg Glu Asn Val
                150                155                160 cca cgg gtc ata atg atc gtg acg gat ggg aga cct cag gac tcc gtg      585
Pro Arg Val Ile Met Ile Val Thr Asp Gly Arg Pro Gln Asp Ser Val
            165                170                175 gcc gag gtg gct gct aag gca cgg gac acg ggc atc cta atc ttt gcc      633
Ala Glu Val Ala Ala Lys Ala Arg Asp Thr Gly Ile Leu Ile Phe Ala
        180                185                190 att ggt gtg ggc cag gta gac ttc aac acc ttg aag tcc att ggg agt      681
Ile Gly Val Gly Gln Val Asp Phe Asn Thr Leu Lys Ser Ile Gly Ser
    195                200                205 gag ccc cat gag gac cat gtc ttc ctt gtg gcc aat ttc agc cag att      729
Glu Pro His Glu Asp His Val Phe Leu Val Ala Asn Phe Ser Gln Ile
210                215                220                225 gag acg ctg acc tcc gtg ttc cag aag aag ttg tgc acg gcc cac atg      777
Glu Thr Leu Thr Ser Val Phe Gln Lys Lys Leu Cys Thr Ala His Met
                230                235                240 tgc agc acc ctg gag cat aac tgt gcc cac ttc tgc atc aac atc cct      825
Cys Ser Thr Leu Glu His Asn Cys Ala His Phe Cys Ile Asn Ile Pro
            245                250                255 ggc tca tac gtc tgc agg tgc aaa caa ggc tac att ctc aac tcg gat      873
Gly Ser Tyr Val Cys Arg Cys Lys Gln Gly Tyr Ile Leu Asn Ser Asp
        260                265                270 cag acg act tgc aga atc cag gat ctg tgt gcc atg gag gac cac aac      921
Gln Thr Thr Cys Arg Ile Gln Asp Leu Cys Ala Met Glu Asp His Asn
    275                280                285 tgt gag cag ctc tgt gtg aat gtg ccg ggc tcc ttc gtc tgc gag tgc      969
Cys Glu Gln Leu Cys Val Asn Val Pro Gly Ser Phe Val Cys Glu Cys
290                295                300                305 tac agt ggc tac gcc ctg gct gag gat ggg aag agg tgt gtg gct gtg     1017
Tyr Ser Gly Tyr Ala Leu Ala Glu Asp Gly Lys Arg Cys Val Ala Val
                310                315                320 gac tac tgt gcc tca gaa aac cac gga tgt gaa cat gag tgt gta aat     1065
Asp Tyr Cys Ala Ser Glu Asn His Gly Cys Glu His Glu Cys Val Asn
            325                330                335 gct gat ggc tcc tac ctt tgc cag tgc cat gaa gga ttt gct ctt aac     1113
Ala Asp Gly Ser Tyr Leu Cys Gln Cys His Glu Gly Phe Ala Leu Asn
        340                345                350 cca gat gaa aaa acg tgc aca aag ata gac tac tgt gcc tca tct aat     1161
Pro Asp Glu Lys Thr Cys Thr Lys Ile Asp Tyr Cys Ala Ser Ser Asn
    355                360                365 cat gga tgt cag tac gag tgt gtt aac aca gat gat tcc tat tcc tgc     1209
His Gly Cys Gln Tyr Glu Cys Val Asn Thr Asp Asp Ser Tyr Ser Cys
370                375                380                385 cac tgc ctg aaa ggc ttt acc ctg aat cca gat aag aaa acc tgc aga     1257
```

```
                His Cys Leu Lys Gly Phe Thr Leu Asn Pro Asp Lys Lys Thr Cys Arg
                            390                 395                 400 agg atc aac tac tgt gca ctg aac aaa ccg ggc tgt gag cat gag tgc        1305
Arg Ile Asn Tyr Cys Ala Leu Asn Lys Pro Gly Cys Glu His Glu Cys
            405                 410                 415 gtc aac atg gag gag agc tac tac tgc cgc tgc cac cgt ggc tac act        1353
Val Asn Met Glu Glu Ser Tyr Tyr Cys Arg Cys His Arg Gly Tyr Thr
            420                 425                 430 ctg gac ccc aat ggc aaa ccc tgc agc cga gtg gac cac tgt gca cag        1401
Leu Asp Pro Asn Gly Lys Pro Cys Ser Arg Val Asp His Cys Ala Gln
435                 440                 445 cag gac cat ggc tgt gag cag ctg tgt ctg aac acg gag gat tcc ttc        1449
Gln Asp His Gly Cys Glu Gln Leu Cys Leu Asn Thr Glu Asp Ser Phe
450                 455                 460                 465 gtc tgc cag tgc tca gaa ggc ttc ctc atc aac gag gac ctc aag acc        1497
Val Cys Gln Cys Ser Glu Gly Phe Leu Ile Asn Glu Asp Leu Lys Thr
            470                 475                 480 tgc tcc cgg gtg gat tac tgc ctg ctg agt gac cat ggt tgt gaa tac        1545
Cys Ser Arg Val Asp Tyr Cys Leu Leu Ser Asp His Gly Cys Glu Tyr
            485                 490                 495 tcc tgt gtc aac atg gac aga tcc ttt gcc tgt cag tgt cct gag gga        1593
Ser Cys Val Asn Met Asp Arg Ser Phe Ala Cys Gln Cys Pro Glu Gly
            500                 505                 510 cac gtg ctc cgc agc gat ggg aag acg tgt gca aaa ttg gac tct tgt        1641
His Val Leu Arg Ser Asp Gly Lys Thr Cys Ala Lys Leu Asp Ser Cys
            515                 520                 525 gct ctg ggg gac cac ggt tgt gaa cat tcg tgt gta agc agt gaa gat        1689
Ala Leu Gly Asp His Gly Cys Glu His Ser Cys Val Ser Ser Glu Asp
530                 535                 540                 545 tcg ttt gtg tgc cag tgc ttt gaa ggt tat ata ctc cgt gaa gat gga        1737
Ser Phe Val Cys Gln Cys Phe Glu Gly Tyr Ile Leu Arg Glu Asp Gly
            550                 555                 560 aaa acc tgc aga agg aaa gat gtc tgc caa gct ata gac cat ggc tgt        1785
Lys Thr Cys Arg Arg Lys Asp Val Cys Gln Ala Ile Asp His Gly Cys
            565                 570                 575 gaa cac att tgt gtg aac agt gac gac tca tac acg tgc gag tgc ttg        1833
Glu His Ile Cys Val Asn Ser Asp Asp Ser Tyr Thr Cys Glu Cys Leu
            580                 585                 590 gag gga ttc cgg ctc act gag gat ggg aaa cgc tgc cga att tcc tca        1881
Glu Gly Phe Arg Leu Thr Glu Asp Gly Lys Arg Cys Arg Ile Ser Ser
            595                 600                 605 ggg aag gat gtc tgc aaa tca acc cac cat ggc tgc gaa cac att tgt        1929
Gly Lys Asp Val Cys Lys Ser Thr His His Gly Cys Glu His Ile Cys
610                 615                 620                 625 gtt aat aat ggg aat tcc tac atc tgc aaa tgc tca gag gga ttt gtt        1977
Val Asn Asn Gly Asn Ser Tyr Ile Cys Lys Cys Ser Glu Gly Phe Val
            630                 635                 640 cta gct gag gac gga aga cgg tgc aag aaa tgc act gaa ggc cca att        2025
Leu Ala Glu Asp Gly Arg Arg Cys Lys Lys Cys Thr Glu Gly Pro Ile
            645                 650                 655 gac ctg gtc ttt gtg atc gat gga tcc aag agt ctt gga gaa gag aat        2073
Asp Leu Val Phe Val Ile Asp Gly Ser Lys Ser Leu Gly Glu Glu Asn
            660                 665                 670 ttt gag gtc gtg aag cag ttt gtc act gga att ata gat tcc ttg aca        2121
Phe Glu Val Val Lys Gln Phe Val Thr Gly Ile Ile Asp Ser Leu Thr
            675                 680                 685 att tcc ccc aaa gcc gct cga gtg ggg ctg ctc cag tat tcc aca cag        2169
Ile Ser Pro Lys Ala Ala Arg Val Gly Leu Leu Gln Tyr Ser Thr Gln
690                 695                 700                 705
```

```
gtc cac aca gag ttc act ctg aga aac ttc aac tca gcc aaa gac atg    2217
Val His Thr Glu Phe Thr Leu Arg Asn Phe Asn Ser Ala Lys Asp Met
            710                 715                 720 aaa aaa gcc gtg gcc cac atg aaa tac atg gga aag ggc tct atg act    2265
Lys Lys Ala Val Ala His Met Lys Tyr Met Gly Lys Gly Ser Met Thr
        725                 730                 735 ggg ctg gcc ctg aaa cac atg ttt gag aga agt ttt acc caa gga gaa    2313
Gly Leu Ala Leu Lys His Met Phe Glu Arg Ser Phe Thr Gln Gly Glu
    740                 745                 750 ggg gcc agg ccc ctt ttc cac aag ggt gcc cag agc agc cat tgt gtt    2361
Gly Ala Arg Pro Leu Phe His Lys Gly Ala Gln Ser Ser His Cys Val
755                 760                 765 cac cga cgg acg ggc tca gga tgacgtctcc gagtgggcca gtaaagccaa       2412
His Arg Arg Thr Gly Ser Gly
770                 775 ggccaatggt atcactatgt atgctgttgg ggtaggaaaa gccattgagg aggaactaca   2472
agagattgcc tctgagccca caaacaagca tctcttctat gccgaagact tcagcacaat   2532
ggatgagata agtgaaaaac tcaagaaagg catctgtgaa gctctagaag actccgatgg   2592
aagacaggac tctccagcag gggaactgcc aaaaacggtc caacagccaa cagaatctga   2652
gccagtcacc ataaatatcc aagacctact ttcctgttct aattttgcag tgcaacacag   2712
atatctgttt gaagaagaca atcttttacg gtctacacaa aagctttccc attcaacaaa   2772
accttcagga agccctttgg aagaaaaaca cgatcaatgc aaatgtgaaa accttataat   2832
gttccagaac cttgcaaacg aagaagtaag aaaatttaca cagcgcttag aagaaatgac   2892
acagagaatg gaagccctgg aaaatcgcct gagatacaga tgaagattag aaatcgcgac   2952
acatttgtag tcattgtatc acggattaca atgaacgcag tgcagagccc caaagctcag   3012
gctattgtta aatc                                                    3026

<210> SEQ ID NO 8
<211> LENGTH: 776
<212> TYPE: PRT
<213> ORGANISM: Homo sapiens

<400> SEQUENCE: 8

Met Glu Lys Met Leu Ala Gly Cys Phe Leu Leu Ile Leu Gly Gln Ile
1               5                   10                  15

Val Leu Leu Pro Ala Glu Ala Arg Glu Arg Ser Arg Gly Arg Ser Ile
            20                  25                  30

Ser Arg Gly Arg His Ala Arg Thr His Pro Gln Thr Ala Leu Leu Glu
        35                  40                  45

Ser Ser Cys Glu Asn Lys Arg Ala Asp Leu Val Phe Ile Ile Asp Ser
    50                  55                  60

Ser Arg Ser Val Asn Thr His Asp Tyr Ala Lys Val Lys Glu Phe Ile
65                  70                  75                  80

Val Asp Ile Leu Gln Phe Leu Asp Ile Gly Pro Asp Val Thr Arg Val
                85                  90                  95

Gly Leu Leu Gln Tyr Gly Ser Thr Val Lys Asn Glu Phe Ser Leu Lys
            100                 105                 110

Thr Phe Lys Arg Lys Ser Glu Val Glu Arg Ala Val Lys Arg Met Arg
        115                 120                 125

His Leu Ser Thr Gly Thr Met Thr Gly Leu Ala Ile Gln Tyr Ala Leu
    130                 135                 140

Asn Ile Ala Phe Ser Glu Ala Glu Gly Ala Arg Pro Leu Arg Glu Asn
145                 150                 155                 160
```

-continued

```
Val Pro Arg Val Ile Met Ile Val Thr Asp Gly Arg Pro Gln Asp Ser
            165                 170                 175

Val Ala Glu Val Ala Ala Lys Ala Arg Asp Thr Gly Ile Leu Ile Phe
            180                 185                 190

Ala Ile Gly Val Gly Gln Val Asp Phe Asn Thr Leu Lys Ser Ile Gly
            195                 200                 205

Ser Glu Pro His Glu Asp His Val Phe Leu Val Ala Asn Phe Ser Gln
            210                 215                 220

Ile Glu Thr Leu Thr Ser Val Phe Gln Lys Lys Leu Cys Thr Ala His
225                 230                 235                 240

Met Cys Ser Thr Leu Glu His Asn Cys Ala His Phe Cys Ile Asn Ile
                245                 250                 255

Pro Gly Ser Tyr Val Cys Arg Cys Lys Gln Gly Tyr Ile Leu Asn Ser
                260                 265                 270

Asp Gln Thr Thr Cys Arg Ile Gln Asp Leu Cys Ala Met Glu Asp His
                275                 280                 285

Asn Cys Glu Gln Leu Cys Val Asn Val Pro Gly Ser Phe Val Cys Glu
        290                 295                 300

Cys Tyr Ser Gly Tyr Ala Leu Ala Glu Asp Gly Lys Arg Cys Val Ala
305                 310                 315                 320

Val Asp Tyr Cys Ala Ser Glu Asn His Gly Cys Glu His Glu Cys Val
                325                 330                 335

Asn Ala Asp Gly Ser Tyr Leu Cys Gln Cys His Glu Gly Phe Ala Leu
                340                 345                 350

Asn Pro Asp Glu Lys Thr Cys Thr Lys Ile Asp Tyr Cys Ala Ser Ser
                355                 360                 365

Asn His Gly Cys Gln Tyr Glu Cys Val Asn Thr Asp Asp Ser Tyr Ser
            370                 375                 380

Cys His Cys Leu Lys Gly Phe Thr Leu Asn Pro Asp Lys Lys Thr Cys
385                 390                 395                 400

Arg Arg Ile Asn Tyr Cys Ala Leu Asn Lys Pro Gly Cys Glu His Glu
                405                 410                 415

Cys Val Asn Met Glu Glu Ser Tyr Tyr Cys Arg Cys His Arg Gly Tyr
                420                 425                 430

Thr Leu Asp Pro Asn Gly Lys Pro Cys Ser Arg Val Asp His Cys Ala
                435                 440                 445

Gln Gln Asp His Gly Cys Glu Gln Leu Cys Leu Asn Thr Glu Asp Ser
            450                 455                 460

Phe Val Cys Gln Cys Ser Glu Gly Phe Leu Ile Asn Glu Asp Leu Lys
465                 470                 475                 480

Thr Cys Ser Arg Val Asp Tyr Cys Leu Leu Ser Asp His Gly Cys Glu
                485                 490                 495

Tyr Ser Cys Val Asn Met Asp Arg Ser Phe Ala Cys Gln Cys Pro Glu
                500                 505                 510

Gly His Val Leu Arg Ser Asp Gly Lys Thr Cys Ala Lys Leu Asp Ser
            515                 520                 525

Cys Ala Leu Gly Asp His Gly Cys Glu His Ser Cys Val Ser Ser Glu
        530                 535                 540

Asp Ser Phe Val Cys Gln Cys Phe Glu Gly Tyr Ile Leu Arg Glu Asp
545                 550                 555                 560

Gly Lys Thr Cys Arg Arg Lys Asp Val Cys Gln Ala Ile Asp His Gly
                565                 570                 575
```

```
Cys Glu His Ile Cys Val Asn Ser Asp Asp Ser Tyr Thr Cys Glu Cys
            580                 585                 590

Leu Glu Gly Phe Arg Leu Thr Glu Asp Gly Lys Arg Cys Arg Ile Ser
        595                 600                 605

Ser Gly Lys Asp Val Cys Lys Ser Thr His His Gly Cys Glu His Ile
    610                 615                 620

Cys Val Asn Asn Gly Asn Ser Tyr Ile Cys Lys Cys Ser Glu Gly Phe
625                 630                 635                 640

Val Leu Ala Glu Asp Gly Arg Arg Cys Lys Lys Cys Thr Glu Gly Pro
                645                 650                 655

Ile Asp Leu Val Phe Val Ile Asp Gly Ser Lys Ser Leu Gly Glu Glu
            660                 665                 670

Asn Phe Glu Val Val Lys Gln Phe Val Thr Gly Ile Ile Asp Ser Leu
        675                 680                 685

Thr Ile Ser Pro Lys Ala Ala Arg Val Gly Leu Leu Gln Tyr Ser Thr
    690                 695                 700

Gln Val His Thr Glu Phe Thr Leu Arg Asn Phe Asn Ser Ala Lys Asp
705                 710                 715                 720

Met Lys Lys Ala Val Ala His Met Lys Tyr Met Gly Lys Gly Ser Met
                725                 730                 735

Thr Gly Leu Ala Leu Lys His Met Phe Glu Arg Ser Phe Thr Gln Gly
            740                 745                 750

Glu Gly Ala Arg Pro Leu Phe His Lys Gly Ala Gln Ser Ser His Cys
        755                 760                 765

Val His Arg Arg Thr Gly Ser Gly
    770                 775

<210> SEQ ID NO 9
<211> LENGTH: 3447
<212> TYPE: DNA
<213> ORGANISM: Homo sapiens
<220> FEATURE:
<221> NAME/KEY: CDS
<222> LOCATION: (55)..(2931)

<400> SEQUENCE: 9
ggtagccgac gcgccggccg gcgcgtgacc ttgcccctct tgctcgcctt gaaa atg      57
                                                             Met
                                                               1 gaa aag atg ctc gca ggc tgc ttt ctg ctg atc ctc gga cag atc gtc    105
Glu Lys Met Leu Ala Gly Cys Phe Leu Leu Ile Leu Gly Gln Ile Val
          5                   10                  15 ctc ctc ccc tgc gag gcc agg gag cgg tca cgt ggg agg tcc atc tct    153
Leu Leu Pro Cys Glu Ala Arg Glu Arg Ser Arg Gly Arg Ser Ile Ser
         20                  25                  30 agg ggc aga cac gct cgg acc cac ccg cag acg gcc ctt ctg gag agt    201
Arg Gly Arg His Ala Arg Thr His Pro Gln Thr Ala Leu Leu Glu Ser
     35                  40                  45 tcc tgt gag aac aag cgg gca gac ctg gtt ttc atc att gac agc tct    249
Ser Cys Glu Asn Lys Arg Ala Asp Leu Val Phe Ile Ile Asp Ser Ser
 50                  55                  60                  65 cgc agt gtc aac acc cat gac tat gca aag gtc aag gag ttc atc gtg    297
Arg Ser Val Asn Thr His Asp Tyr Ala Lys Val Lys Glu Phe Ile Val
                 70                  75                  80 gac atc ttg caa ttc ttg gac att ggt cct gat gtc acc cga gtg ggc    345
Asp Ile Leu Gln Phe Leu Asp Ile Gly Pro Asp Val Thr Arg Val Gly
             85                  90                  95 ctg ctc caa tat ggc agc act gtc aag aat gag ttc tcc ctc aag acc    393
```

```
                          -continued

Leu Leu Gln Tyr Gly Ser Thr Val Lys Asn Glu Phe Ser Leu Lys Thr
        100                 105                 110 ttc aag agg aag tcc gag gtg gag cgt gct gtc aag agg atg cgg cat      441
Phe Lys Arg Lys Ser Glu Val Glu Arg Ala Val Lys Arg Met Arg His
    115                 120                 125 ctg tcc acg ggc acc atg act ggg ctg gcc atc cag tat gcc ctg aac      489
Leu Ser Thr Gly Thr Met Thr Gly Leu Ala Ile Gln Tyr Ala Leu Asn
130                 135                 140                 145 atc gca ttc tca gaa gca gag ggg gcc cgg ccc ctg agg gag aat gtg      537
Ile Ala Phe Ser Glu Ala Glu Gly Ala Arg Pro Leu Arg Glu Asn Val
            150                 155                 160 cca cgg gtc ata atg atc gtg acg gat ggg aga cct cag gac tcc gtg      585
Pro Arg Val Ile Met Ile Val Thr Asp Gly Arg Pro Gln Asp Ser Val
                165                 170                 175 gcc gag gtg gct gct aag gca cgg gac acg ggc atc cta atc ttt gcc      633
Ala Glu Val Ala Ala Lys Ala Arg Asp Thr Gly Ile Leu Ile Phe Ala
            180                 185                 190 att ggt gtg ggc cag gta gac ttc aac acc ttg aag tcc att ggg agt      681
Ile Gly Val Gly Gln Val Asp Phe Asn Thr Leu Lys Ser Ile Gly Ser
195                 200                 205 gag ccc cat gag gac cat gtc ttc ctt gtg gcc aat ttc agc cag att      729
Glu Pro His Glu Asp His Val Phe Leu Val Ala Asn Phe Ser Gln Ile
210                 215                 220                 225 gag acg ctg acc tcc gtg ttc cag aag aag ttg tgc acg gcc cac atg      777
Glu Thr Leu Thr Ser Val Phe Gln Lys Lys Leu Cys Thr Ala His Met
                230                 235                 240 tgc agc acc ctg gag cat aac tgt gcc cac ttc tgc atc aac atc cct      825
Cys Ser Thr Leu Glu His Asn Cys Ala His Phe Cys Ile Asn Ile Pro
            245                 250                 255 ggc tca tac gtc tgc agg tgc aaa caa ggc tac att ctc aac tcg gat      873
Gly Ser Tyr Val Cys Arg Cys Lys Gln Gly Tyr Ile Leu Asn Ser Asp
        260                 265                 270 cag acg act tgc aga atc cag gat ctg tgt gcc atg gag gac cac aac      921
Gln Thr Thr Cys Arg Ile Gln Asp Leu Cys Ala Met Glu Asp His Asn
275                 280                 285 tgt gag cag ctc tgt gtg aat gtg ccg ggc tcc ttc gtc tgc gag tgc      969
Cys Glu Gln Leu Cys Val Asn Val Pro Gly Ser Phe Val Cys Glu Cys
290                 295                 300                 305 tac agt ggc tac gcc ctg gct gag gat ggg aag agg tgt gtg gct gtg     1017
Tyr Ser Gly Tyr Ala Leu Ala Glu Asp Gly Lys Arg Cys Val Ala Val
                310                 315                 320 gac tac tgt gcc tca gaa aac cac gga tgt gaa cat gag tgt gta aat     1065
Asp Tyr Cys Ala Ser Glu Asn His Gly Cys Glu His Glu Cys Val Asn
            325                 330                 335 gct gat ggc tcc tac ctt tgc cag tgc cat gaa gga ttt gct ctt aac     1113
Ala Asp Gly Ser Tyr Leu Cys Gln Cys His Glu Gly Phe Ala Leu Asn
        340                 345                 350 cca gat gaa aaa acg tgc aca aag ata gac tac tgt gcc tca tct aat     1161
Pro Asp Glu Lys Thr Cys Thr Lys Ile Asp Tyr Cys Ala Ser Ser Asn
355                 360                 365 cat gga tgt cag tac gag tgt gtt aac aca gat gat tcc tat tcc tgc     1209
His Gly Cys Gln Tyr Glu Cys Val Asn Thr Asp Asp Ser Tyr Ser Cys
370                 375                 380                 385 cac tgc ctg aaa ggc ttt acc ctg aat cca gat aag aaa acc tgc aga     1257
His Cys Leu Lys Gly Phe Thr Leu Asn Pro Asp Lys Lys Thr Cys Arg
                390                 395                 400 agg atc aac tac tgt gca ctg aac aaa ccg ggc tgt gag cat gag tgc     1305
Arg Ile Asn Tyr Cys Ala Leu Asn Lys Pro Gly Cys Glu His Glu Cys
            405                 410                 415
```

```
                                                         -continued gtc aac atg gag gag agc tac tac tgc cgc tgc cac cgt ggc tac act      1353
Val Asn Met Glu Glu Ser Tyr Tyr Cys Arg Cys His Arg Gly Tyr Thr
        420                 425                 430 ctg gac ccc aat ggc aaa ccc tgc agc cga gtg gac cac tgt gca cag      1401
Leu Asp Pro Asn Gly Lys Pro Cys Ser Arg Val Asp His Cys Ala Gln
435                 440                 445 cag gac cat ggc tgt gag cag ctg tgt ctg aac acg gag gat tcc ttc      1449
Gln Asp His Gly Cys Glu Gln Leu Cys Leu Asn Thr Glu Asp Ser Phe
450                 455                 460                 465 gtc tgc cag tgc tca gaa ggc ttc ctc atc aac gag gac ctc aag acc      1497
Val Cys Gln Cys Ser Glu Gly Phe Leu Ile Asn Glu Asp Leu Lys Thr
            470                 475                 480 tgc tcc cgg gtg gat tac tgc ctg ctg agt gac cat ggt tgt gaa tac      1545
Cys Ser Arg Val Asp Tyr Cys Leu Leu Ser Asp His Gly Cys Glu Tyr
                485                 490                 495 tcc tgt gtc aac atg gac aga tcc ttt gcc tgt cag tgt cct gag gga      1593
Ser Cys Val Asn Met Asp Arg Ser Phe Ala Cys Gln Cys Pro Glu Gly
                    500                 505                 510 cac gtg ctc cgc agc gat ggg aag acg tgt gca aaa ttg gac tct tgt      1641
His Val Leu Arg Ser Asp Gly Lys Thr Cys Ala Lys Leu Asp Ser Cys
    515                 520                 525 gct ctg ggg gac cac ggt tgt gaa cat tcg tgt gta agc agt gaa gat      1689
Ala Leu Gly Asp His Gly Cys Glu His Ser Cys Val Ser Ser Glu Asp
530                 535                 540                 545 tcg ttt gtg tgc cag tgc ttt gaa ggt tat ata ctc cgt gaa gat gga      1737
Ser Phe Val Cys Gln Cys Phe Glu Gly Tyr Ile Leu Arg Glu Asp Gly
                550                 555                 560 aaa acc tgc aga agg aaa gat gtc tgc caa gct ata gac cat ggc tgt      1785
Lys Thr Cys Arg Arg Lys Asp Val Cys Gln Ala Ile Asp His Gly Cys
                    565                 570                 575 gaa cac att tgt gtg aac agt gac gac tca tac acg tgc gag tgc ttg      1833
Glu His Ile Cys Val Asn Ser Asp Asp Ser Tyr Thr Cys Glu Cys Leu
    580                 585                 590 gag gga ttc cgg ctc act gag gat ggg aaa cgc tgc cga att tcc tca      1881
Glu Gly Phe Arg Leu Thr Glu Asp Gly Lys Arg Cys Arg Ile Ser Ser
595                 600                 605 ggg aag gat gtc tgc aaa tca acc cac cat ggc tgc gaa cac att tgt      1929
Gly Lys Asp Val Cys Lys Ser Thr His His Gly Cys Glu His Ile Cys
                615                 620                 625 gtt aat aat ggg aat tcc tac atc tgc aaa tgc tca gag gga ttt gtt      1977
Val Asn Asn Gly Asn Ser Tyr Ile Cys Lys Cys Ser Glu Gly Phe Val
                    630                 635                 640 cta gct gag gac gga aga cgg tgc aag aaa tgc act gaa ggc cca att      2025
Leu Ala Glu Asp Gly Arg Arg Cys Lys Lys Cys Thr Glu Gly Pro Ile
                645                 650                 655 gac ctg gtc ttt gtg atc gat gga tcc aag agt ctt gga gaa gag aat      2073
Asp Leu Val Phe Val Ile Asp Gly Ser Lys Ser Leu Gly Glu Glu Asn
        660                 665                 670 ttt gag gtc gtg aag cag ttt gtc act gga att ata gat tcc ttg aca      2121
Phe Glu Val Val Lys Gln Phe Val Thr Gly Ile Ile Asp Ser Leu Thr
675                 680                 685 att tcc ccc aaa gcc gct cga gtg ggg ctg ctc cag tat tcc aca cag      2169
Ile Ser Pro Lys Ala Ala Arg Val Gly Leu Leu Gln Tyr Ser Thr Gln
690                 695                 700                 705 gtc cac aca gag ttc act ctg aga aac ttc aac tca gcc aaa gac atg      2217
Val His Thr Glu Phe Thr Leu Arg Asn Phe Asn Ser Ala Lys Asp Met
            710                 715                 720 aaa aaa gcc gtg gcc cac atg aaa tac atg gga aag ggc tct atg act      2265
Lys Lys Ala Val Ala His Met Lys Tyr Met Gly Lys Gly Ser Met Thr
                725                 730                 735
```

| | | | | | | | | | | | | | |
|---|---|---|---|---|---|---|---|---|---|---|---|---|---|
| ggg | ctg | gcc | ctg | aaa | cac | atg | ttt | gag | aga | agt | ttt | acc | caa | gga | gaa | | 2313 |
| Gly | Leu | Ala | Leu | Lys | His | Met | Phe | Glu | Arg | Ser | Phe | Thr | Gln | Gly | Glu | | |
| | | | 740 | | | | 745 | | | | 750 | | | | | | |

```
ggg gcc agg ccc ttt tcc aca agg gtg ccc aga gca gcc att gtg ttc         2361
Gly Ala Arg Pro Phe Ser Thr Arg Val Pro Arg Ala Ala Ile Val Phe
        755                 760                 765 acc gac gga cgg gct cag gat gac gtc tcc gag tgg gcc agt aaa gcc         2409
Thr Asp Gly Arg Ala Gln Asp Asp Val Ser Glu Trp Ala Ser Lys Ala
770                 775                 780                 785 aag gcc aat ggt atc act atg tat gct gtt ggg gta gga aaa gcc att         2457
Lys Ala Asn Gly Ile Thr Met Tyr Ala Val Gly Val Gly Lys Ala Ile
                790                 795                 800 gag gag gaa cta caa gag att gcc tct gag ccc aca aac aag cat ctc         2505
Glu Glu Glu Leu Gln Glu Ile Ala Ser Glu Pro Thr Asn Lys His Leu
            805                 810                 815 ttc tat gcc gaa gac ttc agc aca atg gat gag ata agt gaa aaa ctc         2553
Phe Tyr Ala Glu Asp Phe Ser Thr Met Asp Glu Ile Ser Glu Lys Leu
        820                 825                 830 aag aaa ggc atc tgt gaa gct cta gaa gac tcc gat gga aga cag gac         2601
Lys Lys Gly Ile Cys Glu Ala Leu Glu Asp Ser Asp Gly Arg Gln Asp
835                 840                 845 tct cca gca ggg gaa ctg cca aaa acg gtc caa cag cca aca gaa tct         2649
Ser Pro Ala Gly Glu Leu Pro Lys Thr Val Gln Gln Pro Thr Glu Ser
850                 855                 860                 865 gag cca gtc acc ata aat atc caa gac cta ctt tcc tgt tct aat ttt         2697
Glu Pro Val Thr Ile Asn Ile Gln Asp Leu Leu Ser Cys Ser Asn Phe
                870                 875                 880 gca gtg caa cac aga tat ctg ttt gaa gaa gac aat ctt tta cgg tct         2745
Ala Val Gln His Arg Tyr Leu Phe Glu Glu Asp Asn Leu Leu Arg Ser
            885                 890                 895 aca caa aag ctt tcc cat tca aca aaa cct tca gga agc cct ttg gaa         2793
Thr Gln Lys Leu Ser His Ser Thr Lys Pro Ser Gly Ser Pro Leu Glu
        900                 905                 910 gaa aaa cac gat caa tgc aaa tgt gaa aac ctt ata atg ttc cag aac         2841
Glu Lys His Asp Gln Cys Lys Cys Glu Asn Leu Ile Met Phe Gln Asn
915                 920                 925 ctt gca aac gaa gaa gta aga aaa tta aca cag cgc tta gaa gaa atg         2889
Leu Ala Asn Glu Glu Val Arg Lys Leu Thr Gln Arg Leu Glu Glu Met
930                 935                 940                 945 aca cag aga atg gaa gcc ctg gaa aat cgc ctg aga tac aga                 2931
Thr Gln Arg Met Glu Ala Leu Glu Asn Arg Leu Arg Tyr Arg
                950                 955
```

| | |
|---|---|
| tgaagattag aaatcgcgac acatttgtag tcattgtatc acggattaca atgaacgcag | 2991 |
| tgcagagccc caaagctcag gctattgtta aatcaataat gttgtgaagt aaaacaatca | 3051 |
| gtactgagaa acctggtttg ccacagaaca aagacaagaa gtatacacta acttgtataa | 3111 |
| atttatctag gaaaaaaatc cttcagaatt ctaagatgaa tttaccaggt gagaatgaat | 3171 |
| aagctatgca aggtattttg taatatactg tggacacaac ttgcttctgc ctcatcctgc | 3231 |
| cttagtgtgc aatctcattt gactatacga taaagtttgc acagtcttac ttctgtagaa | 3291 |
| cactggccat aggaaatgct gttttttgt actggacttt accttgatat atgtatatgg | 3351 |
| atgtatgcat aaaatcatag gacatatgta cttgtggaac aagttggatt ttttatacaa | 3411 |
| tattaaaatt caccacttca gagaaaagta aaaaaa | 3447 |

<210> SEQ ID NO 10
<211> LENGTH: 959
<212> TYPE: PRT

<213> ORGANISM: Homo sapiens

<400> SEQUENCE: 10

```
Met Glu Lys Met Leu Ala Gly Cys Phe Leu Leu Ile Leu Gly Gln Ile
  1               5                  10                  15

Val Leu Leu Pro Cys Glu Ala Arg Glu Arg Ser Arg Gly Arg Ser Ile
             20                  25                  30

Ser Arg Gly Arg His Ala Arg Thr His Pro Gln Thr Ala Leu Leu Glu
         35                  40                  45

Ser Ser Cys Glu Asn Lys Arg Ala Asp Leu Val Phe Ile Ile Asp Ser
     50                  55                  60

Ser Arg Ser Val Asn Thr His Asp Tyr Ala Lys Val Lys Glu Phe Ile
 65                  70                  75                  80

Val Asp Ile Leu Gln Phe Leu Asp Ile Gly Pro Asp Val Thr Arg Val
                 85                  90                  95

Gly Leu Leu Gln Tyr Gly Ser Thr Val Lys Asn Glu Phe Ser Leu Lys
            100                 105                 110

Thr Phe Lys Arg Lys Ser Glu Val Glu Arg Ala Val Lys Arg Met Arg
        115                 120                 125

His Leu Ser Thr Gly Thr Met Thr Gly Leu Ala Ile Gln Tyr Ala Leu
    130                 135                 140

Asn Ile Ala Phe Ser Glu Ala Glu Gly Ala Arg Pro Leu Arg Glu Asn
145                 150                 155                 160

Val Pro Arg Val Ile Met Ile Val Thr Asp Gly Arg Pro Gln Asp Ser
                165                 170                 175

Val Ala Glu Val Ala Ala Lys Ala Arg Asp Thr Gly Ile Leu Ile Phe
            180                 185                 190

Ala Ile Gly Val Gly Gln Val Asp Phe Asn Thr Leu Lys Ser Ile Gly
        195                 200                 205

Ser Glu Pro His Glu Asp His Val Phe Leu Val Ala Asn Phe Ser Gln
    210                 215                 220

Ile Glu Thr Leu Thr Ser Val Phe Gln Lys Lys Leu Cys Thr Ala His
225                 230                 235                 240

Met Cys Ser Thr Leu Glu His Asn Cys Ala His Phe Cys Ile Asn Ile
                245                 250                 255

Pro Gly Ser Tyr Val Cys Arg Cys Lys Gln Gly Tyr Ile Leu Asn Ser
            260                 265                 270

Asp Gln Thr Thr Cys Arg Ile Gln Asp Leu Cys Ala Met Glu Asp His
        275                 280                 285

Asn Cys Glu Gln Leu Cys Val Asn Val Pro Gly Ser Phe Val Cys Glu
    290                 295                 300

Cys Tyr Ser Gly Tyr Ala Leu Ala Glu Asp Gly Lys Arg Cys Val Ala
305                 310                 315                 320

Val Asp Tyr Cys Ala Ser Glu Asn His Gly Cys Glu His Glu Cys Val
                325                 330                 335

Asn Ala Asp Gly Ser Tyr Leu Cys Gln Cys His Glu Gly Phe Ala Leu
            340                 345                 350

Asn Pro Asp Glu Lys Thr Cys Thr Lys Ile Asp Tyr Cys Ala Ser Ser
        355                 360                 365

Asn His Gly Cys Gln Tyr Glu Cys Val Asn Thr Asp Asp Ser Tyr Ser
    370                 375                 380

Cys His Cys Leu Lys Gly Phe Thr Leu Asn Pro Asp Lys Lys Thr Cys
385                 390                 395                 400
```

-continued

```
Arg Arg Ile Asn Tyr Cys Ala Leu Asn Lys Pro Gly Cys Glu His Glu
            405                 410                 415
Cys Val Asn Met Glu Ser Tyr Tyr Cys Arg Cys His Arg Gly Tyr
        420                 425                 430
Thr Leu Asp Pro Asn Gly Lys Pro Cys Ser Arg Val Asp His Cys Ala
            435                 440                 445
Gln Gln Asp His Gly Cys Glu Gln Leu Cys Leu Asn Thr Glu Asp Ser
    450                 455                 460
Phe Val Cys Gln Cys Ser Glu Gly Phe Leu Ile Asn Glu Asp Leu Lys
465                 470                 475                 480
Thr Cys Ser Arg Val Asp Tyr Cys Leu Leu Ser Asp His Gly Cys Glu
                485                 490                 495
Tyr Ser Cys Val Asn Met Asp Arg Ser Phe Ala Cys Gln Cys Pro Glu
            500                 505                 510
Gly His Val Leu Arg Ser Asp Gly Lys Thr Cys Ala Lys Leu Asp Ser
        515                 520                 525
Cys Ala Leu Gly Asp His Gly Cys Glu His Ser Cys Val Ser Ser Glu
    530                 535                 540
Asp Ser Phe Val Cys Gln Cys Phe Glu Gly Tyr Ile Leu Arg Glu Asp
545                 550                 555                 560
Gly Lys Thr Cys Arg Arg Lys Asp Val Cys Gln Ala Ile Asp His Gly
                565                 570                 575
Cys Glu His Ile Cys Val Asn Ser Asp Asp Ser Tyr Thr Cys Glu Cys
            580                 585                 590
Leu Glu Gly Phe Arg Leu Thr Glu Asp Gly Lys Arg Cys Arg Ile Ser
        595                 600                 605
Ser Gly Lys Asp Val Cys Lys Ser Thr His His Gly Cys Glu His Ile
    610                 615                 620
Cys Val Asn Asn Gly Asn Ser Tyr Ile Cys Lys Cys Ser Glu Gly Phe
625                 630                 635                 640
Val Leu Ala Glu Asp Gly Arg Arg Cys Lys Lys Cys Thr Glu Gly Pro
                645                 650                 655
Ile Asp Leu Val Phe Val Ile Asp Gly Ser Lys Ser Leu Gly Glu Glu
            660                 665                 670
Asn Phe Glu Val Val Lys Gln Phe Val Thr Gly Ile Ile Asp Ser Leu
        675                 680                 685
Thr Ile Ser Pro Lys Ala Ala Arg Val Gly Leu Leu Gln Tyr Ser Thr
    690                 695                 700
Gln Val His Thr Glu Phe Thr Leu Arg Asn Phe Asn Ser Ala Lys Asp
705                 710                 715                 720
Met Lys Lys Ala Val Ala His Met Lys Tyr Met Gly Lys Gly Ser Met
                725                 730                 735
Thr Gly Leu Ala Leu Lys His Met Phe Glu Arg Ser Phe Thr Gln Gly
            740                 745                 750
Glu Gly Ala Arg Pro Phe Ser Thr Arg Val Pro Arg Ala Ala Ile Val
        755                 760                 765
Phe Thr Asp Gly Arg Ala Gln Asp Asp Val Ser Glu Trp Ala Ser Lys
770                 775                 780
Ala Lys Ala Asn Gly Ile Thr Met Tyr Ala Val Gly Val Gly Lys Ala
785                 790                 795                 800
Ile Glu Glu Glu Leu Gln Glu Ile Ala Ser Glu Pro Thr Asn Lys His
                805                 810                 815
Leu Phe Tyr Ala Glu Asp Phe Ser Thr Met Asp Glu Ile Ser Glu Lys
```

```
                    820                 825                 830
Leu Lys Lys Gly Ile Cys Glu Ala Leu Glu Asp Ser Asp Gly Arg Gln
            835                 840                 845

Asp Ser Pro Ala Gly Glu Leu Pro Lys Thr Val Gln Gln Pro Thr Glu
        850                 855                 860

Ser Glu Pro Val Thr Ile Asn Ile Gln Asp Leu Leu Ser Cys Ser Asn
865                 870                 875                 880

Phe Ala Val Gln His Arg Tyr Leu Phe Glu Asp Asn Leu Leu Arg
                885                 890                 895

Ser Thr Gln Lys Leu Ser His Ser Thr Lys Pro Ser Gly Ser Pro Leu
            900                 905                 910

Glu Glu Lys His Asp Gln Cys Lys Cys Glu Asn Leu Ile Met Phe Gln
        915                 920                 925

Asn Leu Ala Asn Glu Glu Val Arg Lys Leu Thr Gln Arg Leu Glu Glu
        930                 935                 940

Met Thr Gln Arg Met Glu Ala Leu Glu Asn Arg Leu Arg Tyr Arg
945                 950                 955

<210> SEQ ID NO 11
<211> LENGTH: 967
<212> TYPE: DNA
<213> ORGANISM: Homo sapiens
<220> FEATURE:
<221> NAME/KEY: CDS
<222> LOCATION: (166)..(900)

<400> SEQUENCE: 11
cggcccttct cacactcctg ccctgctgat gtggaacggg gtttgggggtt ctgcagggct      60 attgtctgcg ctgggaagg ggacaggccg ggaccgggac ctccgctcgc agccggccgc     120
accagcagga cagctggcct gaagctcaga gccggggcgt cgcc atg gcc cca cac     177
                                                  Met Ala Pro His
                                                   1 tgg gct gtc tgg ctg ctg gca gca agg ctg tgg ggc ctg ggc att ggg      225
Trp Ala Val Trp Leu Leu Ala Ala Arg Leu Trp Gly Leu Gly Ile Gly
  5                  10                  15                  20 gct gag gtg tgg tgg aac ctt gtg ccg cgt aag aca gtg tct tct ggg      273
Ala Glu Val Trp Trp Asn Leu Val Pro Arg Lys Thr Val Ser Ser Gly
             25                  30                  35 gag ctg gcc acg gta gta cgg cgg ttc tcc cag acc ggc atc cag gac      321
Glu Leu Ala Thr Val Val Arg Arg Phe Ser Gln Thr Gly Ile Gln Asp
         40                  45                  50 ttc ctg aca ctg acg ctg acg gag ccc act ggg ctt ctg tac gtg ggc      369
Phe Leu Thr Leu Thr Leu Thr Glu Pro Thr Gly Leu Leu Tyr Val Gly
     55                  60                  65 gcc cga gag gcc ctg ttt gcc ttc agc atg gag gcc ctg gag ctg caa      417
Ala Arg Glu Ala Leu Phe Ala Phe Ser Met Glu Ala Leu Glu Leu Gln
 70                  75                  80 gga gcg atc tcc tgg gag gcc ccc gtg gag aag aag act gag tgt atc      465
Gly Ala Ile Ser Trp Glu Ala Pro Val Glu Lys Lys Thr Glu Cys Ile
 85                  90                  95                 100 cag aaa ggg aag aac aac cag acc gag tgc ttc aac ttc atc cgc ttc      513
Gln Lys Gly Lys Asn Asn Gln Thr Glu Cys Phe Asn Phe Ile Arg Phe
                105                 110                 115 ctg cag ccc tac aat gcc tcc cac ctg tac gtc tgt ggc acc tac gcc      561
Leu Gln Pro Tyr Asn Ala Ser His Leu Tyr Val Cys Gly Thr Tyr Ala
            120                 125                 130 ttc cag ccc aag tgc acc tac gtc aac atg ctc acc ttc act ttg gag      609
Phe Gln Pro Lys Cys Thr Tyr Val Asn Met Leu Thr Phe Thr Leu Glu
```

```
                      135                 140                 145
cat gga gag ttt gaa gat ggg aag ggc aag tgt ccc tat gac cca gct      657
His Gly Glu Phe Glu Asp Gly Lys Gly Lys Cys Pro Tyr Asp Pro Ala
    150                 155                 160 aag ggc cat gct ggc ctt ctt gtg gat ggt gag ctg tac tcg gcc aca      705
Lys Gly His Ala Gly Leu Leu Val Asp Gly Glu Leu Tyr Ser Ala Thr
165                 170                 175                 180 ctc aac aac ttc ctg ggc acg gaa ccc att atc ctg cgt aac atg ggg      753
Leu Asn Asn Phe Leu Gly Thr Glu Pro Ile Ile Leu Arg Asn Met Gly
                185                 190                 195 ccc cac cac tcc atg aag aca gag tac ctg gcc ttt tgg ctc aac gaa      801
Pro His His Ser Met Lys Thr Glu Tyr Leu Ala Phe Trp Leu Asn Glu
            200                 205                 210 cct cac ttt gta ggc tct gcc tat gta cct gag agg gtg ggc ctg ctg      849
Pro His Phe Val Gly Ser Ala Tyr Val Pro Glu Arg Val Gly Leu Leu
        215                 220                 225 tgg aca atg gca tac tct ctt cca gcc cta gga gga ggg ctc cta aca      897
Trp Thr Met Ala Tyr Ser Leu Pro Ala Leu Gly Gly Gly Leu Leu Thr
    230                 235                 240 gtg taacttattg tgtccccgcg tatttatttg ttgtaaatat ttgagtattt           950
Val
245 ttatattgac aaataaa                                                   967

<210> SEQ ID NO 12
<211> LENGTH: 245
<212> TYPE: PRT
<213> ORGANISM: Homo sapiens

<400> SEQUENCE: 12

Met Ala Pro His Trp Ala Val Trp Leu Leu Ala Ala Arg Leu Trp Gly
1               5                   10                  15

Leu Gly Ile Gly Ala Glu Val Trp Trp Asn Leu Val Pro Arg Lys Thr
            20                  25                  30

Val Ser Ser Gly Glu Leu Ala Thr Val Val Arg Arg Phe Ser Gln Thr
        35                  40                  45

Gly Ile Gln Asp Phe Leu Thr Leu Thr Leu Thr Glu Pro Thr Gly Leu
    50                  55                  60

Leu Tyr Val Gly Ala Arg Glu Ala Leu Phe Ala Phe Ser Met Glu Ala
65                  70                  75                  80

Leu Glu Leu Gln Gly Ala Ile Ser Trp Glu Ala Pro Val Glu Lys Lys
                85                  90                  95

Thr Glu Cys Ile Gln Lys Gly Lys Asn Asn Gln Thr Glu Cys Phe Asn
            100                 105                 110

Phe Ile Arg Phe Leu Gln Pro Tyr Asn Ala Ser His Leu Tyr Val Cys
        115                 120                 125

Gly Thr Tyr Ala Phe Gln Pro Lys Cys Thr Tyr Val Asn Met Leu Thr
    130                 135                 140

Phe Thr Leu Glu His Gly Glu Phe Glu Asp Gly Lys Gly Lys Cys Pro
145                 150                 155                 160

Tyr Asp Pro Ala Lys Gly His Ala Gly Leu Leu Val Asp Gly Glu Leu
                165                 170                 175

Tyr Ser Ala Thr Leu Asn Asn Phe Leu Gly Thr Glu Pro Ile Ile Leu
            180                 185                 190

Arg Asn Met Gly Pro His His Ser Met Lys Thr Glu Tyr Leu Ala Phe
        195                 200                 205
```

-continued

```
Trp Leu Asn Glu Pro His Phe Val Gly Ser Ala Tyr Val Pro Glu Arg
    210                 215                 220

Val Gly Leu Leu Trp Thr Met Ala Tyr Ser Leu Pro Ala Leu Gly Gly
225                 230                 235                 240

Gly Leu Leu Thr Val
                245

<210> SEQ ID NO 13
<211> LENGTH: 1359
<212> TYPE: DNA
<213> ORGANISM: Homo sapiens
<220> FEATURE:
<221> NAME/KEY: CDS
<222> LOCATION: (45)..(1199)

<400> SEQUENCE: 13
ggcaccaggc cttccggaga gacgcagtcg gctgccaccc cggg atg ggt cgc tgg      56
                                              Met Gly Arg Trp
                                                1 tgc cag acc gtc gcg cgc ggg cag cgc ccc cgg acg tct gcc ccc tcc     104
Cys Gln Thr Val Ala Arg Gly Gln Arg Pro Arg Thr Ser Ala Pro Ser
  5              10                  15                  20 cgc gcc ggt gcc ctg ctg ctg ctt ctg ttg ctg agg tct gca ggt         152
Arg Ala Gly Ala Leu Leu Leu Leu Leu Leu Leu Arg Ser Ala Gly
                 25                  30                  35 tgc tgg ggc gca ggg gaa gcc ccg ggg gcg ctg tcc act gct gat ccc     200
Cys Trp Gly Ala Gly Glu Ala Pro Gly Ala Leu Ser Thr Ala Asp Pro
             40                  45                  50 gcc gac cag agc gtc cag tgt gtc ccc aag gcc acc tgt cct tcc agc     248
Ala Asp Gln Ser Val Gln Cys Val Pro Lys Ala Thr Cys Pro Ser Ser
         55                  60                  65 cgg cct cgc ctt ctc tgg cag acc ccg acc acc cag aca ctg ccc tcg     296
Arg Pro Arg Leu Leu Trp Gln Thr Pro Thr Thr Gln Thr Leu Pro Ser
     70                  75                  80 acc acc atg gag acc caa ttc cca gtt tct gaa ggc aaa gtc gac cca     344
Thr Thr Met Glu Thr Gln Phe Pro Val Ser Glu Gly Lys Val Asp Pro
 85                  90                  95                 100 tac cgc tcc tgt ggc ttt tcc tac gag cag gac ccc acc ctc agg gac     392
Tyr Arg Ser Cys Gly Phe Ser Tyr Glu Gln Asp Pro Thr Leu Arg Asp
                105                 110                 115 cca gaa gcc gtg gct cgg cgg tgg ccc tgg atg gtc agc gtg cgg gcc     440
Pro Glu Ala Val Ala Arg Arg Trp Pro Trp Met Val Ser Val Arg Ala
            120                 125                 130 aat ggc aca cac atc tgt gcc ggc acc atc att gcc tcc cag tgg gtg     488
Asn Gly Thr His Ile Cys Ala Gly Thr Ile Ile Ala Ser Gln Trp Val
        135                 140                 145 ctg act gtg gcc cac tgc ctg atc tgg cgt gat gtt atc tac tca gtg     536
Leu Thr Val Ala His Cys Leu Ile Trp Arg Asp Val Ile Tyr Ser Val
    150                 155                 160 agg gtg ggg agt ccg tgg att gac cag atg acg cag acc gcc tcc gat     584
Arg Val Gly Ser Pro Trp Ile Asp Gln Met Thr Gln Thr Ala Ser Asp
165                 170                 175                 180 gtc ccg gtg ctc cag gtc atc atg cat agc agg tac cgg gcc cag cgg     632
Val Pro Val Leu Gln Val Ile Met His Ser Arg Tyr Arg Ala Gln Arg
                185                 190                 195 ttc tgg tcc tgg gtg ggc cag gcc aac gac atc ggc ctc ctc aag ctc     680
Phe Trp Ser Trp Val Gly Gln Ala Asn Asp Ile Gly Leu Leu Lys Leu
            200                 205                 210 aag cag gaa ctc aag tac agc aat tac gtg cgg ccc atc tgc ctg cct     728
Lys Gln Glu Leu Lys Tyr Ser Asn Tyr Val Arg Pro Ile Cys Leu Pro
        215                 220                 225
```

```
ggc acg gac tat gtg ttg aag gac cat tcc cgc tgc act gtg acg ggc       776
Gly Thr Asp Tyr Val Leu Lys Asp His Ser Arg Cys Thr Val Thr Gly
    230                 235                 240 tgg gga ctt tcc aag gct gac ggc atg tgg cct cag ttc cgg acc att       824
Trp Gly Leu Ser Lys Ala Asp Gly Met Trp Pro Gln Phe Arg Thr Ile
245                 250                 255                 260 cag gag aag gaa gtc atc atc ctg aac aac aaa gag tgt gac aat ttc       872
Gln Glu Lys Glu Val Ile Ile Leu Asn Asn Lys Glu Cys Asp Asn Phe
                265                 270                 275 tac cac aac ttc acc aaa atc ccc act ctg gtt cag atc atc aag tcc       920
Tyr His Asn Phe Thr Lys Ile Pro Thr Leu Val Gln Ile Ile Lys Ser
            280                 285                 290 cag atg atg tgt gcg gag gac acc cac agg gag aag ttc tgc tat gag       968
Gln Met Met Cys Ala Glu Asp Thr His Arg Glu Lys Phe Cys Tyr Glu
        295                 300                 305 cta act gga gag ccc ttg gtc tgc tcc atg gag ggc acg tgg tac ctg      1016
Leu Thr Gly Glu Pro Leu Val Cys Ser Met Glu Gly Thr Trp Tyr Leu
    310                 315                 320 gtg gga ttg gtg agc tgg ggt gca ggc tgc cag aag agc gag gcc cca      1064
Val Gly Leu Val Ser Trp Gly Ala Gly Cys Gln Lys Ser Glu Ala Pro
325                 330                 335                 340 ccc atc tac cta cag gtc tcc tcc tac caa cac tgg atc tgg gac tgc      1112
Pro Ile Tyr Leu Gln Val Ser Ser Tyr Gln His Trp Ile Trp Asp Cys
                345                 350                 355 ctc aac ggg cag gcc ctg gcc ctg cca gcc cca tcc agg acc ctg ctc      1160
Leu Asn Gly Gln Ala Leu Ala Leu Pro Ala Pro Ser Arg Thr Leu Leu
            360                 365                 370 ctg gca ctc cca ctg ccc ctc agc ctc ctt gct gcc ctc tgactctgtg       1209
Leu Ala Leu Pro Leu Pro Leu Ser Leu Leu Ala Ala Leu
        375                 380                 385 tgccctccct cacttgtggg cccccttgc ctccgtgccc aggttgctgt gggtgcagct     1269
gtcacagccc tgagagtcag ggtggagatg aggtgctcaa ttaaacatta ctgttttcca    1329
tgtaaaaaaa aaaaaaaaaa aaaaaaaaa                                      1359

<210> SEQ ID NO 14
<211> LENGTH: 385
<212> TYPE: PRT
<213> ORGANISM: Homo sapiens

<400> SEQUENCE: 14

Met Gly Arg Trp Cys Gln Thr Val Ala Arg Gly Gln Arg Pro Arg Thr
1               5                   10                  15

Ser Ala Pro Ser Arg Ala Gly Ala Leu Leu Leu Leu Leu Leu Leu Leu
                20                  25                  30

Arg Ser Ala Gly Cys Trp Gly Ala Gly Glu Ala Pro Gly Ala Leu Ser
            35                  40                  45

Thr Ala Asp Pro Ala Asp Gln Ser Val Gln Cys Val Pro Lys Ala Thr
        50                  55                  60

Cys Pro Ser Ser Arg Pro Arg Leu Leu Trp Gln Thr Pro Thr Thr Gln
65                  70                  75                  80

Thr Leu Pro Ser Thr Thr Met Glu Thr Gln Phe Pro Val Ser Glu Gly
                85                  90                  95

Lys Val Asp Pro Tyr Arg Ser Cys Gly Phe Ser Tyr Glu Gln Asp Pro
                100                 105                 110

Thr Leu Arg Asp Pro Glu Ala Val Ala Arg Arg Trp Pro Trp Met Val
            115                 120                 125
```

```
Ser Val Arg Ala Asn Gly Thr His Ile Cys Ala Gly Thr Ile Ile Ala
    130                 135                 140
Ser Gln Trp Val Leu Thr Val Ala His Cys Leu Ile Trp Arg Asp Val
145                 150                 155                 160
Ile Tyr Ser Val Arg Val Gly Ser Pro Trp Ile Asp Gln Met Thr Gln
                165                 170                 175
Thr Ala Ser Asp Val Pro Val Leu Gln Val Ile Met His Ser Arg Tyr
            180                 185                 190
Arg Ala Gln Arg Phe Trp Ser Trp Val Gly Gln Ala Asn Asp Ile Gly
        195                 200                 205
Leu Leu Lys Leu Lys Gln Glu Leu Lys Tyr Ser Asn Tyr Val Arg Pro
210                 215                 220
Ile Cys Leu Pro Gly Thr Asp Tyr Val Leu Lys Asp His Ser Arg Cys
225                 230                 235                 240
Thr Val Thr Gly Trp Gly Leu Ser Lys Ala Asp Gly Met Trp Pro Gln
                245                 250                 255
Phe Arg Thr Ile Gln Glu Lys Glu Val Ile Ile Leu Asn Asn Lys Glu
            260                 265                 270
Cys Asp Asn Phe Tyr His Asn Phe Thr Lys Ile Pro Thr Leu Val Gln
        275                 280                 285
Ile Ile Lys Ser Gln Met Met Cys Ala Glu Asp Thr His Arg Glu Lys
290                 295                 300
Phe Cys Tyr Glu Leu Thr Gly Glu Pro Leu Val Cys Ser Met Glu Gly
305                 310                 315                 320
Thr Trp Tyr Leu Val Gly Leu Val Ser Trp Gly Ala Gly Cys Gln Lys
                325                 330                 335
Ser Glu Ala Pro Pro Ile Tyr Leu Gln Val Ser Ser Tyr Gln His Trp
            340                 345                 350
Ile Trp Asp Cys Leu Asn Gly Gln Ala Leu Ala Leu Pro Ala Pro Ser
        355                 360                 365
Arg Thr Leu Leu Leu Ala Leu Pro Leu Pro Leu Ser Leu Leu Ala Ala
370                 375                 380
Leu
385

<210> SEQ ID NO 15
<211> LENGTH: 1445
<212> TYPE: DNA
<213> ORGANISM: Homo sapiens
<220> FEATURE:
<221> NAME/KEY: CDS
<222> LOCATION: (732)..(1325)

<400> SEQUENCE: 15 caccctctg cctgccccag cccgcccatc gcttcccctt tggagcctcc tgctgggcca      60
ctggctggga tcaggacacc agtgatggta agtgctggcc cagactgaag ctcggagagg    120
cactctgctt gcccagcgtc acagtcttag ctcccaactg tcctggcttc cagtctccct    180
tgcttcccag atcccagact ctagcccag ccccgtctct ttcaccagct cctgggaccc    240
tacgcaatct gcgcctgcgt ctcatcagtc gccccacatg taactgtatc tacaaccagc    300
tgcaccagcg acacctgtcc aacccggccc ggctgggat gctatgtggg ggcccccagc    360
ctggggtgca gggcccctgt caggtctgat agggagaaga gaaggagcag aaggggaggg    420
gcctaaccct gggctggggg ttggactcac aggactgggg gaaagagctg caatcagagg    480
gtgtctgcca tagctgggct caggcatctg tccttggctt tgttgcctgg ctccagggag    540
```

-continued

```
attccggggg ccctgtgctg tgcctcgagc ctgacggaca ctgggttcag gctggcatca     600
tcagctttgc atcaagctgt gcccaggagg acgctcctgt gctgctgacc aacacagctg     660
ctcacagttc ctggctgcag gctcgagttc agggggcagc tttcctggcc cagagcccag     720
agaccccgga g atg agt gat gag gac agc tgt gta gcc tgt gga tcc ttg      770
              Met Ser Asp Glu Asp Ser Cys Val Ala Cys Gly Ser Leu
                1               5                  10 agg aca gca ggt ccc cag gca gga gca ccc tcc cca tgg ccc tgg gag       818
Arg Thr Ala Gly Pro Gln Ala Gly Ala Pro Ser Pro Trp Pro Trp Glu
     15                 20                  25 gcc agg ctg atg cac cag gga cag ctg gcc tgt ggc gga gcc ctg gtg       866
Ala Arg Leu Met His Gln Gly Gln Leu Ala Cys Gly Gly Ala Leu Val
 30              35                  40                  45 tca gag gag gcg gtg cta act gct gcc cac tgc ttc att ggg cgc cag       914
Ser Glu Glu Ala Val Leu Thr Ala Ala His Cys Phe Ile Gly Arg Gln
             50                  55                  60 gcc cca gag gaa tgg agc gta ggg ctg ggg acc aga ccg gag gag tgg       962
Ala Pro Glu Glu Trp Ser Val Gly Leu Gly Thr Arg Pro Glu Glu Trp
                 65                  70                  75 ggc ctg aag cag ctc atc ctg cat gga gcc tac acc cac cct gag ggg      1010
Gly Leu Lys Gln Leu Ile Leu His Gly Ala Tyr Thr His Pro Glu Gly
             80                  85                  90 ggc tac gac atg gcc ctc ctg ctg gcc cag cct gtg aca ctg gga          1058
Gly Tyr Asp Met Ala Leu Leu Leu Ala Gln Pro Val Thr Leu Gly
     95                 100                 105 gcc agc ctg cgg ccc ctc tgc ctg ccc tat gct gac cac cac ctg cct      1106
Ala Ser Leu Arg Pro Leu Cys Leu Pro Tyr Ala Asp His His Leu Pro
110                 115                 120                 125 gat ggg gag cgt ggc tgg gtt ctg gga cgg gcc cgc cca gga gca ggc      1154
Asp Gly Glu Arg Gly Trp Val Leu Gly Arg Ala Arg Pro Gly Ala Gly
                130                 135                 140 atc agc tcc ctc cag aca gtg ccc gtg acc ctc ctg ggg cct agg gcc      1202
Ile Ser Ser Leu Gln Thr Val Pro Val Thr Leu Leu Gly Pro Arg Ala
                145                 150                 155 tgc agc cgg ctg cat gca gct cct ggg ggt gat ggc agc cct att ctg      1250
Cys Ser Arg Leu His Ala Ala Pro Gly Gly Asp Gly Ser Pro Ile Leu
            160                 165                 170 ccg ggg atg gtg tgt acc agt gct gtg ggt gag ctg ccc agc tgt gag      1298
Pro Gly Met Val Cys Thr Ser Ala Val Gly Glu Leu Pro Ser Cys Glu
        175                 180                 185 gtg agc ccc agg ccc cca cac ctt acc taacaggccc ctggcatccc           1345
Val Ser Pro Arg Pro Pro His Leu Thr
190                 195 ctcacccaat agctcaagaa cggaccttcc aggcttggcc tctggaccca cctcccacct     1405
gaagctaagc cttttgcca attagccccc aaacagccag                           1445

<210> SEQ ID NO 16
<211> LENGTH: 198
<212> TYPE: PRT
<213> ORGANISM: Homo sapiens

<400> SEQUENCE: 16

Met Ser Asp Glu Asp Ser Cys Val Ala Cys Gly Ser Leu Arg Thr Ala
  1               5                  10                  15

Gly Pro Gln Ala Gly Ala Pro Ser Pro Trp Pro Trp Glu Ala Arg Leu
             20                  25                  30

Met His Gln Gly Gln Leu Ala Cys Gly Gly Ala Leu Val Ser Glu Glu
         35                  40                  45
```

```
Ala Val Leu Thr Ala Ala His Cys Phe Ile Gly Arg Gln Ala Pro Glu
        50                  55                  60

Glu Trp Ser Val Gly Leu Gly Thr Arg Pro Glu Glu Trp Gly Leu Lys
 65                  70                  75                  80

Gln Leu Ile Leu His Gly Ala Tyr Thr His Pro Glu Gly Gly Tyr Asp
                    85                  90                  95

Met Ala Leu Leu Leu Ala Gln Pro Val Thr Leu Gly Ala Ser Leu
                100                 105                 110

Arg Pro Leu Cys Leu Pro Tyr Ala Asp His His Leu Pro Asp Gly Glu
            115                 120                 125

Arg Gly Trp Val Leu Gly Arg Ala Arg Pro Gly Ala Gly Ile Ser Ser
    130                 135                 140

Leu Gln Thr Val Pro Val Thr Leu Leu Gly Pro Arg Ala Cys Ser Arg
145                 150                 155                 160

Leu His Ala Ala Pro Gly Gly Asp Gly Ser Pro Ile Leu Pro Gly Met
                165                 170                 175

Val Cys Thr Ser Ala Val Gly Glu Leu Pro Ser Cys Glu Val Ser Pro
                180                 185                 190

Arg Pro Pro His Leu Thr
                195

<210> SEQ ID NO 17
<211> LENGTH: 1600
<212> TYPE: DNA
<213> ORGANISM: Homo sapiens
<220> FEATURE:
<221> NAME/KEY: CDS
<222> LOCATION: (51)..(1355)

<400> SEQUENCE: 17
cttaacagcc acttgtttca tcccacctgg gcattaggtt gacttcaaag atg cct        56
                                                      Met Pro
                                                        1 cag tta ctg caa aac att aat ggg atc atc gag gcc ttc agg cgc tat      104
Gln Leu Leu Gln Asn Ile Asn Gly Ile Ile Glu Ala Phe Arg Arg Tyr
        5                   10                  15 gca agg acg gag ggc aac tgc aca gcg ctc acc cga ggg gag ctg aaa      152
Ala Arg Thr Glu Gly Asn Cys Thr Ala Leu Thr Arg Gly Glu Leu Lys
 20                  25                  30 aga ctc ttg gag caa gag ttt gcc gat gtg att gtg aaa ccc cac gat      200
Arg Leu Leu Glu Gln Glu Phe Ala Asp Val Ile Val Lys Pro His Asp
 35                  40                  45                  50 cca gca act gtg gat gag gtc ctg cgt ctg ctg gat gaa gac cac aca      248
Pro Ala Thr Val Asp Glu Val Leu Arg Leu Leu Asp Glu Asp His Thr
                55                  60                  65 ggg act gtg gaa ttc aag gaa ttc ctg gtc tta gtg ttt aaa gtt gcc      296
Gly Thr Val Glu Phe Lys Glu Phe Leu Val Leu Val Phe Lys Val Ala
             70                  75                  80 cag gcc tgt ttc aag aca ctg agc gag agt gct gag gga gcc tgc ggc      344
Gln Ala Cys Phe Lys Thr Leu Ser Glu Ser Ala Glu Gly Ala Cys Gly
         85                  90                  95 tct caa gag tct gga agc ctc cac tct ggg gcc tcg cag gag ctg ggc      392
Ser Gln Glu Ser Gly Ser Leu His Ser Gly Ala Ser Gln Glu Leu Gly
    100                 105                 110 gaa gga cag aga agt ggc act gaa gtg gga agg gcg ggg aaa ggg cag      440
Glu Gly Gln Arg Ser Gly Thr Glu Val Gly Arg Ala Gly Lys Gly Gln
115                 120                 125                 130 cat tat gag ggg agc agc cac aga cag agc cag cag ggt tcc aga ggg      488
```

```
                    His Tyr Glu Gly Ser Ser His Arg Gln Ser Gln Gln Gly Ser Arg Gly
                                    135                 140                 145 cag aac agg cct ggg gtt cag acc cag ggt cag gcc act ggc tct gcg        536
Gln Asn Arg Pro Gly Val Gln Thr Gln Gly Gln Ala Thr Gly Ser Ala
            150                 155                 160 tgg gtc agc agc tat gac agg caa gct gag tcc cag agc cag gaa aga        584
Trp Val Ser Ser Tyr Asp Arg Gln Ala Glu Ser Gln Ser Gln Glu Arg
            165                 170                 175 ata agc ccg cag ata caa ctc tct ggg cag aca gag cag acc cag aaa        632
Ile Ser Pro Gln Ile Gln Leu Ser Gly Gln Thr Glu Gln Thr Gln Lys
            180                 185                 190 gct gga gaa ggc aag agg aat cag aca aca gag atg agg cca gag aga        680
Ala Gly Glu Gly Lys Arg Asn Gln Thr Thr Glu Met Arg Pro Glu Arg
195                 200                 205                 210 cag cca cag acc agg gaa cag gac aga gcc cac cag aca ggt gag act        728
Gln Pro Gln Thr Arg Glu Gln Asp Arg Ala His Gln Thr Gly Glu Thr
            215                 220                 225 gtg act gga tct gga act cag acc cag gca ggt gcc acc cag act gtg        776
Val Thr Gly Ser Gly Thr Gln Thr Gln Ala Gly Ala Thr Gln Thr Val
            230                 235                 240 gag cag gac agc agc cac cag aca gga agc acc agc acc cag aca cag        824
Glu Gln Asp Ser Ser His Gln Thr Gly Ser Thr Ser Thr Gln Thr Gln
            245                 250                 255 gag tcc acc aat ggc cag aac aga ggg act gag atc cac ggt caa ggc        872
Glu Ser Thr Asn Gly Gln Asn Arg Gly Thr Glu Ile His Gly Gln Gly
            260                 265                 270 agg agc cag acc agc cag gct gtg aca gga gga cac act cag ata cag        920
Arg Ser Gln Thr Ser Gln Ala Val Thr Gly Gly His Thr Gln Ile Gln
275                 280                 285                 290 gca ggg tca cac acc gag act gtg gag cag gac aga agc caa act gta        968
Ala Gly Ser His Thr Glu Thr Val Glu Gln Asp Arg Ser Gln Thr Val
            295                 300                 305 agc cac gga ggg gct aga gaa cag gga cag acc cag acg cag cca ggc       1016
Ser His Gly Gly Ala Arg Glu Gln Gly Gln Thr Gln Thr Gln Pro Gly
            310                 315                 320 agt ggt caa aga tgg atg caa gtg agc aac cct gag gca gga gag aca       1064
Ser Gly Gln Arg Trp Met Gln Val Ser Asn Pro Glu Ala Gly Glu Thr
            325                 330                 335 gta ccg gga gga cag gcc cag act ggg gca agc act gag tca gga agg       1112
Val Pro Gly Gly Gln Ala Gln Thr Gly Ala Ser Thr Glu Ser Gly Arg
            340                 345                 350 cag gag tgg agc agc act cac cca agg cgc tgt gtg aca gaa ggg cag       1160
Gln Glu Trp Ser Ser Thr His Pro Arg Arg Cys Val Thr Glu Gly Gln
355                 360                 365                 370 gga gac aga cag ccc aca gtg gtt ggt gag gaa tgg gtt gat gac cac       1208
Gly Asp Arg Gln Pro Thr Val Val Gly Glu Glu Trp Val Asp Asp His
            375                 380                 385 tca agg gag aca gtg atc ctc agg ctg gac cag ggc aac ttg cat acc       1256
Ser Arg Glu Thr Val Ile Leu Arg Leu Asp Gln Gly Asn Leu His Thr
            390                 395                 400 agt gtt tcc tca gca cag ggc cag gat gca gcc cag tca gaa gag aag       1304
Ser Val Ser Ser Ala Gln Gly Gln Asp Ala Ala Gln Ser Glu Glu Lys
            405                 410                 415 cga ggc atc aca gct aga gag ctg tat tcc tac ttg aga agc acc aag       1352
Arg Gly Ile Thr Ala Arg Glu Leu Tyr Ser Tyr Leu Arg Ser Thr Lys
            420                 425                 430 cca tgacttcccc gactccaatg tccagtactg gaagaagaca gctggagaga            1405
Pro
435
```

```
gtttggcttg tcctgcatgg ccaatccagt gggtgcatcc ctggacatca gctcttcatt    1465
atgcagcttc cctttttaggt ctttctcaat gagataattt ctgcaaggag ctttctatcc   1525
tgaactcttc tttcttacct gctttgcggt gcagaccctc tcaggagcag gaagactcag   1585
aacaagtcac ccctt                                                     1600
```

<210> SEQ ID NO 18
<211> LENGTH: 435
<212> TYPE: PRT
<213> ORGANISM: Homo sapiens

<400> SEQUENCE: 18

```
Met Pro Gln Leu Leu Gln Asn Ile Asn Gly Ile Ile Glu Ala Phe Arg
 1               5                  10                  15

Arg Tyr Ala Arg Thr Glu Gly Asn Cys Thr Ala Leu Thr Arg Gly Glu
             20                  25                  30

Leu Lys Arg Leu Leu Glu Gln Glu Phe Ala Asp Val Ile Val Lys Pro
         35                  40                  45

His Asp Pro Ala Thr Val Asp Glu Val Leu Arg Leu Leu Asp Glu Asp
     50                  55                  60

His Thr Gly Thr Val Glu Phe Lys Glu Phe Leu Val Leu Val Phe Lys
 65                  70                  75                  80

Val Ala Gln Ala Cys Phe Lys Thr Leu Ser Glu Ser Ala Glu Gly Ala
                 85                  90                  95

Cys Gly Ser Gln Glu Ser Gly Ser Leu His Ser Gly Ala Ser Gln Glu
            100                 105                 110

Leu Gly Glu Gly Gln Arg Ser Gly Thr Glu Val Gly Arg Ala Gly Lys
        115                 120                 125

Gly Gln His Tyr Glu Gly Ser Ser His Arg Gln Ser Gln Gln Gly Ser
    130                 135                 140

Arg Gly Gln Asn Arg Pro Gly Val Gln Thr Gln Gly Gln Ala Thr Gly
145                 150                 155                 160

Ser Ala Trp Val Ser Ser Tyr Asp Arg Gln Ala Glu Ser Gln Ser Gln
                165                 170                 175

Glu Arg Ile Ser Pro Gln Ile Gln Leu Ser Gly Gln Thr Glu Gln Thr
            180                 185                 190

Gln Lys Ala Gly Glu Gly Lys Arg Asn Gln Thr Thr Glu Met Arg Pro
        195                 200                 205

Glu Arg Gln Pro Gln Thr Arg Glu Gln Asp Arg Ala His Gln Thr Gly
    210                 215                 220

Glu Thr Val Thr Gly Ser Gly Thr Gln Thr Gln Ala Gly Ala Thr Gln
225                 230                 235                 240

Thr Val Glu Gln Asp Ser Ser His Gln Thr Gly Ser Thr Ser Thr Gln
                245                 250                 255

Thr Gln Glu Ser Thr Asn Gly Gln Asn Arg Gly Thr Glu Ile His Gly
            260                 265                 270

Gln Gly Arg Ser Gln Thr Ser Gln Ala Val Thr Gly His Thr Gln
        275                 280                 285

Ile Gln Ala Gly Ser His Thr Glu Thr Val Glu Gln Asp Arg Ser Gln
    290                 295                 300

Thr Val Ser His Gly Gly Ala Arg Glu Gln Gln Thr Gln Thr Gln
305                 310                 315                 320

Pro Gly Ser Gly Gln Arg Trp Met Gln Val Ser Asn Pro Glu Ala Gly
                325                 330                 335
```

```
Glu Thr Val Pro Gly Gly Gln Ala Gln Thr Gly Ala Ser Thr Glu Ser
                340                 345                 350

Gly Arg Gln Glu Trp Ser Ser Thr His Pro Arg Arg Cys Val Thr Glu
            355                 360                 365

Gly Gln Gly Asp Arg Gln Pro Thr Val Val Gly Glu Glu Trp Val Asp
    370                 375                 380

Asp His Ser Arg Glu Thr Val Ile Leu Arg Leu Asp Gln Gly Asn Leu
385                 390                 395                 400

His Thr Ser Val Ser Ser Ala Gln Gly Gln Asp Ala Ala Gln Ser Glu
                405                 410                 415

Glu Lys Arg Gly Ile Thr Ala Arg Glu Leu Tyr Ser Tyr Leu Arg Ser
            420                 425                 430

Thr Lys Pro
        435

<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: PCR PRIMER

<400> SEQUENCE: 19
ctcgtcagat ctccaccatg agtgatgagg acagctgtgt ag                        42

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence: PCR PRIMER

<400> SEQUENCE: 20
ctcgtcctcg aggcagctgg ttggttggct tatgttg                              37

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: PCR PRIMER

<400> SEQUENCE: 21
ctcgtcctcg agggtaagcc tatccctaac                                      30

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence: PCR PRIMER

<400> SEQUENCE: 22
ctcgtcgggc ccctgatcag cgggtttaaa c                                    31

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence: PCR PRIMER

<400> SEQUENCE: 23
```

```
ctcgtcggat cctggggcgc aggggaagcc ccggg                                35
```

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence: PCR PRIMER

<400> SEQUENCE: 24

```
ctcgtcctcg aggagggcag caaggaggct gaggggcag                            39
```

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: PCR PRIMER

<400> SEQUENCE: 25

```
ggcctctccg tacccttctc                                                 20
```

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: PCR PRIMER

<400> SEQUENCE: 26

```
agaggctctt ggcgcagtt                                                  19
```

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: PCR PRIMER

<400> SEQUENCE: 27

```
accaggatca cgacctccgc agg                                             23
```

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: PCR PRIMER

<400> SEQUENCE: 28

```
gcctggcacg gactatgtgt                                                 20
```

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: PCR PRIMER

<400> SEQUENCE: 29

```
gccgtcagcc ttggaaagt                                                  19
```

<210> SEQ ID NO 30
<211> LENGTH: 22
<212> TYPE: DNA
<213> ORGANISM: Artificial Sequence -continued

```
<220> FEATURE:
<223> OTHER INFORMATION: Description of Artificial Sequence: PCR PRIMER

<400> SEQUENCE: 30
ccattcccgc tgcactgtga cg                                              22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: PCR PRIMER

<400> SEQUENCE: 31
cctgccagga tgactgtcaa tt                                              22

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: PCR PRIMER

<400> SEQUENCE: 32
tggtcctaac tgcaccacag tct                                             23

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: PCR PRIMER

<400> SEQUENCE: 33
ccagctggtc caagttttct tcatgcaa                                        28

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: PCR PRIMER

<400> SEQUENCE: 34
gtgatcctca ggctggacca                                                 20

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: PCR PRIMER

<400> SEQUENCE: 35
ttctgactgg gctgcatcc                                                  19

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: PCR PRIMER

<400> SEQUENCE: 36
ccagtgtttc ctcagcacag ggcc                                            24
```